United States Patent
Nguyen

(10) Patent No.: US 11,874,601 B2
(45) Date of Patent: Jan. 16, 2024

(54) RESIST COMPOSITION, METHOD OF FORMING RESIST PATTERN, COMPOUND, AND ACID DIFFUSION-CONTROLLING AGENT

(71) Applicant: TOKYO OHKA KOGYO CO., LTD., Kawasaki (JP)

(72) Inventor: KhanhTin Nguyen, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 303 days.

(21) Appl. No.: 17/304,442

(22) Filed: Jun. 21, 2021

(65) Prior Publication Data

US 2022/0011665 A1 Jan. 13, 2022

(30) Foreign Application Priority Data

Jul. 7, 2020 (JP) ................. 2020-117327

(51) Int. Cl.
| | | |
|---|---|---|
| *G03F 7/004* | (2006.01) | |
| *G03F 7/038* | (2006.01) | |
| *G03F 7/039* | (2006.01) | |
| *C07D 333/70* | (2006.01) | |
| *C07D 327/06* | (2006.01) | |
| *C07C 381/02* | (2006.01) | |
| *C07D 319/20* | (2006.01) | |
| *C07D 311/66* | (2006.01) | |
| *C07D 317/50* | (2006.01) | |
| *C07C 381/12* | (2006.01) | |

(52) U.S. Cl.
CPC .......... *G03F 7/0045* (2013.01); *C07C 381/12* (2013.01); *C07D 311/66* (2013.01); *C07D 317/50* (2013.01); *C07D 319/20* (2013.01); *C07D 327/06* (2013.01); *C07D 333/70* (2013.01); *G03F 7/0382* (2013.01); *G03F 7/0392* (2013.01)

(58) Field of Classification Search
None
See application file for complete search history.

(56) References Cited

U.S. PATENT DOCUMENTS

2002/0037479 A1* 3/2002 Schwartzkopf ......... G03F 7/425
430/464
2013/0157197 A1 6/2013 Yoshitaka et al.

FOREIGN PATENT DOCUMENTS

| JP | 2013-125146 A | 6/2013 |
| JP | 2014062990 A * | 4/2014 |

OTHER PUBLICATIONS

English Machine Translation of JP-2014062990-A (Year: 2014).*

* cited by examiner

*Primary Examiner* — Mark F. Huff
*Assistant Examiner* — Nicholas E Brown
(74) *Attorney, Agent, or Firm* — Knobbe, Martens, Olson & Bear, LLP

(57) ABSTRACT

A resist composition that contains a base material component exhibiting changed solubility in a developing solution under action of acid and a compound (D0) represented by General Formula (d0), in which $R^{01}$, $R^{02}$, $R^{03}$, and $R^{04}$ each independently represents a hydrogen atom, a hydroxy group, a halogen atom, or an alkyl group; alternatively, $R^{01}$ and $R^{02}$, $R^{02}$ and $R^{03}$, or $R^{03}$ and $R^{04}$ are bonded to each other to form an aromatic ring; $R^{05}$ represents a hydrogen atom or an alkyl group; Y represents a group that forms an alicyclic group together with a carbon atom *C; provided that at least one of the carbon atoms that form the alicyclic group is substituted with an ether bond, a thioether bond, a carbonyl group, a sulfinyl group, or a sulfonyl group; m represents an integer of 1 or more, and $M^{m+}$ represents an m-valent organic cation.

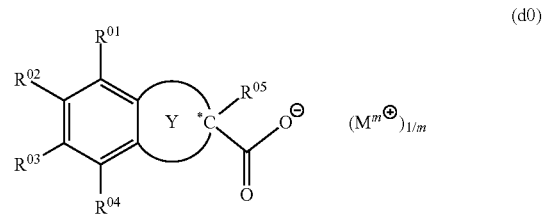

9 Claims, No Drawings

RESIST COMPOSITION, METHOD OF FORMING RESIST PATTERN, COMPOUND, AND ACID DIFFUSION-CONTROLLING AGENT

Priority is claimed on Japanese Patent Application No. 2020-117327, filed on Jul. 7, 2020, the content of which is incorporated herein by reference.

BACKGROUND OF THE INVENTION

Field of the Invention

The present invention relates to a resist composition, a method of forming a resist pattern, a compound, and an acid diffusion-controlling agent.

Description of Related Art

In recent years, in the production of semiconductor elements and liquid crystal display elements, advances in lithography techniques have led to a rapid progress in the field of pattern miniaturization. Typically, these miniaturization techniques involve shortening the wavelength (increasing the energy) of the light source for exposure.

Resist materials for use with these types of light sources for exposure require lithography characteristics such as a high resolution capable of reproducing patterns of minute dimensions, and a high level of sensitivity to these types of light sources for exposure.

As a resist material that satisfies these requirements, a chemical amplification-type resist composition which contains a base material component exhibiting changed solubility in a developing solution under action of acid, and an acid generator component that generates an acid upon exposure has been conventionally used.

In the formation of the resist pattern, the behavior of an acid generated from an acid generator component upon exposure is considered as one factor that has a great influence on lithography characteristics.

On the other hand, a chemical amplification-type resist composition having both an acid generator component and an acid diffusion-controlling agent that controls the diffusion of an acid generated from the acid generator component upon exposure has been proposed.

For example, Japanese Unexamined Patent Application, First Publication No. 2013-125146 discloses a resist composition containing a resin component exhibiting changed solubility in a developing solution under action of acid, an acid generator component, and a photoreactive quencher having an anion moiety that has a specific structure, as an acid diffusion-controlling agent.

This photoreactive quencher is said to be a component that exhibits a quenching effect by causing an ion exchange reaction with an acid generated from an acid generator component. By blending such a photoreactive quencher, the diffusion of the acid generated from the acid generator component from the exposed portion to the unexposed portion of the resist film is controlled, and the lithography characteristics are improved.

CITATION LIST

Patent Document

[Patent Document 1] Japanese Unexamined Patent Application, First Publication No. 2013-125146

SUMMARY OF THE INVENTION

Recently, with further advances in lithography techniques, rapid progress in the field of pattern miniaturization is being achieved together with the expansion of application fields. Along with this progress, in a case where manufacturing a semiconductor element or the like, a technique capable of forming, in a good shape, a fine pattern having a pattern width dimension of less than several tens of nanometers is required.

However, in the conventional resist composition such as that described in Japanese Unexamined Patent Application, First Publication No. 2013-125146 described above, there is still room for improvement in achieving both high sensitivity and lithography characteristics with respect to the required level. Among the lithography characteristics, particularly, the fine resolution needs to be further improved.

The present invention has been made in consideration of the above circumstances, and an object of the present invention is to provide a resist composition having the good fine resolution, a method of forming a resist pattern, a compound, and an acid diffusion-controlling agent.

In order to achieve the above-described object, the present invention employs the following configurations.

That is, a first aspect of the present invention is a resist composition generating an acid upon exposure and having solubility in a developing solution, which is changed by action of an acid, where the resist composition is characterized by containing a base material component (A) having solubility in a developing solution, which is changed by action of an acid, and a compound (D0) represented by General Formula (d0).

[Chemical Formula 1]

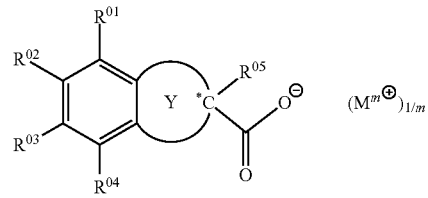

[In the formula, $R^{01}$, $R^{02}$, $R^{03}$, and $R^{04}$ each independently represent a hydrogen atom, a hydroxy group, a halogen atom, or an alkyl group having 1 to 5 carbon atoms. Alternatively, $R^{01}$ and $R^{02}$, $R^{02}$ and $R^{03}$, or $R^{03}$ and $R^{04}$ are bonded to each other to form an aromatic ring. The aromatic ring may have a substituent. $R^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group. m represents an integer of 1 or more, and $M^{m+}$ represents an m-valent organic cation.]

A second aspect according to the present invention is a method of forming a resist pattern, which is characterized by including a step of forming a resist film on a support using the resist composition according to the first aspect, a step of exposing the resist film, and a step of developing the exposed resist film to form a resist pattern.

A third aspect of the present invention is a compound represented by General Formula (d0).

[Chemical Formula 2]

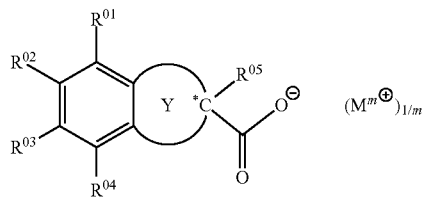

(d0)

[In the formula, $R^{01}$, $R^{02}$, $R^{03}$, and $R^{04}$ each independently represent a hydrogen atom, a hydroxy group, a halogen atom, or an alkyl group having 1 to 5 carbon atoms. Alternatively, $R^{01}$ and $R^{02}$, $R^{02}$ and $R^{03}$, or $R^{03}$ and $R^{04}$ are bonded to each other to form an aromatic ring. The aromatic ring may have a substituent. $R^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group. m represents an integer of 1 or more, and $M^{m+}$ represents an m-valent organic cation.]

A fourth aspect of the present invention is an acid diffusion-controlling agent, which is characterized by containing the compound according to the third aspect described above.

According to the present invention, it is possible to provide a resist composition having the good fine resolution, a method of forming a resist pattern, a compound, and an acid diffusion-controlling agent.

DETAILED DESCRIPTION OF THE INVENTION

In the present specification and the scope of the present claims, the term "aliphatic" is a relative concept used with respect to the term "aromatic" and defines a group or compound that has no aromaticity.

The term "alkyl group" includes a monovalent saturated hydrocarbon group that is linear, branched, or cyclic, unless otherwise specified. The same applies to the alkyl group of an alkoxy group.

The term "alkylene group" includes a divalent saturated hydrocarbon group that is linear, branched, or cyclic, unless otherwise specified.

Examples of the "halogen atom" include a fluorine atom, a chlorine atom, a bromine atom, and an iodine atom.

The term "constitutional unit" means a monomer unit (monomeric unit) that constitutes a polymer compound (a resin, a polymer, or a copolymer).

In a case where "may have a substituent" is described, both of a case where a hydrogen atom (—H) is substituted with a monovalent group and a case where a methylene group (—CH$_2$—) is substituted with a divalent group are included.

The term "exposure" is used as a general concept that includes irradiation with any form of radiation.

The term "acid-decomposable group" indicates a group in which at least a part of a bond in the structure of the acid-decomposable group can be cleaved by action of an acid.

Examples of the acid-decomposable group having a polarity which is increased by action of an acid include groups which are decomposed by action of an acid to generate a polar group.

Examples of the polar group include a carboxy group, a hydroxyl group, an amino group, and a sulfo group (—SO$_3$H).

More specific examples of the acid-decomposable group include a group in which the above-described polar group has been protected with an acid-dissociable group (such as a group in which a hydrogen atom of the OH-containing polar group has been protected with an acid-dissociable group).

The "acid-dissociable group" indicates any one of (i) a group in which a bond between the acid-dissociable group and an atom adjacent to the acid-dissociable group can be cleaved by action of an acid; and (ii) a group in which a part of bonds are cleaved by action of an acid, and then a decarboxylation reaction occurs, thereby cleaving the bond between the acid-dissociable group and the atom adjacent to the acid-dissociable group."

It is necessary that the acid-dissociable group that constitutes the acid-decomposable group be a group that exhibits a lower polarity than the polar group generated by the dissociation of the acid-dissociable group. Thus, in a case where the acid-dissociable group is dissociated by action of an acid, a polar group exhibiting a higher polarity than the acid-dissociable group is generated, thereby increasing the polarity. As a result, the polarity of the entire component (A1) is increased. By the increase in the polarity, the solubility in a developing solution relatively changes. The solubility in a developing solution is increased in a case where the developing solution is an alkali developing solution, whereas the solubility in a developing solution is decreased in a case where the developing solution is an organic developing solution.

The "base material component" is an organic compound having a film-forming ability. The organic compounds used as the base material component are roughly classified into a non-polymer and a polymer. As the non-polymer, those having a molecular weight of 500 or more and less than 4,000 are usually used. Hereinafter, a "low-molecular-weight compound" refers to a non-polymer having a molecular weight of 500 or more and less than 4,000. As the polymer, those having a molecular weight of 1,000 or more are usually used. Hereinafter, a "resin", a "polymer compound", or a "polymer" refers to a polymer having a molecular weight of 1,000 or more. As the molecular weight of the polymer, a polystyrene-equivalent mass-average molecular weight determined by gel permeation chromatography (GPC) is used.

A "constitutional unit derived from" means a constitutional unit that is formed by the cleavage of a multiple bond between carbon atoms, for example, an ethylenic double bond.

In the "acrylic acid ester", the hydrogen atom bonded to the carbon atom at the α-position may be substituted with a substituent. The substituent ($R^{αx}$) that is substituted for the hydrogen atom bonded to the carbon atom at the α-position is an atom other than a hydrogen atom or a group. Further, an itaconic acid diester in which the substituent ($R^{αx}$) is substituted with a substituent having an ester bond or α-hydroxyacryl ester in which the substituent ($R^{αx}$) is substituted with a hydroxyalkyl group or a group in which a hydroxyl group thereof is modified can be also mentioned as an acrylic acid ester. A carbon atom at the α-position of acrylic acid ester indicates the carbon atom bonded to the carbonyl group of acrylic acid, unless otherwise specified.

Hereinafter, acrylic acid ester in which the hydrogen atom bonded to the carbon atom at the α-position is substituted with a substituent is also referred to as an α-substituted acrylic acid ester".

The term "derivative" includes a compound in which the hydrogen atom at the α-position of the object compound has been substituted with another substituent such as an alkyl group or a halogenated alkyl group; and derivatives thereof. Examples of the derivatives thereof include a derivative in which the hydrogen atom of the hydroxyl group of the object compound in which the hydrogen atom at the α-position may be substituted with a substituent is substituted with an organic group; and a derivative in which a substituent other than a hydroxyl group is bonded to the object compound in which the hydrogen atom at the α-position may be substituted with a substituent. The α-position refers to the first carbon atom adjacent to the functional group unless otherwise specified.

Examples of the substituent that is substituted for the hydrogen atom at the α-position of hydroxystyrene include the same group as $R^{\alpha x}$.

In the present specification and the scope of the present claims, asymmetric carbon atoms may be present, and thus enantiomers or diastereomers may be present depending on the structures of the chemical formula. In that case, these isomers are represented by one chemical formula. These isomers may be used alone or in the form of a mixture.

<Resist Composition>

The resist composition according to the present embodiment is a resist composition that generates an acid upon exposure and exhibiting changed solubility in a developing solution under action of acid.

Such a resist composition contains a base material component (A) (hereinafter, also referred to as a "component (A)") exhibiting changed solubility in a developing solution under action of acid, and a compound (D0) (hereinafter, also referred to as a "component (D0)") represented by General Formula (d0).

In a case where a resist film is formed using such a resist composition and the formed resist film is subjected to selective exposure, an acid is generated at the exposed portion of the resist film, and the generated acid acts on the component (A) to change the solubility of the component (A) in a developing solution, whereas the solubility of the component (A) in a developing solution is not changed at the unexposed portion, thereby that generates the difference in solubility in the developing solution between the exposed portion and the unexposed portion of the resist film. Therefore, by subjecting the resist film to development, the exposed portion of the resist film is dissolved and removed to form a positive-tone resist pattern in a case where the resist composition is a positive-tone type, whereas the unexposed portion of the resist film is dissolved and removed to form a negative-tone resist pattern in a case where the resist composition is a negative-tone type.

In the present specification, a resist composition which forms a positive-tone resist pattern by dissolving and removing the exposed portion of the resist film is called a positive-tone resist composition, and a resist composition which forms a negative-tone resist pattern by dissolving and removing the unexposed portion of the resist film is called a negative-tone resist composition. The resist composition according to the present aspect may be a positive-tone resist composition or a negative-tone resist composition.

Further, in the formation of a resist pattern, the resist composition of the present aspect can be applied to an alkali developing process using an alkali developing solution in the developing treatment, or a solvent developing process using a developing solution containing an organic solvent (organic developing solution) in the developing treatment.

The resist composition of the present aspect has a function of generating an acid upon light exposure, the component (A) may generate an acid upon light exposure, and an additive component that is separately blended from the component (A) may generate an acid upon light exposure.

Specifically, the resist composition of the present aspect may be;
(1) a resist composition containing an acid generator component (B) (hereinafter referred to as a "component (B)") that generates an acid upon exposure,
(2) a resist composition in which the component (A) is a component that generates an acid upon exposure, or
(3) a resist composition in which the component (A) is a component that generates an acid upon exposure and which further contains the component (B).

That is, in the cases of (2) and (3) described above, the component (A) becomes a "base material component which generates an acid upon exposure and has a solubility in a developing solution, which is changed by an action of an acid". In a case where the component (A) is a base material component which generates an acid upon exposure and has solubility in a developing solution, which is changed by action of an acid, it is preferable that the component (A1) described below be a polymer compound which generates an acid upon exposure and has solubility in a developing solution, which is changed by action of an acid. As such a polymer compound, a resin having a constitutional unit that generates an acid upon exposure can be used. As the constitutional unit that generates an acid upon exposure, a known constitutional unit can be used.

Among them described above, the resist composition of the present aspect is particularly preferably the case of (1) above, that is, the embodiment in which the component (A), the component (D0), and the component (B) (provided that the component (D0) is excluded) are contained.

<Component (A)>

In the resist composition according to the present embodiment, the component (A) preferably contains a resin component (A1) (hereinafter, also referred to as a "component (A1)") exhibiting changed solubility in a developing solution under action of acid. In the alkali developing process and the solvent developing process, since the polarity of the base material component before and after the exposure is changed by using the component (A1), an excellent development contrast can be obtained.

As the component (A), at least the component (A1) is used, and another polymer compound and/or a low-molecular-weight compound may be used in combination with the component (A1).

In a case of applying an alkali developing process, a base material component containing the component (A1) is substantially insoluble in an alkali developing solution prior to exposure, and, for example, in a case where an acid is generated from the component (B) upon exposure, the action of this acid causes an increase in the polarity of the base material component, thereby increasing the solubility of the base material component in an alkali developing solution. Therefore, in the formation of a resist pattern, in a case where a resist film formed by applying the resist composition onto a support is subjected to the selective exposure, the exposed portion of the resist film changes from an insoluble state to a soluble state in an alkali developing solution, whereas the unexposed portion of the resist film remains insoluble in an alkali developing solution, and thus, a positive-tone resist pattern is formed by alkali developing.

On the other hand, in a case of a solvent developing process, the base material component containing the component (A1) exhibits high solubility in an organic developing solution prior to exposure, and, for example, in a case where an acid is generated from the component (B) upon exposure, polarity is increased by the action of the generated acid, thereby decreasing the solubility in an organic developing solution. Therefore, in the formation of a resist pattern, in a case where a resist film formed by applying the resist composition onto a support is subjected to the selective exposure, the exposed portion of the resist film changes from a soluble state to an insoluble state in an organic developing solution, whereas the unexposed portion of the resist film remains soluble and does not change, thereby a contrast between the exposed portion and the unexposed portion can be obtained, and thus a negative-tone resist pattern is formed by developing in the organic developing solution.

In the resist composition according to the present embodiment, the component (A) may be used alone or in a combination of two or more kinds thereof.

In Regard to Component (A1)

The component (A1) is a resin component exhibiting changed solubility in a developing solution under action of acid.

The component (A1) preferably has a constitutional unit (a1) that includes an acid-decomposable group having a polarity which is increased by action of acid.

The component (A1) may have other constitutional units as necessary in addition to the constitutional unit (a1).

<<Constitutional Unit (a1)>>

The constitutional unit (a1) is a constitutional unit that contains an acid-decomposable group having a polarity which is increased by action of an acid.

Examples of the acid-dissociable group are the same as those which have been proposed as acid-dissociable groups for the base resin for a chemical amplification-type resist composition.

Specific examples of acid-dissociable groups of the base resin proposed for a chemical amplification-type resist composition contains an "acetal-type acid-dissociable group", a "tertiary alkyl ester-type acid-dissociable group", and a "tertiary alkyloxycarbonyl acid-dissociable group" described below.

Acetal-Type Acid-Dissociable Group:

Examples of the acid-dissociable group for protecting a carboxy group or a hydroxyl group as a polar group include the acid-dissociable group represented by General Formula (a1-r-1) shown below (hereinafter, also referred to as an "acetal-type acid-dissociable group").

[Chemical Formula 3]

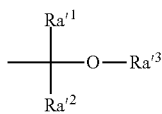

(a1-r-1)

[In the formula, $Ra'^1$ to $Ra'^2$ represent hydrogen atoms or alkyl groups. $Ra'^3$ represents a hydrocarbon group, and $Ra'^3$ may be bonded to $Ra'^1$ or $Ra'^2$ to form a ring.]

In General Formula (a1-r-1), it is preferable that at least one of $Ra'^1$ and $Ra'^2$ represent a hydrogen atom and more preferable that both $Ra'^1$ and $Ra'^2$ represent hydrogen atoms.

In a case where $Ra'^1$ or $Ra'^2$ represents an alkyl group, examples of the alkyl group include the same alkyl group as that mentioned as the substituent which may be bonded to the carbon atom at the α-position in the description on the α-substituted acrylic acid ester, and the alkyl group preferably has 1 to 5 carbon atoms. Specific examples thereof preferably include a linear or branched alkyl group. More specific examples thereof include a methyl group, an ethyl group, a propyl group, an isopropyl group, an n-butyl group, an isobutyl group, a tert-butyl group, a pentyl group, an isopentyl group, and a neopentyl group. Among these, a methyl group or an ethyl group is preferable, and a methyl group is particularly preferable.

In General Formula (a1-r-1), examples of the hydrocarbon group as $Ra'^3$ include a linear or branched alkyl group and a cyclic hydrocarbon group.

The linear alkyl group has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group has preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group. Among these, an isopropyl group is preferable.

In a case where $Ra'^3$ represents a cyclic hydrocarbon group, the cyclic hydrocarbon group may be an aliphatic hydrocarbon group or an aromatic hydrocarbon group and may be a polycyclic group or a monocyclic group.

The aliphatic hydrocarbon group which is a monocyclic group is preferably a group in which one hydrogen atom has been removed from a monocycloalkane. The monocycloalkane preferably has 3 to 6 carbon atoms, and specific examples thereof include cyclopentane and cyclohexane.

The aliphatic hydrocarbon group which is a polycyclic group is preferably a group in which one hydrogen atom has been removed from a polycycloalkane. The polycycloalkane preferably has 7 to 12 carbon atoms, and specific examples thereof include adamantane, norbornane, isobornane, tricyclodecane, and tetracyclododecane.

In a case where the cyclic hydrocarbon group as $Ra'^3$ is an aromatic hydrocarbon group, the aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms.

Specific examples of the aromatic ring include aromatic hydrocarbon rings such as benzene, naphthalene, anthracene, and phenanthrene; and an aromatic heterocyclic ring in which a part of carbon atoms constituting the above-described aromatic hydrocarbon ring have been substituted with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group as $Ra^{t3}$ include a group in which one hydrogen atom has been removed from the above-described aromatic hydrocarbon ring or aromatic heterocyclic ring (an aryl group or a heteroaryl group); a group in which one hydrogen atom has been removed from an aromatic compound having two or more aromatic rings (biphenyl, fluorene or the like); and a group in which one hydrogen atom of the above-described aromatic hydrocarbon ring or aromatic heterocyclic ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group). The alkylene group bonded to the aromatic hydrocarbon ring or aromatic heterocyclic ring preferably has 1 to 4 carbon atoms, more preferably 1 or 2 carbon atoms, and particularly preferably 1 carbon atom.

The cyclic hydrocarbon group as $Ra^{t3}$ may have a substituent. Examples of the substituent include, $-R^{P1}$, $-R^{P2}-O-R^{P1}$, $-R^{P2}-CO-R^{P1}$, $-R^{P2}-CO-OR^{P1}$, $-R^{P2}-O-CO-R^{P1}$, $-R^{P2}-OH$, $-R^{P2}-CN$, and $-R^{P2}-COOH$ (hereinafter, these substituents are also collectively referred to as "$Ra^{x5}$").

Here, $R^{P1}$ represents a monovalent chain-like saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. In addition, $R^{P2}$ represents a single bond, a divalent chain-like saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms. However, part or all of hydrogen atoms included in the chain-like saturated hydrocarbon group, the aliphatic cyclic saturated hydrocarbon group, and the aromatic hydrocarbon group of $R^{P1}$ and $R^{P2}$ may be substituted with a fluorine atom. In the aliphatic cyclic hydrocarbon group, one or more of the above-described substituents may be included as a single kind, or one or more of the above-described substituents may be included as a plurality of kinds.

Examples of the monovalent chain-like saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.02,6]decanyl group, a tricyclo [3.3.1.13,7]decanyl group, a tetracyclo [6.2.1.13,6.02,7] dodecanyl group, and an adamantyl group.

Examples of the monovalent aromatic hydrocarbon group having 6 to 30 carbon atoms include a group in which one hydrogen atom has been removed from an aromatic hydrocarbon ring such as benzene, biphenyl, fluorene, naphthalene, anthracene, or phenanthrene.

In a case where $Ra^{t3}$ is bonded to $Ra^{t1}$ or $Ra^{t2}$ to form a ring, the cyclic group is preferably a 4- to 7-membered ring, and more preferably a 4- to 6-membered ring. Specific examples of the cyclic group include a tetrahydropyranyl group and a tetrahydrofuranyl group.

Tertiary Alkyl Ester-Type Acid-Dissociable Group:

Among the above polar groups, examples of the acid-dissociable group for protecting the carboxy group include the acid-dissociable group represented by General Formula (a1-r-2) shown below.

Among the acid-dissociable groups represented by General Formula (a1-r-2), for convenience, a group which is constituted of alkyl groups is referred to as a "tertiary alkyl ester-type acid-dissociable group".

[Chemical Formula 4]

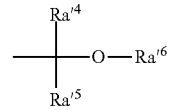

(a1-r-2)

[In the formula, $Ra^{t4}$ to $Ra^{t6}$ each represents a hydrocarbon group, and $Ra^{t5}$ and $Ra^{t6}$ may be bonded to each other to form a ring.]

Examples of the hydrocarbon group as $Ra^{t4}$ include a linear or branched alkyl group, a chain-like or cyclic alkenyl group, and a cyclic hydrocarbon group.

Examples of the linear or branched alkyl group and the cyclic hydrocarbon group (the aliphatic hydrocarbon group which is a monocyclic group, the aliphatic hydrocarbon group which is a polycyclic group, or the aromatic hydrocarbon group) as $Ra^{t4}$ include the same groups as $Ra^{t3}$ described above.

The chain-like or cyclic alkenyl group as $Ra^{t4}$ is preferably an alkenyl group having 2 to 10 carbon atoms.

Examples of the hydrocarbon group as $Ra^{t5}$ or $Ra^{t6}$ include the same group as $Ra^{t3}$ described above.

In a case where $Ra^{t5}$ to $Ra^{t6}$ are bonded to each other to form a ring, groups represented by General Formula (a1-r2-1), General Formula (a1-r2-2), and General Formula (a1-r2-3) can be suitably mentioned.

On the other hand, in a case where $Ra^{t4}$ to $Ra^{t6}$ are not bonded to each other and represent an independent hydrocarbon group, a group represented by General Formula (a1-r2-4) can be suitably mentioned.

[Chemical Formula 5]

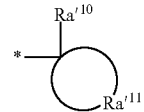

(a1-r2-1)

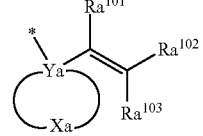

(a1-r2-2)

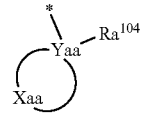

(a1-r2-3)

(a1-r2-4)

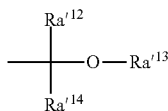

[In General Formula (a1-r2-1), $Ra'^{10}$ represents a linear or branched alkyl group having 1 to 12 carbon atoms, a part of which may be substituted with a halogen atom or a hetero atom-containing group. $Ra'^{11}$ represents a group that forms an aliphatic cyclic group together with a carbon atom to which $Ra'^{10}$ is bonded. In General Formula (a1-r2-2), Ya represents a carbon atom. Xa is a group that forms a cyclic hydrocarbon group together with Ya. Part or all of the hydrogen atoms which the cyclic hydrocarbon group has may be substituted. $Ra^{101}$ to $Ra^{103}$ each independently represents a hydrogen atom, a monovalent chain-like saturated hydrocarbon group having 1 to 10 carbon atoms, or a monovalent aliphatic cyclic saturated hydrocarbon group having 3 to 20 carbon atoms. Part or all of the hydrogen atoms which the chain-like saturated hydrocarbon group and the aliphatic cyclic saturated hydrocarbon group have may be substituted. Two or more of $Ra^{101}$ to $Ra^{103}$ may be bonded to each other to form a cyclic structure. In General Formula (a1-r2-3), Yaa represents a carbon atom. Xaa is a group that forms an aliphatic cyclic group together with Yaa. $Ra^{104}$ represents an aromatic hydrocarbon group which may have a substituent. In General Formula (a1-r2-4), $Ra'^{12}$ and $Ra'^{13}$ each independently represent a monovalent chain-like saturated hydrocarbon group having 1 to 10 carbon atoms or a hydrogen atom. Part or all of the hydrogen atoms which the chain-like saturated hydrocarbon group has may be substituted. $Ra'^{14}$ represents a hydrocarbon group which may have a substituent. * represents a bonding site.]

In General Formula (a1-r2-1), $Ra'^{10}$ represents a linear or branched alkyl group having 1 to 12 carbon atoms, a part of which may be substituted with a halogen atom or a hetero atom-containing group.

The linear alkyl group as $Ra'^{10}$ has 1 to 12 carbon atoms, and preferably has 1 to 10 carbon atoms and particularly preferably 1 to 5 carbon atoms.

Examples of the branched alkyl group as $Ra'^{10}$ include the same group as $Ra'^{3}$.

A part of the alkyl group as $Ra'^{10}$ may be substituted with a halogen atom or a hetero atom-containing group. For example, a part of the hydrogen atoms constituting the alkyl group may be substituted with a halogen atom or a hetero atom-containing group. Further, a part of carbon atoms (such as methylene group) constituting the alkyl group may be substituted with a hetero atom-containing group.

Examples of the hetero atom mentioned here include an oxygen atom, a sulfur atom, and a nitrogen atom. Examples of the hetero atom-containing group include (—O—), —C(=O)—O—, —O—C(=O)—, —C(=O)—, —O—C(=O)—O—, —C(=O)—NH—, —NH—, —S—, —S(=O)$_2$—, and —S(=O)$_2$—O—.

In General Formula (a1-r2-1), $Ra'^{11}$ (a group that forms an aliphatic cyclic group together with a carbon atom to which $Ra'^{10}$ is bonded) is preferably the group mentioned as the aliphatic hydrocarbon group (the alicyclic hydrocarbon group) which is a monocyclic group or a polycyclic group as $Ra'^{3}$ in General Formula (a1-r-1). Among them, a monocyclic alicyclic hydrocarbon group is preferable, specifically, a cyclopentyl group or a cyclohexyl group is more preferable, and a cyclopentyl group is still more preferable.

In General Formula (a1-r2-2), examples of the cyclic hydrocarbon group formed by Xa together with Ya include a group in which one or more hydrogen atoms are further removed from a cyclic monovalent hydrocarbon group (an aliphatic hydrocarbon group) as $Ra'^{3}$ in General Formula (a1-r-1).

The cyclic hydrocarbon group which is formed by Xa together with Ya may have a substituent. Examples of this substituent include the same group as the substituent which the cyclic hydrocarbon group as $Ra'^{3}$ may have.

In General Formula (a1-r2-2), as $Ra^{101}$ to $Ra^{103}$, examples of the monovalent chain-like saturated hydrocarbon group having 1 to 10 carbon atoms include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms, as $Ra^{101}$ to $Ra^{103}$, include monocyclic aliphatic saturated hydrocarbon groups such as a cyclopropyl group, a cyclobutyl group, a cyclopentyl group, a cyclohexyl group, a cycloheptyl group, a cyclooctyl group, a cyclodecyl group, and cyclododecyl group; and polycyclic aliphatic saturated hydrocarbon groups such as a bicyclo[2.2.2]octanyl group, a tricyclo[5.2.1.02,6]decanyl group, a tricyclo[3.3.1.13,7]decanyl group, a tetracyclo[6.2.1.13,6.02,7] dodecanyl group, and an adamantyl group.

Among them, $Ra^{101}$ to $Ra^{103}$ are preferably a hydrogen atom or a monovalent chain-like saturated hydrocarbon group having 1 to 10 carbon atoms, and among them, a hydrogen atom, a methyl group, and an ethyl group are more preferable, and a hydrogen atom is particularly preferable from the viewpoint of easy synthesis.

Examples of the substituent which the chain-like saturated hydrocarbon group represented by $Ra^{101}$ to $Ra^{103}$ or the aliphatic cyclic saturated hydrocarbon group has include the same groups as $Ra^{x5}$ described above.

Examples of the group containing a carbon-carbon double bond generated by forming a cyclic structure, in which two or more of $Ra^{101}$ to $Ra^{103}$ are bonded to each other, include a cyclopentenyl group, a cyclohexenyl group, a methylcyclopentenyl group, a methylcyclohexenyl group, a cyclopentylideneethenyl group, and a cyclohexylideneethenyl group. Among these, a cyclopentenyl group, a cyclohexenyl group, and a cyclopentylideneethenyl group are preferable from the viewpoint of easy synthesis.

In General Formula (a1-r2-3), an aliphatic cyclic group that is formed by Xaa together with Yaa is preferably the group mentioned as the aliphatic hydrocarbon group which is a monocyclic group or a polycyclic group as $Ra'^{3}$ in General Formula (a1-r-1).

In General Formula (a1-r2-3), Examples of the aromatic hydrocarbon group as $Ra^{104}$ include a group in which one or more hydrogen atoms have been removed from an aromatic hydrocarbon ring having 5 to 30 carbon atoms. Among them, $Ra^{104}$ is preferably a group in which one or more hydrogen atoms have been removed from an aromatic hydrocarbon ring having 6 to 15 carbon atoms, more preferably a group in which one or more hydrogen atoms have been removed from benzene, naphthalene, anthracene, or phenanthrene, still more preferably a group in which one or more hydrogen atoms have been removed from benzene, naphthalene, or anthracene, particularly preferably a group in which one or more hydrogen atoms have been removed from benzene or naphthalene, and most preferably a group in which one or more hydrogen atoms have been removed from benzene.

Examples of the substituent which $Ra^{104}$ in General Formula (a1-r2-3) may have include a methyl group, an ethyl group, propyl group, a hydroxy group, a carboxy group, a halogen atom, an alkoxy group (a methoxy group, an ethoxy group, a propoxy group, a butoxy group, and the like), and an alkyloxycarbonyl group.

In General Formula (a1-r2-4), $Ra'^{12}$ and $Ra'^{13}$ each independently represent a monovalent chain-like saturated hydrocarbon group having 1 to 10 carbon atoms or a hydrogen atom. Examples of the monovalent chain-like saturated hydrocarbon group having 1 to 10 carbon atoms as $Ra'^{12}$ and $Ra'^{13}$ include the same monovalent chain-like saturated hydrocarbon groups as those having 1 to 10 carbon atoms as $Ra^{101}$ to $Ra^{103}$ as described above. Part or all of the hydrogen atoms which the chain-like saturated hydrocarbon group has may be substituted.

Among them, $Ra'^{12}$ and $Ra'^{13}$ are preferably a hydrogen atom or an alkyl group having 1 to 5 carbon atoms, more preferably an alkyl group having 1 to 5 carbon atoms, still more preferably a methyl group or an ethyl group, and particularly preferably a methyl group.

In a case where the chain-like saturated hydrocarbon groups represented by $Ra'^{12}$ and $Ra'^{13}$ are substituted, examples of the substituent include the same group as $Ra^{x5}$ described above.

In Formula (a1-r2-4), $Ra'^{14}$ represents a hydrocarbon group which may have a substituent. Examples of the hydrocarbon group as $Ra'^{14}$ include a linear or branched alkyl group and a cyclic hydrocarbon group.

The linear alkyl group as $Ra'^{14}$ has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group as $Ra'^{14}$ has preferably 3 to 10 carbon atoms and more preferably 3 to 5 carbon atoms. Specific examples thereof include an isopropyl group, an isobutyl group, a tert-butyl group, an isopentyl group, a neopentyl group a 1,1-diethylpropyl group, and a 2,2-dimethylbutyl group. Among these, an isopropyl group is preferable.

In a case where $Ra'^{14}$ represents a cyclic hydrocarbon group, the cyclic hydrocarbon group may be an aliphatic hydrocarbon group or an aromatic hydrocarbon group and may be a polycyclic group or a monocyclic group.

The aliphatic hydrocarbon group which is a monocyclic group is preferably a group in which one hydrogen atom has been removed from a monocycloalkane. The monocycloalkane preferably has 3 to 6 carbon atoms, and specific examples thereof include cyclopentane and cyclohexane.

The aliphatic hydrocarbon group which is a polycyclic group is preferably a group in which one hydrogen atom has been removed from a polycycloalkane. The polycycloalkane preferably has 7 to 12 carbon atoms, and specific examples thereof include adamantane, norbornane, isobornane, tricyclodecane, and tetracyclododecane.

Examples of the aromatic hydrocarbon group as $Ra'^{14}$ include the same group as the aromatic hydrocarbon group as $Ra^{104}$. Among them, $Ra'^{14}$ is preferably a group in which one or more hydrogen atoms have been removed from an aromatic hydrocarbon ring having 6 to 15 carbon atoms, more preferably a group in which one or more hydrogen atoms have been removed from benzene, naphthalene, anthracene, or phenanthrene, still more preferably a group in which one or more hydrogen atoms have been removed from benzene, naphthalene, or anthracene, particularly preferably a group in which one or more hydrogen atoms have been removed from naphthalene or anthracene, and most preferably a group in which one or more hydrogen atoms have been removed from naphthalene.

Examples of the substituent which $Ra'^{14}$ may have include the same group as the substituent which $Ra^{104}$ may have.

In a case where $Ra'^{14}$ in General Formula (a1-r2-4) is a naphthyl group, the position at which the tertiary carbon atom in General Formula (a1-r2-4) is bonded is any of the 1-position and the 2-position of the naphthyl group.

In a case where $Ra'^{14}$ in Formula (a1-r2-4) is an anthryl group, the position at which the tertiary carbon atom in Formula (a1-r2-4) is bonded is any of the 1-position, the 2-position, and 9-position of the anthryl group.

Specific examples of the group represented by General Formula (a1-r2-1) are shown below.

[Chemical Formula 6]

(r-pr-m1)

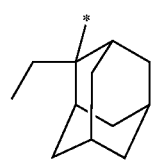

(r-pr-m2)

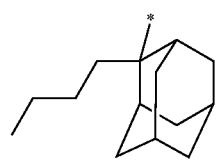

(r-pr-m3)

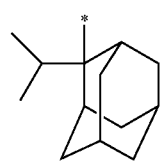

(r-pr-m4)

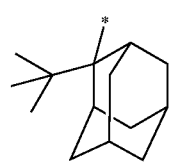

(r-pr-m5)

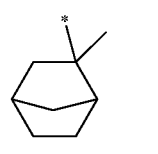

(r-pr-m6)

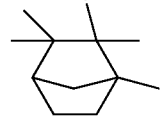

(r-pr-m7)

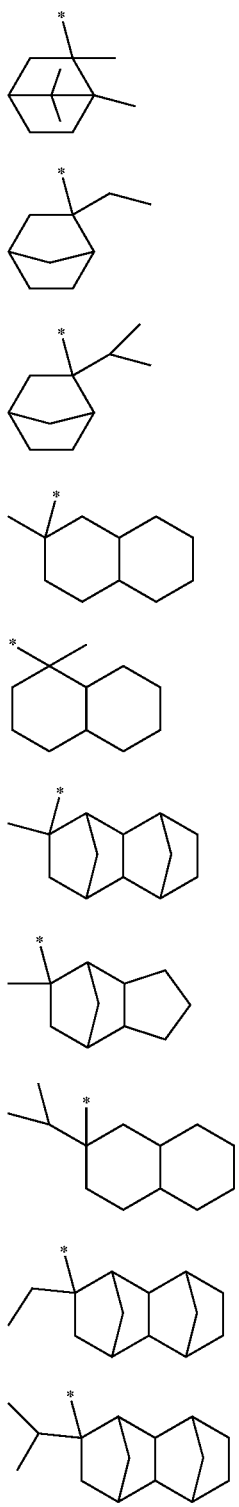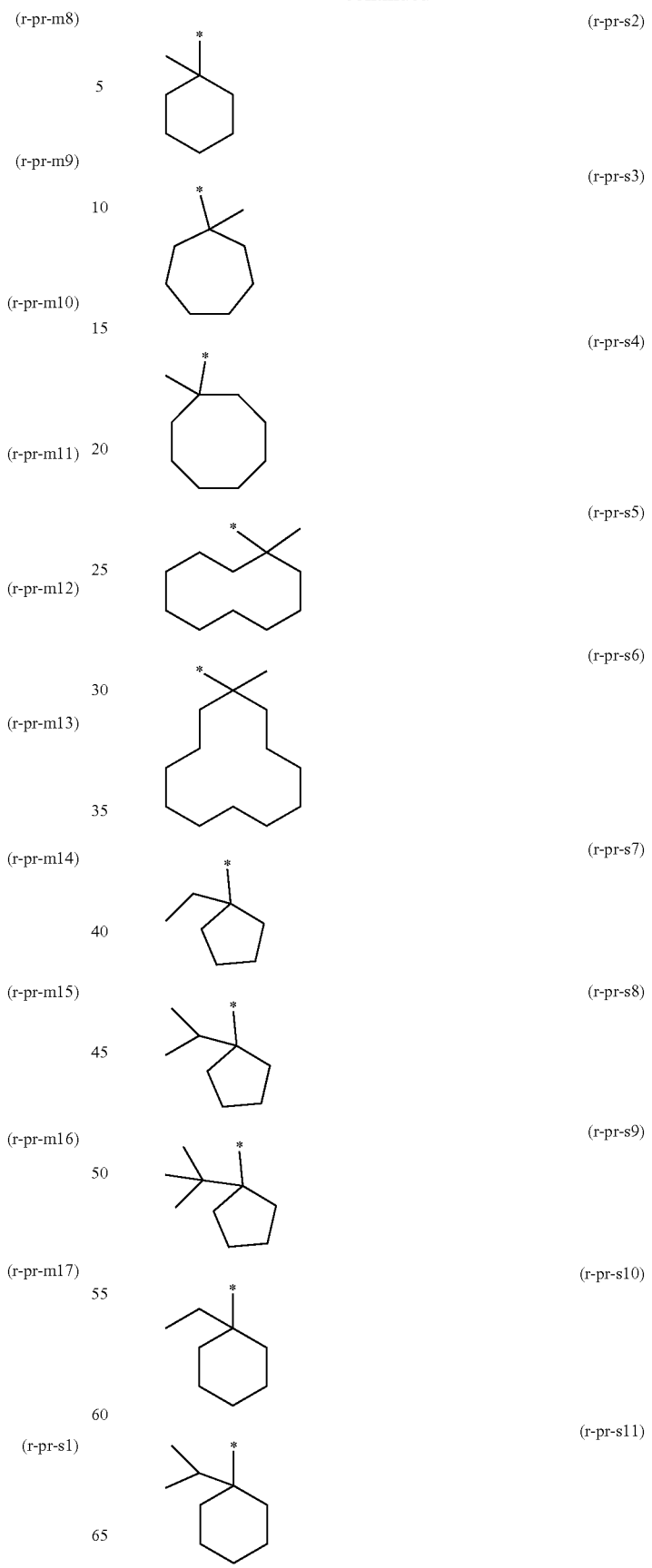
[Chemical Formula 7]

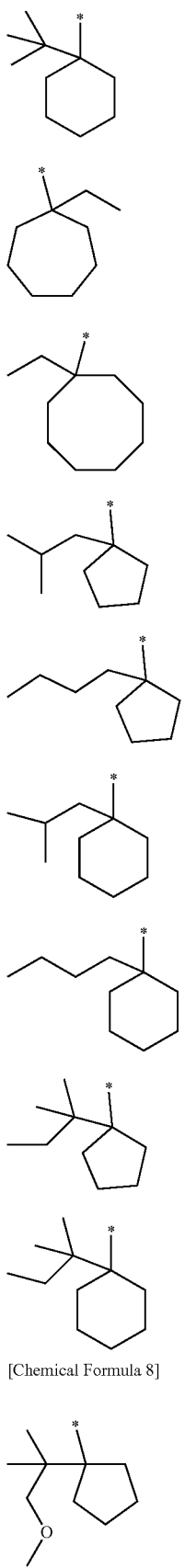
[Chemical Formula 8]
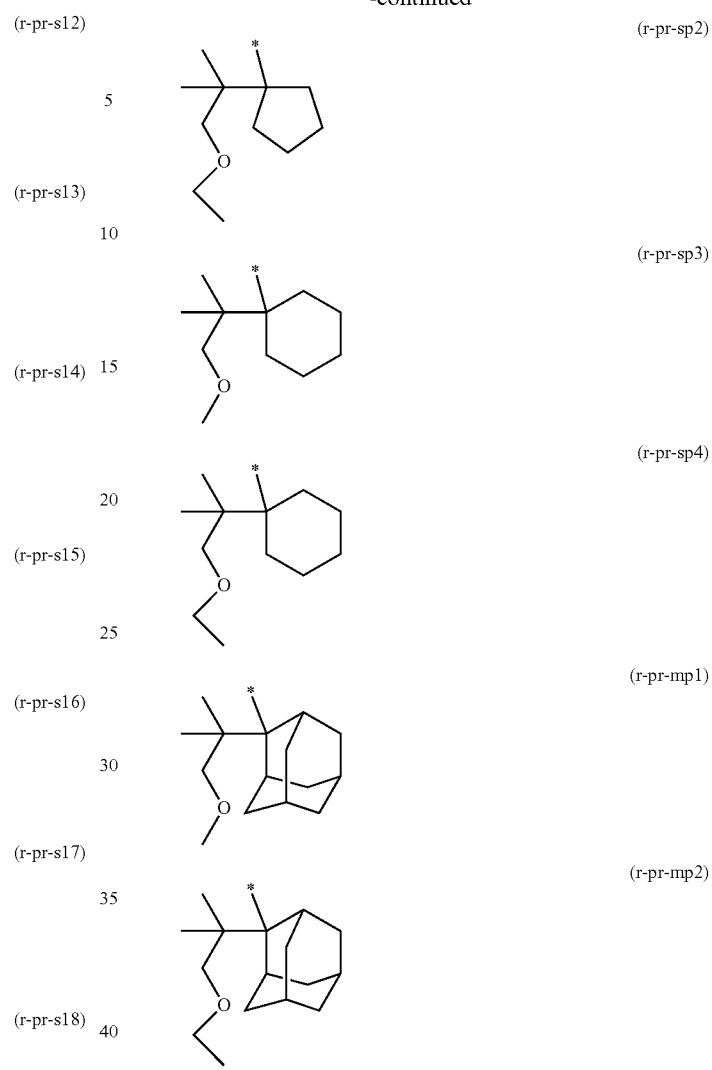
Specific examples of the group represented by General Formula (a1-r2-2) are shown below.
[Chemical Formula 9]
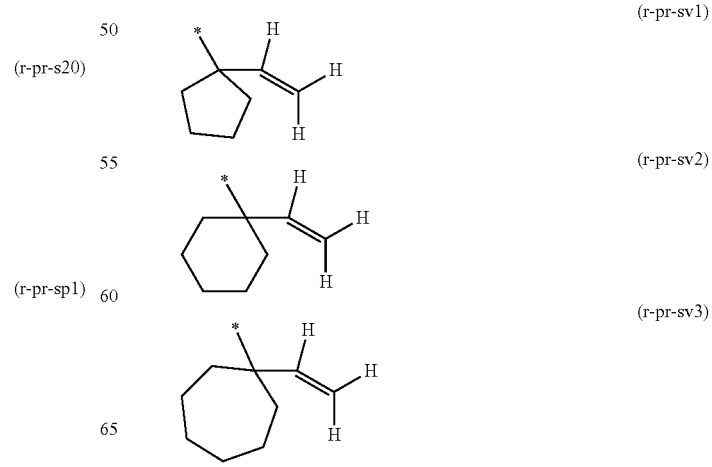

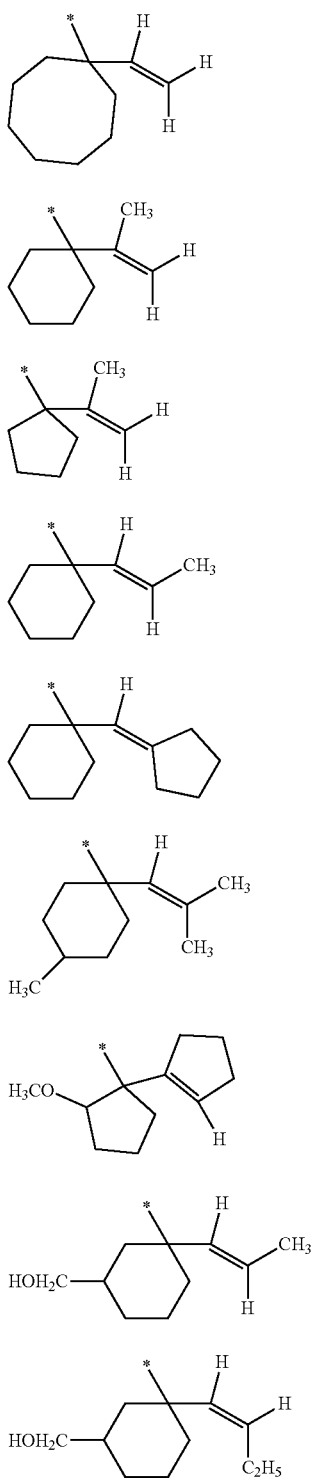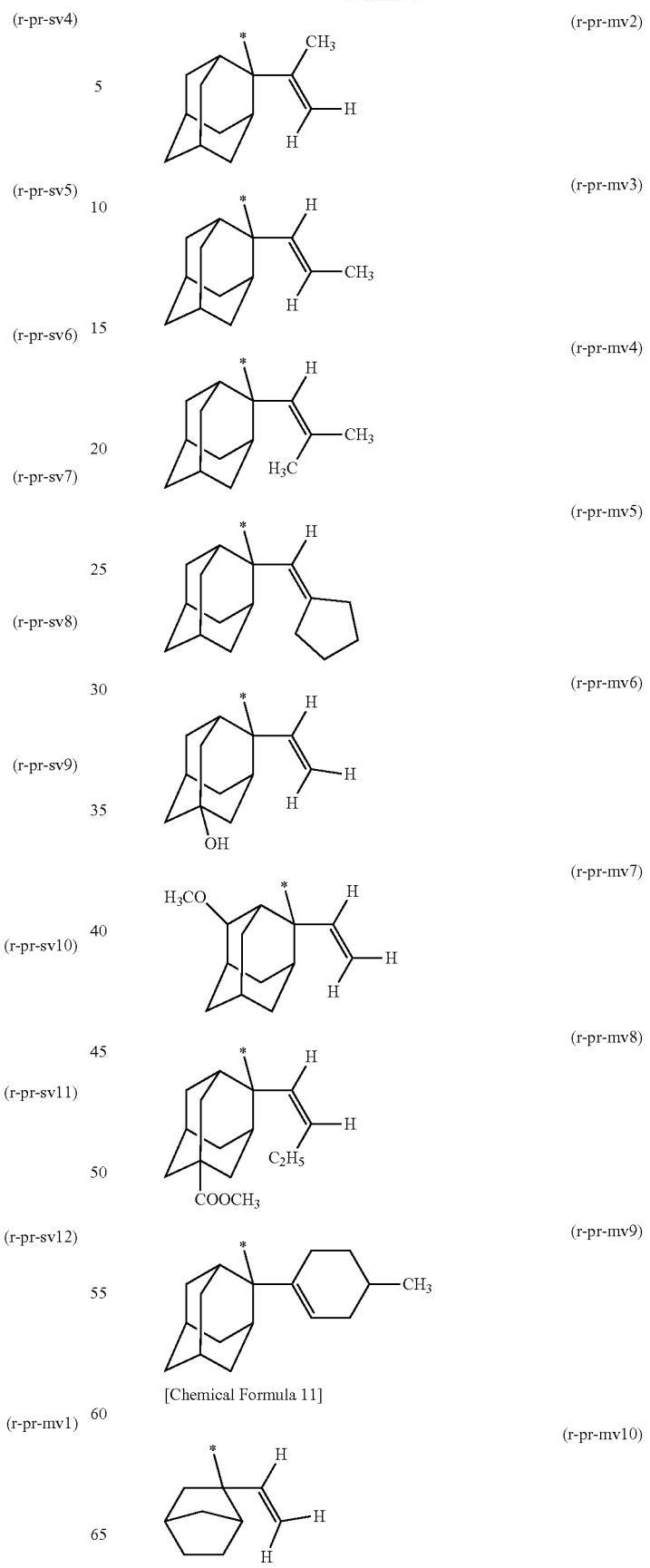

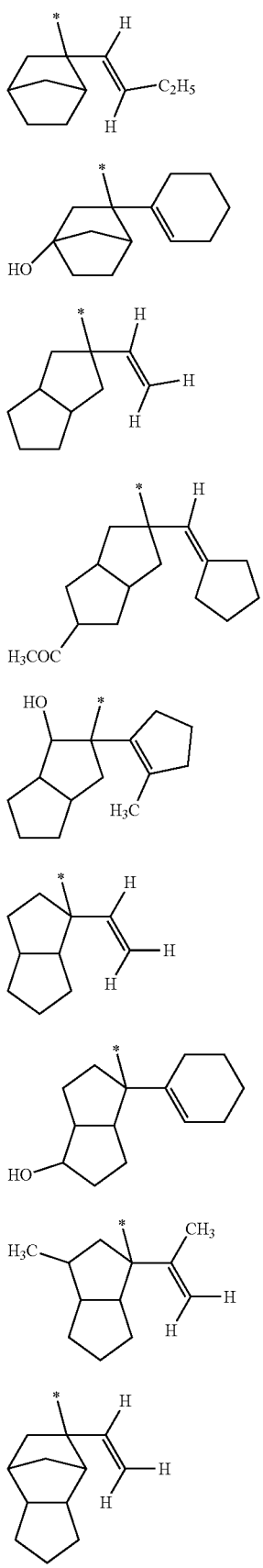
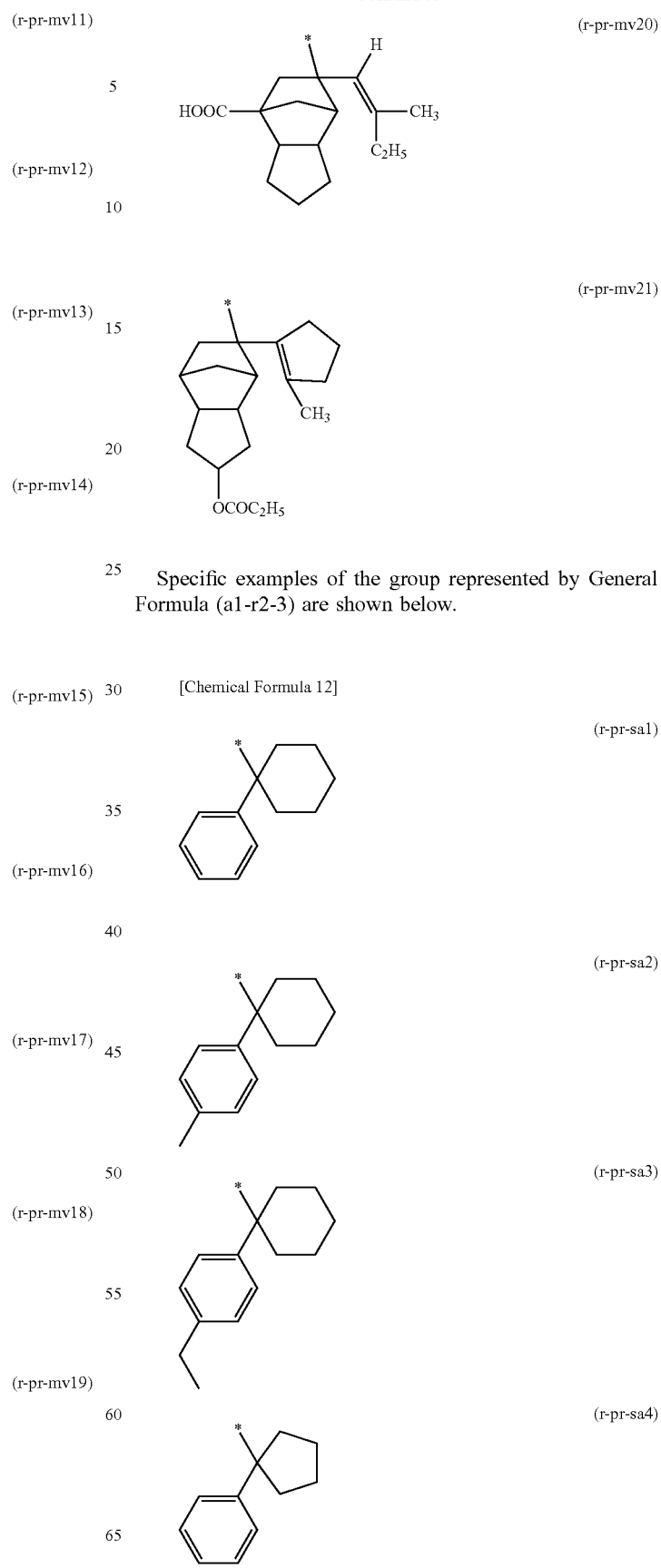
Specific examples of the group represented by General Formula (a1-r2-3) are shown below.
[Chemical Formula 12]

-continued
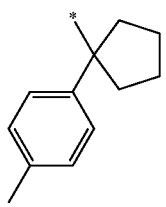 (r-pr-sa5)
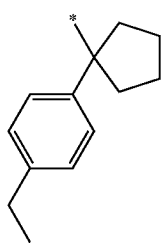 (r-pr-sa6)
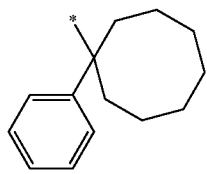 (r-pr-sa7)
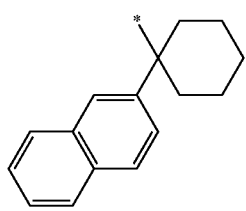 (r-pr-sa8)
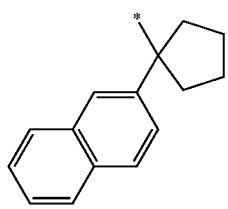 (r-pr-sa9)
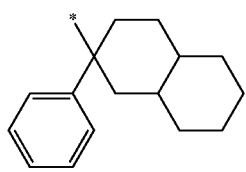 (r-pr-ma1)
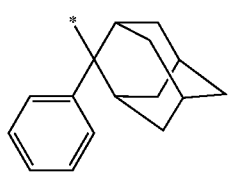 (r-pr-ma2)
[Chemical Formula 13]
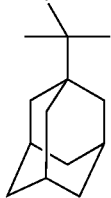 (r-pr-cm1)
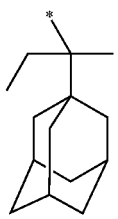 (r-pr-cm2)
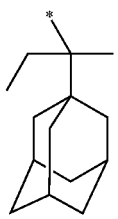 (r-pr-cm3)
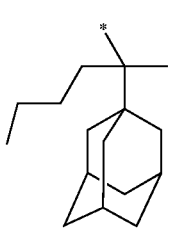 (r-pr-cm4)
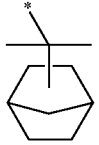 (r-pr-cm5)
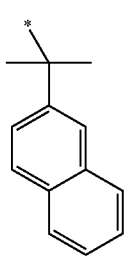 (r-pr-cm5)
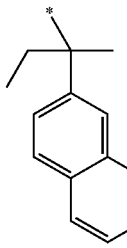 (r-pr-cm6)
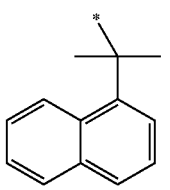 (r-pr-cm7)
Specific examples of the group represented by General Formula (a1-r2-4) are shown below.

(r-pr-cm8)
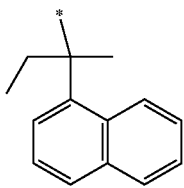

(r-pr-cs1)
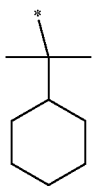

(r-pr-cs2)
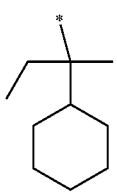

(r-pr-cs3)
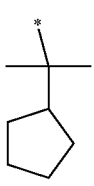

(r-pr-cs4)
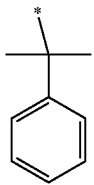

(r-pr-cs5)
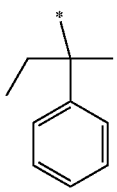

(r-pr-c1)

(r-pr-c2)
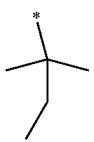

(r-pr-c3)
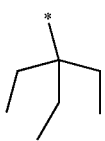

Tertiary Alkyloxycarbonyl Acid-Dissociable Group:

Among the polar groups, examples of the acid-dissociable group for protecting a hydroxyl group include an acid-dissociable group (hereinafter, for convenience, also referred to as a "tertiary alkyloxycarbonyl acid-dissociable group") represented by General Formula (a1-r-3) shown below.

[Chemical Formula 14]

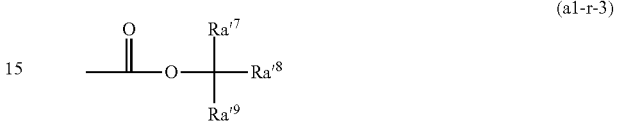

(a1-r-3)

[In the formula, $Ra'^7$ to $Ra'^9$ each represents an alkyl group.]

In General Formula (a1-r-3), $Ra'^7$ to $Ra'^9$ are each preferably an alkyl group having 1 to 5 carbon atoms and more preferably an alkyl group having 1 to 3 carbon atoms.

Further, the total number of carbon atoms in each of the alkyl groups is preferably in a range of 3 to 7, more preferably in a range of 3 to 5, and most preferably 3 or 4.

Examples of the constitutional unit (a1) include a constitutional unit derived from acrylic acid ester in which the hydrogen atom bonded to the carbon atom at the α-position may be substituted with a substituent; a constitutional unit derived from acrylamide; a constitutional unit in which at least a part of hydrogen atoms in a hydroxyl group of a constitutional unit derived from hydroxystyrene or a hydroxystyrene derivative are protected by the substituent including an acid-decomposable group; and a constitutional unit in which at least a part of hydrogen atoms in —C(=O)—OH of a constitutional unit derived from vinylbenzoic acid or a vinylbenzoic acid derivative are protected by the substituent including an acid-decomposable group.

Among the above, the constitutional unit (a1) is preferably a constitutional unit derived from acrylic acid ester in which the hydrogen atom bonded to the carbon atom at the α-position may be substituted with a substituent.

Preferred specific examples of such a constitutional unit (a1) include constitutional units represented by General Formula (a1-1) or (a1-2).

[Chemical Formula 15]

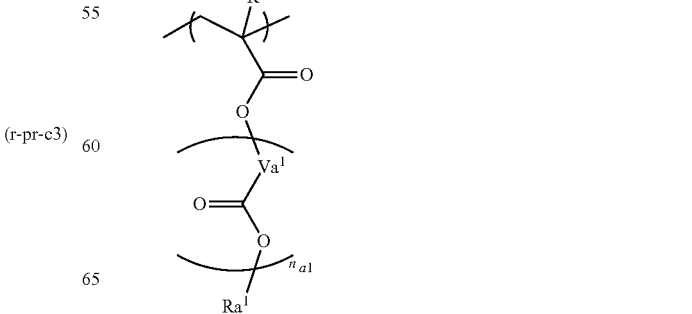

(a1-1)

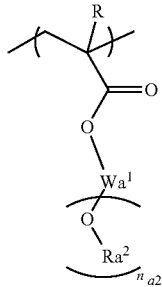

(a1-2)

[In the formula, R represents a hydrogen atom, an alkyl group having 1 to 5 carbon atoms, or a halogenated alkyl group having 1 to 5 carbon atoms. $Va^1$ represents a divalent hydrocarbon group which may have an ether bond. $n_{a1}$ represents an integer in a range of 0 to 2. $Ra^1$ is an acid-dissociable group represented by General Formula (a1-r-1) or (a1-r-2). $Wa^1$ represents an $(n_{a2}+1)$-valent hydrocarbon group, $n_{a2}$ represents an integer in a range of 1 to 3, and $Ra^2$ represents an acid-dissociable group represented by General Formula (a1-r-1) or (a1-r-3).]

In General Formula (a1-1), the alkyl group having 1 to 5 carbon atoms as R is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which part or all of hydrogen atoms in the alkyl group having 1 to 5 carbon atoms have been substituted with a halogen atom. The halogen atom is particularly preferably a fluorine atom.

As R, a hydrogen atom, an alkyl group having 1 to 5 carbon atoms, or a fluorinated alkyl group having 1 to 5 carbon atoms is preferable, and a hydrogen atom or a methyl group is most preferable in terms of industrial availability.

In General Formula (a1-1), the divalent hydrocarbon group as $Va^1$ may be an aliphatic hydrocarbon group or an aromatic hydrocarbon group.

The aliphatic hydrocarbon group as the divalent hydrocarbon group represented by $Va^1$ may be saturated or unsaturated. In general, it is preferable that the aliphatic hydrocarbon group be saturated.

Specific examples of the aliphatic hydrocarbon group include a linear or branched aliphatic hydrocarbon group, and an aliphatic hydrocarbon group containing a ring in the structure thereof.

The linear aliphatic hydrocarbon group described above preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group described above preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

Examples of the aliphatic hydrocarbon group containing a ring in the structure thereof include an alicyclic hydrocarbon group (a group in which two hydrogen atoms have been removed from an aliphatic hydrocarbon ring), a group in which the alicyclic hydrocarbon group is bonded to the terminal of the linear or branched aliphatic hydrocarbon group, and a group in which the alicyclic hydrocarbon group is interposed in the linear or branched aliphatic hydrocarbon group. The linear or branched aliphatic hydrocarbon group is the same as that defined for the above-described linear aliphatic hydrocarbon group or the above-described branched aliphatic hydrocarbon group.

The alicyclic hydrocarbon group preferably has 3 to 20 carbon atoms and more preferably 3 to 12 carbon atoms.

The alicyclic hydrocarbon group may be monocyclic or polycyclic. The monocyclic alicyclic hydrocarbon group is preferably a group in which two hydrogen atoms have been removed from a monocycloalkane. The monocycloalkane preferably has 3 to 6 carbon atoms, and specific examples thereof include cyclopentane and cyclohexane. The polycyclic alicyclic hydrocarbon group is preferably a group in which two hydrogen atoms have been removed from a polycycloalkane, and the polycycloalkane is preferably a group having 7 to 12 carbon atoms. Specific examples of the polycycloalkane include adamantane, norbornane, isobornane, tricyclodecane, and tetracyclododecane.

The aromatic hydrocarbon group as the divalent hydrocarbon group represented by $Va^1$ is a hydrocarbon group having an aromatic ring.

The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 12 carbon atoms. Here, the number of carbon atoms in a substituent is not included in the number of carbon atoms.

Specific examples of the aromatic ring which the aromatic hydrocarbon group has include aromatic hydrocarbon rings such as benzene, biphenyl, fluorene, naphthalene, anthracene, and phenanthrene; and aromatic heterocyclic rings in which a part of carbon atoms constituting the above-described aromatic hydrocarbon rings have been substituted with a hetero atom. Examples of the hetero atom in the aromatic heterocyclic rings include an oxygen atom, a sulfur atom, and a nitrogen atom.

Specific examples of the aromatic hydrocarbon group include a group in which two hydrogen atoms have been removed from the above-described aromatic hydrocarbon ring (an arylene group); and a group in which one hydrogen atom of a group (an aryl group) formed by removing one hydrogen atom from the aromatic hydrocarbon ring has been substituted with an alkylene group (a group formed by removing one more hydrogen atom from an aryl group in arylalkyl groups such as a benzyl group, a phenethyl group, a 1-naphthylmethyl group, a 2-naphthylmethyl group, a 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

In General Formula (a1-1), $Ra^1$ is an acid-dissociable group represented by General Formula (a1-r-1) or (a1-r-2).

In General Formula (a1-2), the $(n_{a2}+1)$-valent hydrocarbon group as $Wa^1$ may be an aliphatic hydrocarbon group or an aromatic hydrocarbon group. The aliphatic hydrocarbon group indicates a hydrocarbon group that has no aromaticity and may be saturated or unsaturated. In general, it is preferable that the aliphatic hydrocarbon group be saturated. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $(n_{a2}+1)$ is preferably divalent, trivalent, or tetravalent, and more preferably divalent or trivalent.

In General Formula (a1-2), $Ra^2$ is an acid-dissociable group represented by General Formula (a1-r-1) or (a1-r-3).

Specific examples of the constitutional unit represented by General Formula (a1-1) are shown below. In each of the formulae shown below, $R^\alpha$ represents a hydrogen atom, a methyl group, or a trifluoromethyl group.

[Chemical Formula 16]

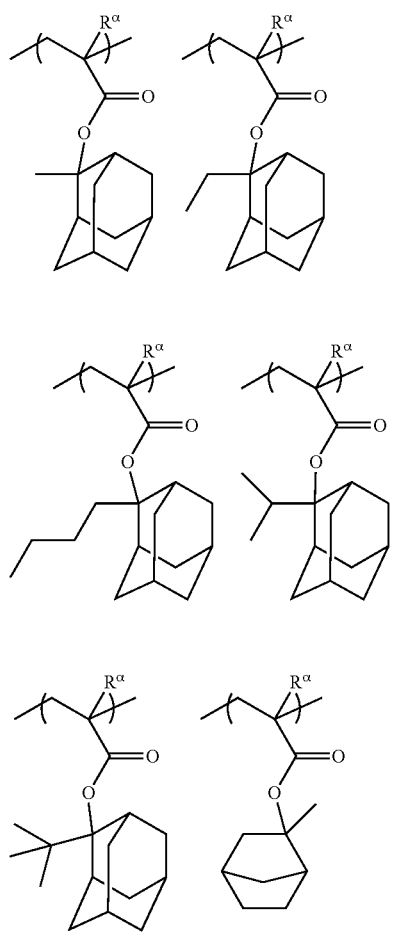

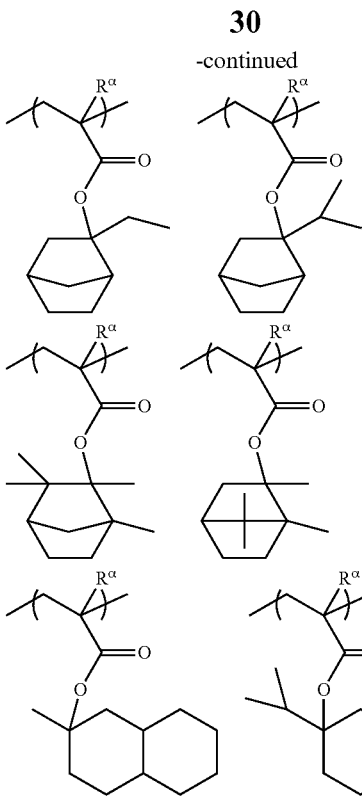

-continued

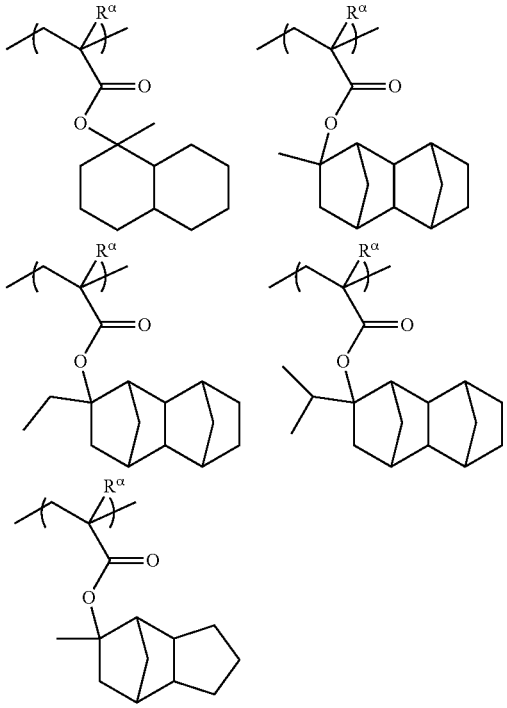

[Chemical Formula 17]

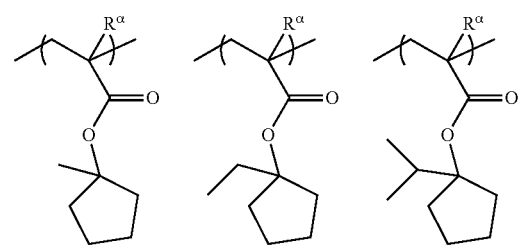

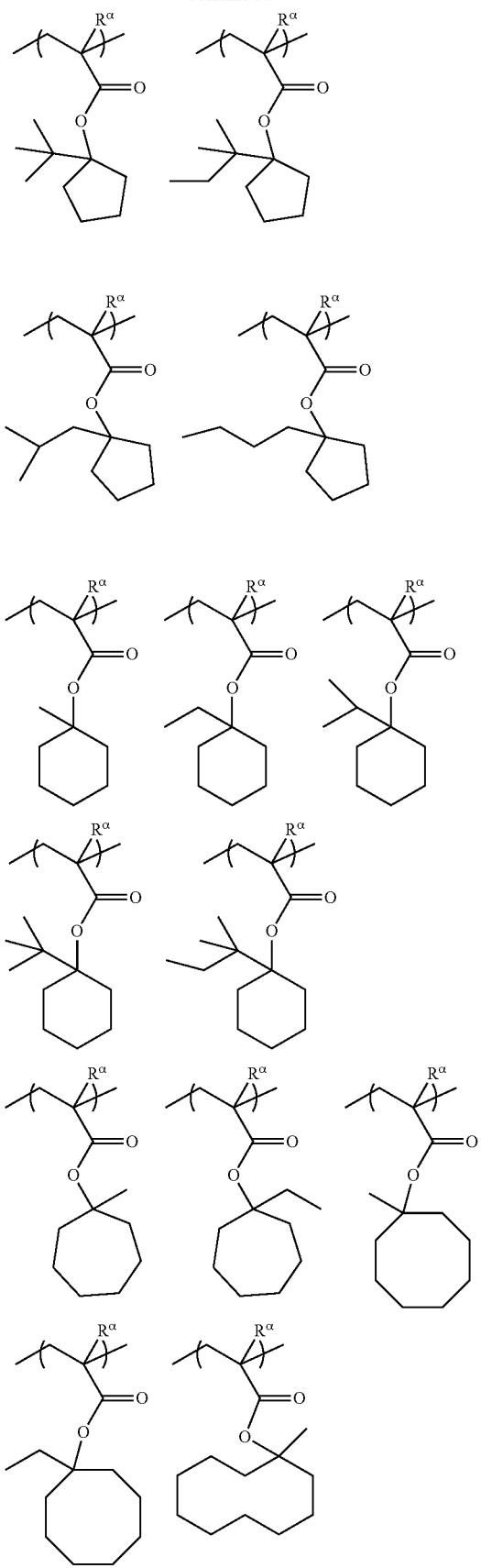
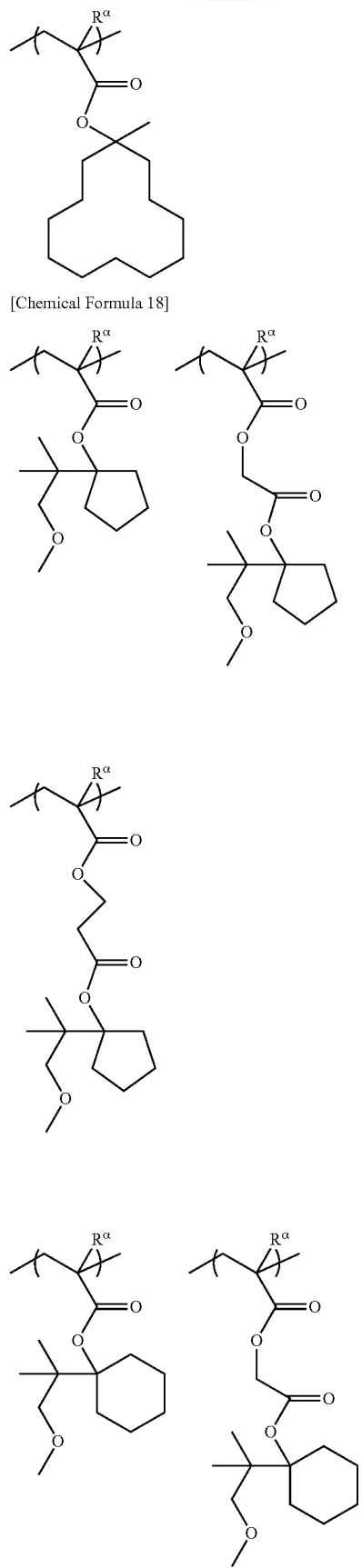
[Chemical Formula 18]

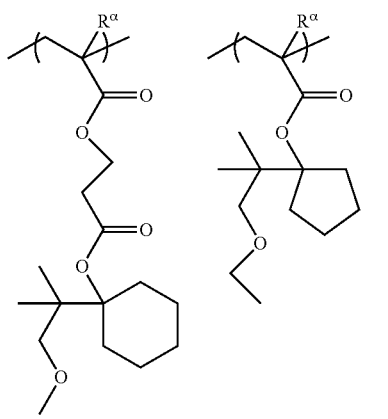
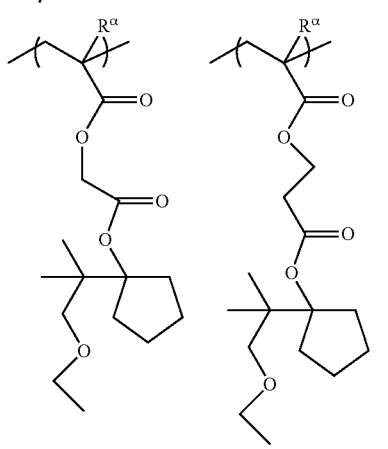
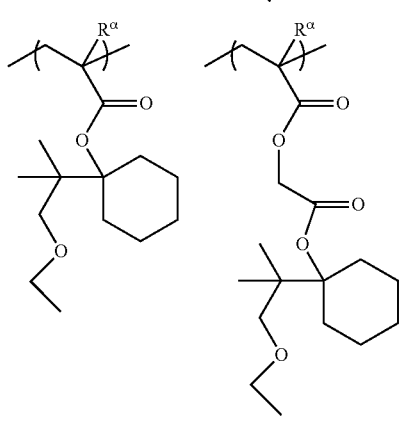
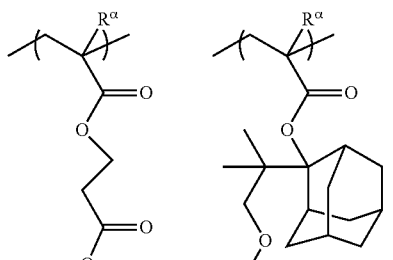
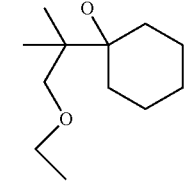
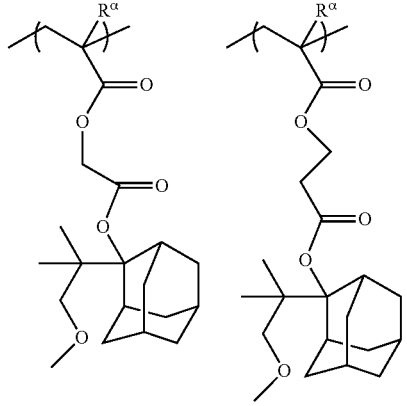
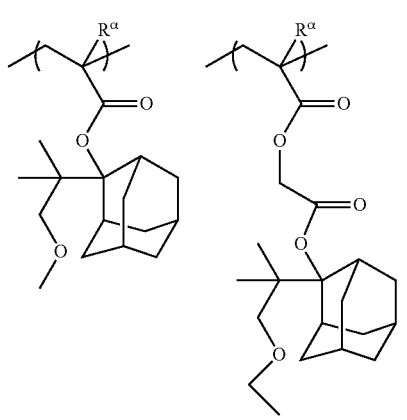
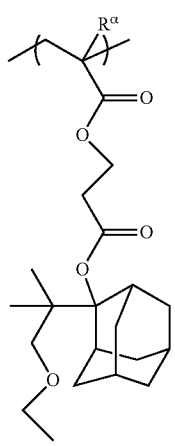
[Chemical Formula 19]
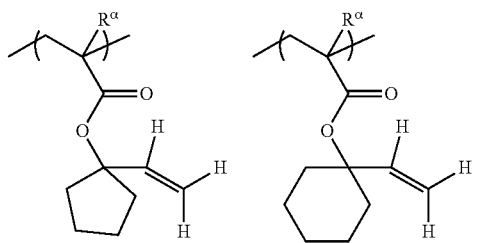

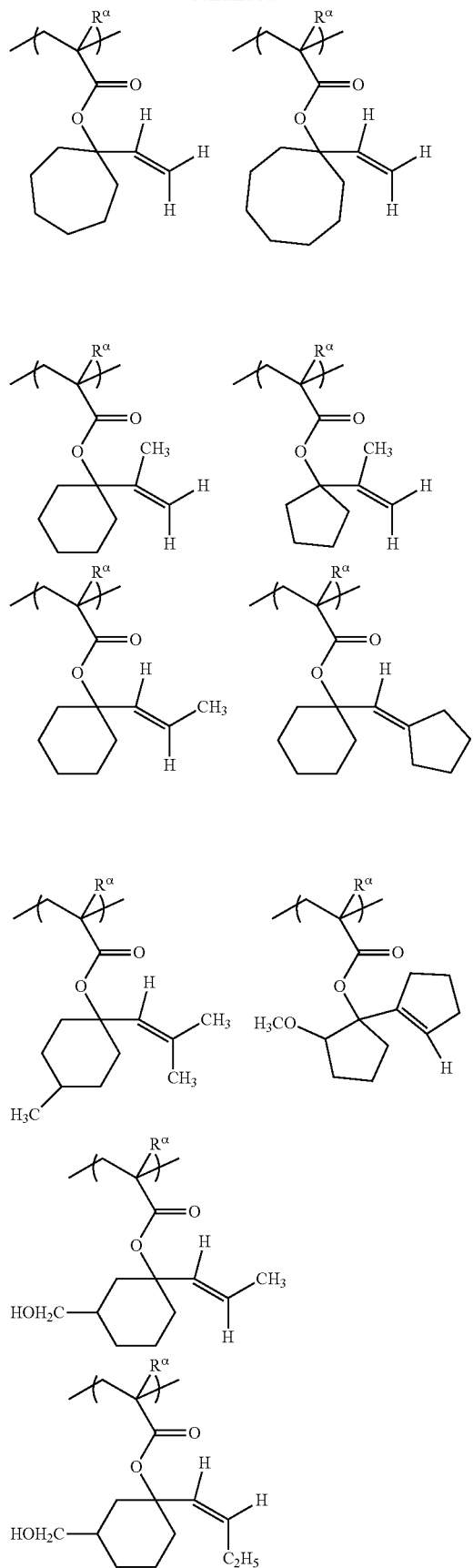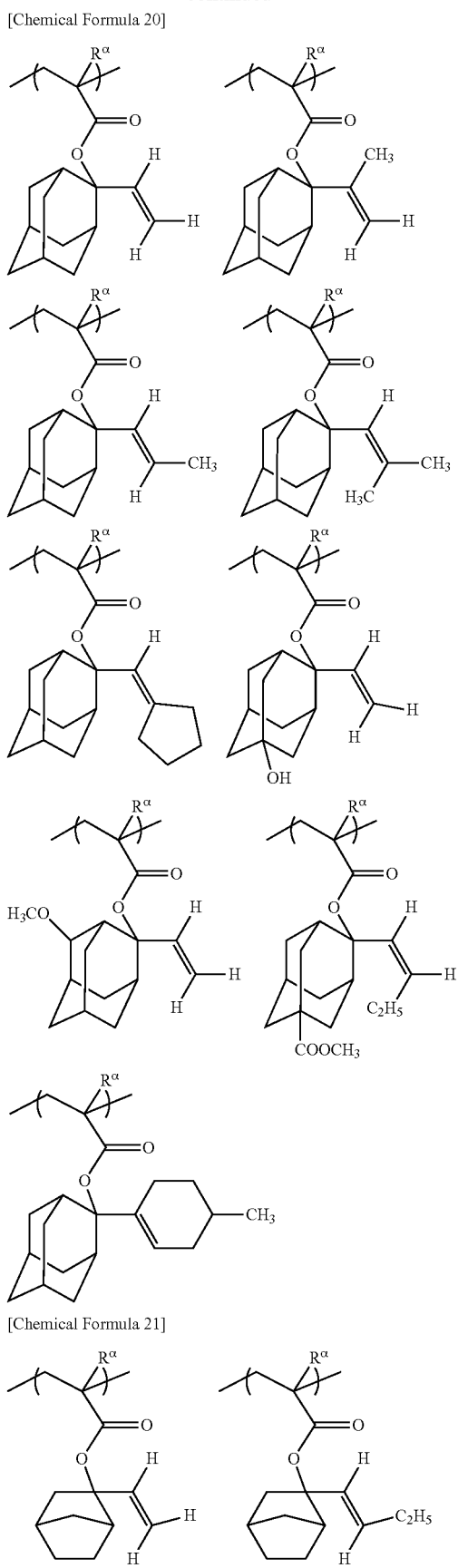

-continued
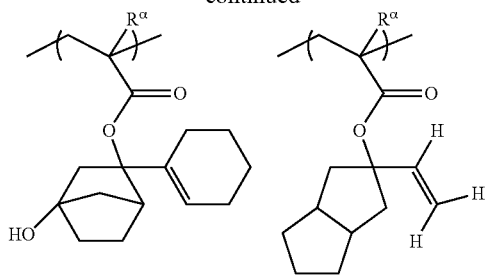
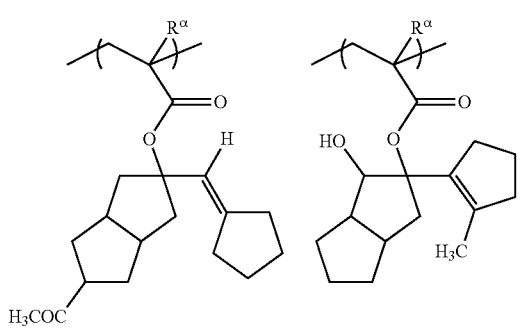
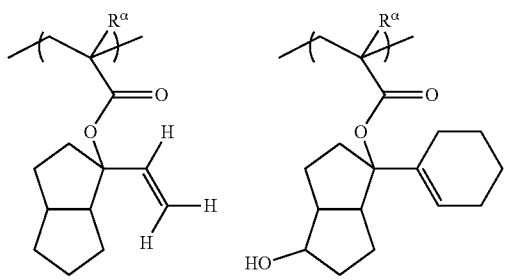
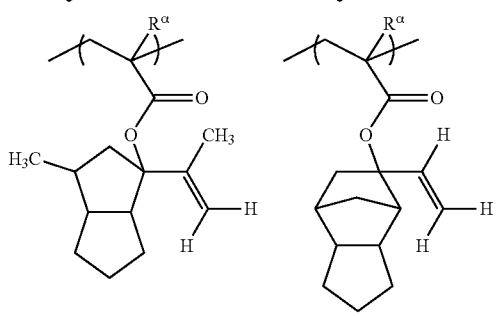
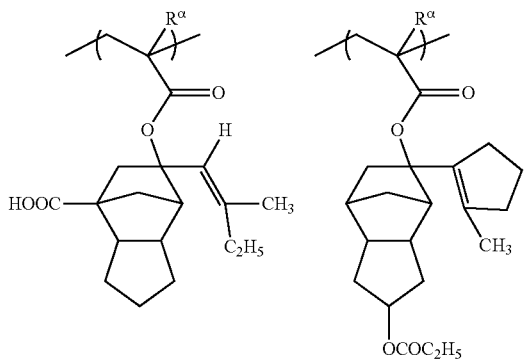
-continued
[Chemical Formula 22]
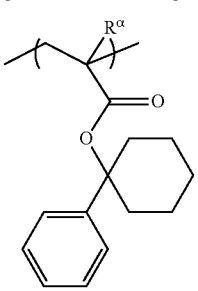
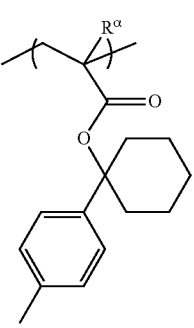
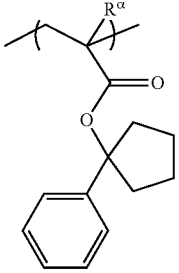
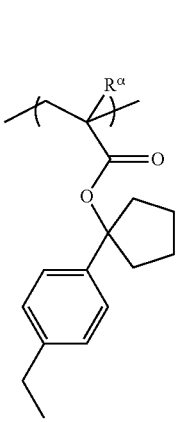
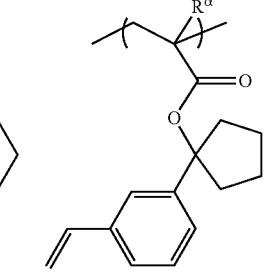
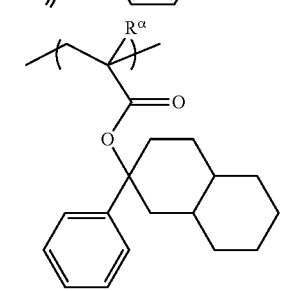

-continued

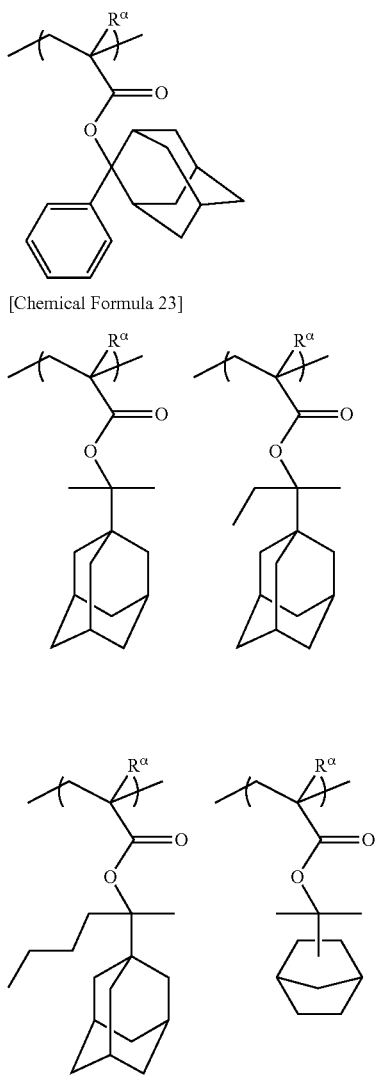

[Chemical Formula 23]

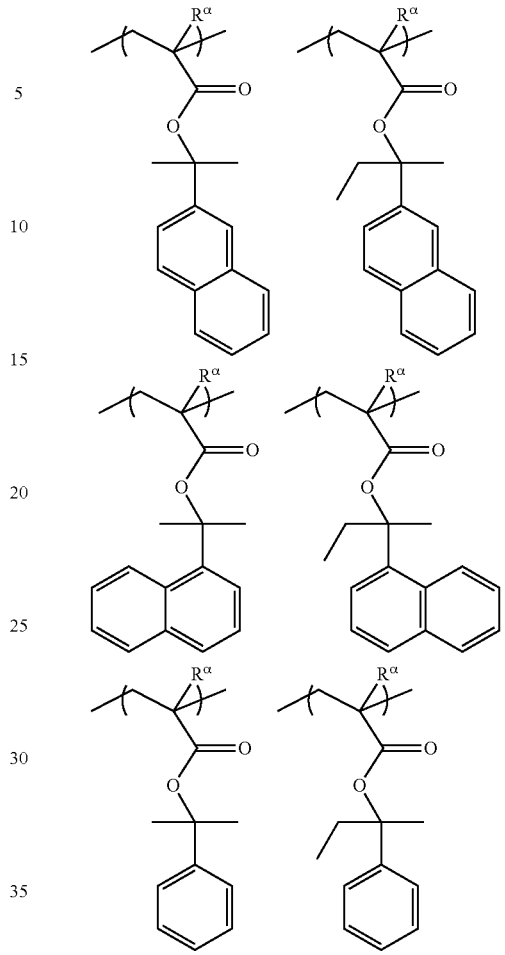

The constitutional unit (a1) which the component (A1) has may be one kind or may be two or more kinds.

The constitutional unit (a1) is more preferably a constitutional unit represented by General Formula (a1-1) since lithography characteristics (sensitivity, shape, and the like) in lithography depending on an electron beam or EUV can be more easily increased.

Among these, the constitutional unit (a1) particularly preferably includes a constitutional unit represented by General Formula (a1-1-1) shown below.

[Chemical Formula 24]

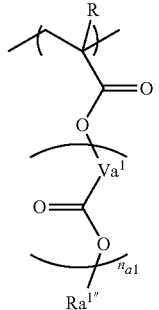

(a1-1-1)

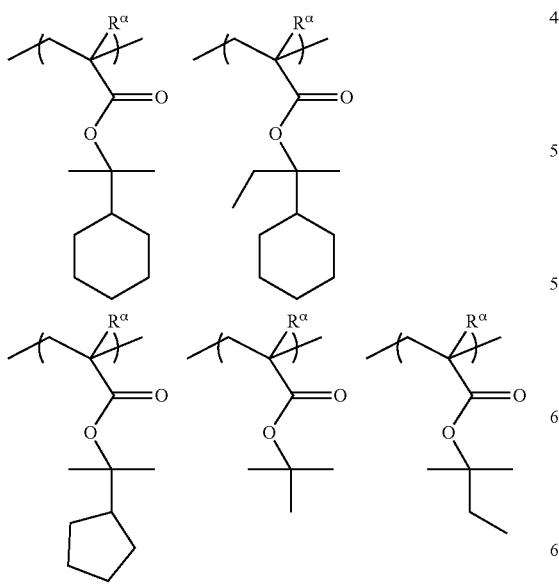

-continued

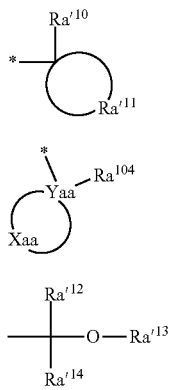

(a1-r2-1)

(a1-r2-3)

(a1-r2-4)

[In the formula, Ra' is an acid-dissociable group represented by General Formula (a1-r2-1), (a1-r2-3), or (a1-r2-4).]

In General Formula (a1-1-1), R, $Va^1$, and $n_{a1}$ are respectively the same as R, $Va^1$, and $n_{a1}$ in General Formula (a1-1).

The description for the acid-dissociable group represented by General Formula (a1-r2-1), (a1-r2-3), or (a1-r2-4) is as described above. Among them, it is preferable to select a group in which the acid-dissociable group is a cyclic group due to the fact that the reactivity can be increased, which is suitable for EB or EUV.

In General Formula (a1-1-1), $Ra^{1'''}$ is preferably, among the above, an acid-dissociable group represented by General Formula (a1-r2-1) or General Formula (a1-r2-3).

The proportion of the constitutional unit (a1) in the component (A1) is preferably in a range of 5% to 80% by mole, more preferably in a range of 10% to 75% by mole, still more preferably in a range of 30% to 70% by mole, and particularly preferably in a range of 40% to 60% by mole, with respect to the total amount (100% by mole) of all constitutional units constituting the component (A1).

In a case where the proportion of the constitutional unit (a1) is equal to or more than the lower limit value of the preferred range described above, lithography characteristics such as sensitivity, resolution, and roughness are improved. On the other hand, in a case where the proportion is equal to or lower than the upper limit value of the above-described preferred range, balance with other constitutional units can be obtained, and various lithography characteristics are improved.

<<Other Constitutional Units>>

The component (A1) may have other constitutional units as necessary in addition to the constitutional unit (a1) described above.

Examples of other constitutional units include a constitutional unit (a10) represented by General Formula (a10-1) described later; a constitutional unit (a2) containing a lactone-containing cyclic group, a —$SO_2$-containing cyclic group, or a carbonate-containing cyclic group; a constitutional unit (a3) containing a polar group-containing aliphatic hydrocarbon group; a constitutional unit (a4) containing an acid non-dissociable aliphatic cyclic group; and a constitutional unit (st) derived from styrene or a derivative thereof.

In Regard to Constitutional Unit (a10):

The constitutional unit (a10) is a constitutional unit derived from a compound represented by General Formula (a10-1).

[Chemical Formula 25]

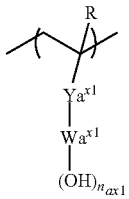

(a10-1)

[In the formula, R represents a hydrogen atom, an alkyl group having 1 to 5 carbon atoms, or a halogenated alkyl group having 1 to 5 carbon atoms. $Ya^{x1}$ represents a single bond or a divalent linking group. $Wa^{x1}$ represents an aromatic hydrocarbon group which may have a substituent. $n_{ax1}$ represents an integer of 1 or greater.]

In General Formula (a10-1), R represents a hydrogen atom, an alkyl group having 1 to 5 carbon atoms, or a halogenated alkyl group having 1 to 5 carbon atoms.

As the alkyl group having 1 to 5 carbon atoms as R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms as R is a group in which part or all of hydrogen atoms of the above-described alkyl group having 1 to 5 carbon atoms have been substituted with a halogen atom. The halogen atom is particularly preferably a fluorine atom.

R is preferably a hydrogen atom, an alkyl group having 1 to 5 carbon atoms, or a fluorinated alkyl group having 1 to 5 carbon atoms, and in terms of industrial availability, R is more preferably a hydrogen atom, a methyl group, or trifluoromethyl group, still more preferably a hydrogen atom or a methyl group, and particularly preferably a methyl group.

In General Formula (a10-1), $Ya^{x1}$ represents a single bond or a divalent linking group.

In the chemical formulae described above, the divalent linking group as $Ya^{x1}$ is not particularly limited, and suitable examples thereof include a divalent hydrocarbon group which may have a substituent and a divalent linking group having hetero atoms.

Divalent Hydrocarbon Group Which may have Substituent:

In a case where $Ya^{x1}$ represents a divalent hydrocarbon group which may have a substituent, the hydrocarbon group may be an aliphatic hydrocarbon group or an aromatic hydrocarbon group.

Aliphatic Hydrocarbon Group as $Ya^{x1}$

The aliphatic hydrocarbon group indicates a hydrocarbon group that has no aromaticity. The aliphatic hydrocarbon group may be saturated or unsaturated. In general, it is preferable that the aliphatic hydrocarbon group be saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. The alkyl group in the alkylalkylene group is preferably a linear alkyl group having 1 to 5 carbon atoms.

The linear or branched aliphatic hydrocarbon group may or may not have a substituent. Examples of the substituent include a fluorine atom, a fluorinated alkyl group having 1 to 5 carbon atoms, which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed in a linear or branched aliphatic hydrocarbon group. Examples of the linear or branched aliphatic hydrocarbon group include the same groups as those described above.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. The monocyclic alicyclic hydrocarbon group is preferably a group in which two hydrogen atoms have been removed from a monocycloalkane. The monocycloalkane preferably has 3 to 6 carbon atoms, and specific examples thereof include cyclopentane and cyclohexane. The polycyclic alicyclic hydrocarbon group is preferably a group in which two hydrogen atoms have been removed from a polycycloalkane, and the polycycloalkane is preferably a group having 7 to 12 carbon atoms. Specific examples of the polycyclic alicyclic hydrocarbon group include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and still more preferably a methoxy group or an ethoxy group.

Examples of the halogen atom for the substituent include a fluorine atom, a chlorine atom, a bromine atom, and an iodine atom, and a fluorine atom is preferable.

Examples of the halogenated alkyl group as the substituent include groups in which part or all of hydrogen atoms in the above-described alkyl groups have been substituted with the above-described halogen atoms.

In the cyclic aliphatic hydrocarbon group, a part of carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group as $Ya^{x1}$

An aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms.

Specific examples of the aromatic ring include aromatic hydrocarbon rings such as benzene, naphthalene, anthracene, and phenanthrene; and an aromatic heterocyclic ring in which a part of carbon atoms constituting the above-described aromatic hydrocarbon ring have been substituted with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group in which two hydrogen atoms have been removed from the above-described aromatic hydrocarbon ring or aromatic heterocyclic ring (an arylene group or a heteroarylene group); a group in which two hydrogen atoms have been removed from an aromatic compound having two or more aromatic rings (such as biphenyl or fluorene); and a group in which one hydrogen atom of a group (an aryl group or a heteroaryl group) in which one hydrogen atoms has been removed from the above-described aromatic hydrocarbon ring or aromatic heterocyclic ring has been substituted with an alkylene group (for example, a group in which one hydrogen atom has been further removed from an aryl group in arylalkyl groups such as a benzyl group, a phenethyl group, a 1-naphthylmethyl group, a 2-naphthylmethyl group, a 1-naphthylethyl group, or a 2-naphthylethyl group). The alkylene group bonded to the aryl group or the heteroaryl group preferably has 1 to 4 carbon atoms, more preferably 1 or 2 carbon atoms, and particularly preferably 1 carbon atoms.

With respect to the aromatic hydrocarbon group, the hydrogen atom which the aromatic hydrocarbon group has may be substituted with a substituent. For example, the hydrogen atom bonded to the aromatic ring in the aromatic hydrocarbon group may be substituted with a substituent.

Examples of substituents include an alkyl group, an alkoxy group, a halogen atom, a halogenated alkyl group, and a hydroxyl group.

The alkyl group as the substituent is preferably an alkyl group having 1 to 5 carbon atoms, and a methyl group, an ethyl group, a propyl group, an n-butyl group, or a tert-butyl group is most preferable.

Examples of the alkoxy group, the halogen atom, and the halogenated alkyl group, as the substituent, include the same groups as those exemplified as the substituent that is substituted for a hydrogen atom which the cyclic aliphatic hydrocarbon group has.

Divalent Linking Group Containing Hetero Atom

In a case where $Ya^{x1}$ represents a divalent linking group containing a hetero atom, preferred examples of the linking group include —O—, —C(=O)—O—, —O—C(=O)—, —C(=O)—, —O—C(=O)—O—, —C(=O)—NH—, —NH—, —NH—C(=NH)— (H may be substituted with a substituent such as an alkyl group, an acyl group, or the like), —S—, —S(=O)$_2$—, —S(=O)$_2$—O—, and a group represented by General Formula —Y$^{21}$—O—Y$^{22}$—, —Y$^{21}$—O—, —Y$^{21}$—C(=O)—O—, —C(=O)—O—Y$^{21}$—, —[Y$^{21}$—C(=)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represent a divalent hydrocarbon group which may have a substituent, O represents an oxygen atom, and m" represents an integer in a range of 0 to 3].

In a case where the divalent linking group containing a hetero atom is —C(=O)—NH—, —C(=O)—NH—C(=O)—, —NH—, or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and most preferably 1 to 5 carbon atoms.

In General Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$—, and —Y$^{21}$—S(=O)$_2$—O—Y$^{22}$—, Y$^{21}$, and Y$^{22}$ each independently represent a divalent hydrocarbon group which may have a substituent. Examples of the divalent hydrocarbon group include the same groups as those (described as the divalent hydrocarbon group which may have a substituent) described in the description of the above-described divalent linking group as $Ya^{x1}$.

Y$^{21}$ is preferably a linear aliphatic hydrocarbon group, more preferably a linear alkylene group, still more preferably a linear alkylene group having 1 to 5 carbon atoms, and particularly preferably a methylene group or an ethylene group.

Y$^{22}$ is preferably a linear or branched aliphatic hydrocarbon group and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by Formula —[Y$^{21}$—C(=O)—O]$_{m''}$—Y$^{22}$—, m" represents an integer in a range of 0 to 3, preferably an integer in a range of 0 to 2, more preferably 0 or 1, and particularly preferably 1. In other words, it is particularly preferable that the group represented by Formula —[Y$^{21}$—C(=O)—O]$_{m''}$—Y$^{22}$— represent a group represented by Formula —Y$^{21}$—C(=O)—O—Y$^{22}$—. Among these, a group represented by Formula —(CH$_2$)$_{a'}$—C(=O)—O—(CH$_2$)$_{b'}$— is preferable. In the formula, a' represents an integer in a range of 1 to 10, preferably an integer in a range of 1 to 8, more preferably an integer in a range of 1 to 5, still more preferably 1 or 2, and most preferably 1. b' represents an integer in a range of 1 to 10, preferably an integer in a range of 1 to 8, more preferably an integer in a range of 1 to 5, still more preferably 1 or 2, and most preferably 1.

Among the above, $Ya^{x1}$ is preferably a single bond, an ester bond [—C(=O)—O—, —O—C(=O)—], an ether bond (—O—), a linear or branched alkylene group, or a combination thereof, and more preferably a single bond or an ester bond [—C(=O)—O—, —O—C(=O)—].

In General Formula (a10-1), $Wa^{x1}$ represents an aromatic hydrocarbon group which may have a substituent.

Examples of the aromatic hydrocarbon group as $Wa^{x1}$ include a group in which $(n_{ax1}+1)$ hydrogen atoms have been removed from an aromatic ring which may have a substituent. The aromatic ring is not particularly limited as long as it is a cyclic conjugated system having $(4n+2)$ $\pi$ electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and aromatic heterocyclic rings in which a part of carbon atoms constituting the above-described aromatic hydrocarbon rings have been substituted with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Examples of the aromatic hydrocarbon group as $Wa^{x1}$ also include a group in which $(n_{ax1}+1)$ hydrogen atoms have been removed from an aromatic compound including an aromatic ring (for example, biphenyl and fluorene) which may have two or more substituents.

Among the above, $Wa^{x1}$ is preferably a group in which $(n_{ax1}+1)$ hydrogen atoms have been removed from benzene, naphthalene, anthracene, or biphenyl, more preferably a group in which $(n_{ax1}+1)$ hydrogen atoms have been removed from benzene or naphthalene, and still more preferably a group in which $(n_{ax1}+1)$ hydrogen atoms have been removed from benzene.

The aromatic hydrocarbon group as $Wa^{x1}$ may or may not have a substituent. Examples of the substituent include an alkyl group, an alkoxy group, a halogen atom, and a halogenated alkyl group. Examples of the alkyl groups, the alkoxy groups, the halogen atoms, and the halogenated alkyl groups as the substituent include the same groups which are mentioned as the above-described substituents of the cyclic aliphatic hydrocarbon group as $Ya^{x1}$. The substituent is preferably a linear or branched alkyl group having 1 to 5 carbon atoms, more preferably a linear or branched alkyl group having 1 to 3 carbon atoms, still more preferably an ethyl group or a methyl group, and particularly preferably a methyl group. The aromatic hydrocarbon group as $Wa^{x1}$ preferably has no substituent.

In General Formula (a10-1), $n_{ax1}$ represents an integer of 1 or greater, preferably an integer in a range of 1 to 10, more preferably an integer in a range of 1 to 5, still more preferably 1, 2, or 3, and particularly preferably 1 or 2.

Specific examples of the constitutional unit (a10) represented by General Formula (a10-1) are shown below.

In the formulae shown below, $R^\alpha$ represents a hydrogen atom, a methyl group, or a trifluoromethyl group.

[Chemical Formula 26]
(a10-1-11)
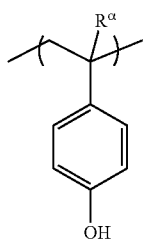
(a10-1-12)
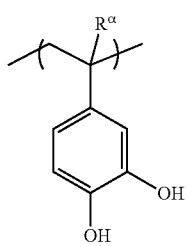
(a10-1-13)
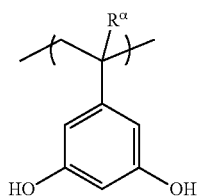
(a10-1-14)
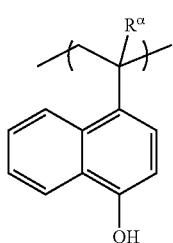
(a10-1-15)
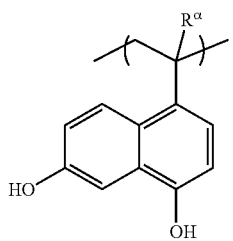
(a10-1-16)
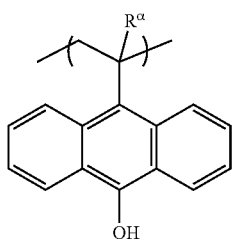
(a10-1-17)
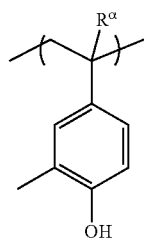
(a10-1-18)
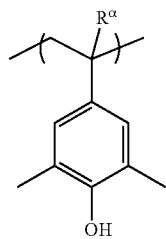
[Chemical Formula 27]
(a10-1-21)
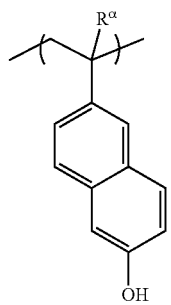
(a10-1-22)
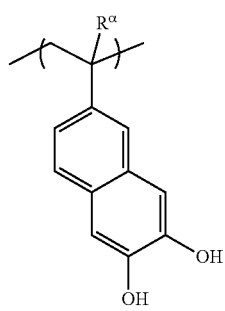
(a10-1-23)
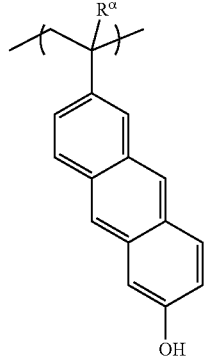

-continued
(a10-1-24)
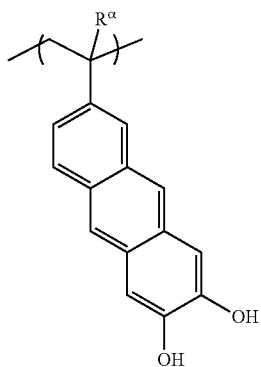
[Chemical Formula 28]
(a10-1-31)
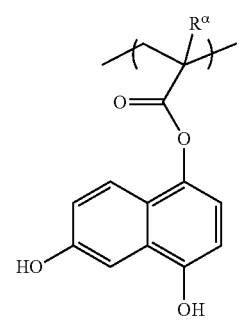
(a10-1-32)
(a10-1-33)
(a10-1-34)
(a10-1-35)
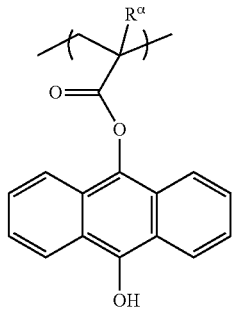
(a10-1-36)
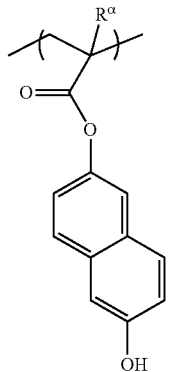
[Chemical Formula 29]
(a10-1-41)
(a10-1-42)
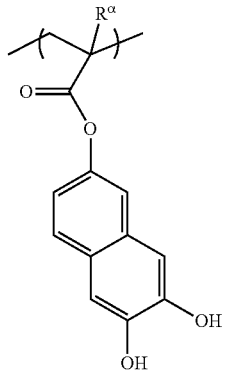

-continued (a10-1-43)
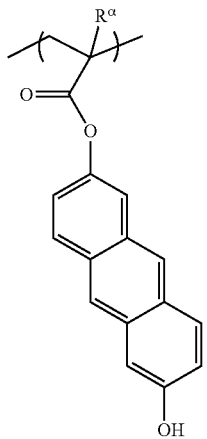

(a10-1-44)
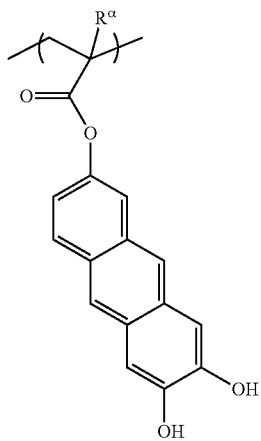

The constitutional unit (a10) which the component (A1) has may be one kind or may be two or more kinds.

In a case where the component (A1) has the constitutional unit (a10), the proportion of the constitutional unit (a10) in the component (A1) is preferably in a range of 5% to 80% by mole, more preferably in a range of 10% to 75% by mole, still more preferably in a range of 30% to 70% by mole, and particularly preferably in a range of 30% to 60% by mole, with respect to the total amount (100% by mole) of all constitutional units constituting the component (A1).

In a case where the proportion of the constitutional unit (a10) is equal to or more than the lower limit value, the sensitivity can be more easily increased. On the other hand, in a case where the proportion of the constitutional unit (a10) is equal to or lower than the upper limit value, balance with other constitutional units is obtained easily.

In Regard to Constitutional Unit (a2):

The component (A1) may further have, as necessary, a constitutional unit (a2) (provided that a group having the constitutional unit (a1) is excluded) containing a lactone-containing cyclic group, a —$SO_2$—-containing cyclic group, or a carbonate-containing cyclic group, in addition to the constitutional unit (a1).

In a case where the component (A1) is used for forming a resist film, the lactone-containing cyclic group, the —$SO_2$—-containing cyclic group, or the carbonate-containing cyclic group in the constitutional unit (a2) is effective for improving the adhesiveness of the resist film to the substrate. Further, due to having the constitutional unit (a2), lithography characteristics can be improved, for example, by the effects obtained by appropriately adjusting the acid diffusion length, increasing the adhesiveness of the resist film to the substrate, and appropriately adjusting the solubility during development.

The term "lactone-containing cyclic group" indicates a cyclic group that contains a ring (lactone ring) containing a —O—C(=O)— in the ring skeleton. In a case where the lactone ring is counted as the first ring and the group contains only the lactone ring, the group is referred to as a monocyclic group. Further, in a case where the group has other ring structures, the group is referred to as a polycyclic group regardless of the structures. The lactone-containing cyclic group may be a monocyclic group or a polycyclic group.

The lactone-containing cyclic group for the constitutional unit (a2) is not particularly limited, and any lactone-containing cyclic group may be used. Specific examples thereof include groups each represented by General Formulae (a2-r-1) to (a2-r-7) shown below.

[Chemical Formula 30]

(a2-r-1)
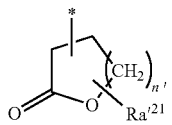

(a2-r-2)
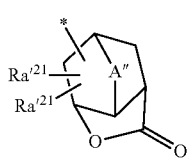

(a2-r-3)
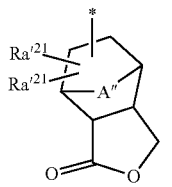

(a2-r-4)
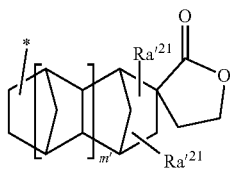

(a2-r-5)
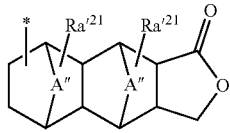

(a2-r-6)
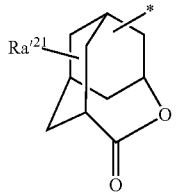

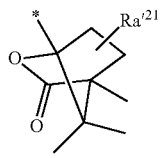

(a2-r-7)

[In the formulae, $Ra'^{21}$s each independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —$SO_2$—-containing cyclic group; A" represents an oxygen atom, a sulfur atom, or an alkylene group having 1 to 5 carbon atoms, which may contain an oxygen atom (—O—) or a sulfur atom (—S—); and n' represents an integer in a range of 0 to 2, and m' is 0 or 1.]

In General Formulae (a2-r-1) to (a2-r-7), the alkyl group as $Ra'^{21}$ is preferably an alkyl group having 1 to 6 carbon atoms. The alkyl group is preferably a linear alkyl group or a branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, and a hexyl group. Among these, a methyl group or ethyl group is preferable, and a methyl group is particularly preferable.

The alkoxy group as $Ra'^{21}$ is preferably an alkoxy group having 1 to 6 carbon atoms. Further, the alkoxy group is preferably a linear or branched alkoxy group. Specific examples of the alkoxy groups include a group formed by linking the above-described alkyl group mentioned as the alkyl group represented by $Ra'^{21}$ to an oxygen atom (—O—).

The halogen atom as $Ra'^{21}$ is preferably a fluorine atom.

Examples of the halogenated alkyl group as $Ra'^{21}$ include groups in which part or all of hydrogen atoms in the above-described alkyl group as $Ra'^{21}$ have been substituted with the above-described halogen atoms. The halogenated alkyl group is preferably a fluorinated alkyl group and particularly preferably a perfluoroalkyl group.

In —COOR" and —OC(=O)R" as $Ra'^{21}$, R" represents a hydrogen atom, an alkyl group, a lactone-containing cyclic group, a carbonate-containing cyclic group, or a —$SO_2$—-containing cyclic group.

The alkyl group as R" may be linear, branched, or cyclic, and preferably has 1 to 15 carbon atoms.

In a case where R" represents a linear or branched alkyl group, it is preferably an alkyl group having 1 to 10 carbon atoms, more preferably an alkyl group having 1 to 5 carbon atoms, and particularly preferably a methyl group or an ethyl group.

In a case where R" represents a cyclic alkyl group, the cyclic alkyl group preferably has 3 to 15 carbon atoms, more preferably 4 to 12 carbon atoms, and particularly preferably 5 to 10 carbon atoms. Specific examples thereof include a group in which one or more hydrogen atoms have been removed from a monocycloalkane, which may or may not be substituted with a fluorine atom or a fluorinated alkyl group; and a group in which one or more hydrogen atoms have been removed from polycycloalkanes such as bicycloalkane, tricycloalkane, or tetracycloalkane. More specific examples thereof include a group in which one or more hydrogen atoms have been removed from a monocycloalkane such as cyclopentane or cyclohexane; and a group in which one or more hydrogen atoms have been removed from a polycycloalkane such as adamantane, norbornane, isobornane, tricyclodecane, or tetracyclododecane.

Examples of the lactone-containing cyclic group as R" include the same groups as those each represented by General Formulae (a2-r-1) to (a2-r-7).

The carbonate-containing cyclic group as R" has the same definition as that for the carbonate-containing cyclic group described below. Specific examples of the carbonate-containing cyclic group include groups each represented by General Formulae (ax3-r-1) to (ax3-r-3).

The —$SO_2$—-containing cyclic group as R" has the same definition as that for the —$SO_2$—-containing cyclic group described below. Specific examples thereof include groups each represented by General Formulae (a5-r-1) to (a5-r-4).

The hydroxyalkyl group as $Ra'^{21}$ preferably has 1 to 6 carbon atoms, and specific examples thereof include a group in which at least one hydrogen atom in the alkyl group as $Ra'^{21}$ has been substituted with a hydroxyl group.

In General Formulae (a2-r-2), (a2-r-3) and (a2-r-5), as the alkylene group having 1 to 5 carbon atoms as A", a linear or branched alkylene group is preferable, and examples thereof include a methylene group, an ethylene group, an n-propylene group, and an isopropylene group. Specific examples of the alkylene groups that contain an oxygen atom or a sulfur atom include groups in which —O— or —S— is interposed in the terminal of the alkylene group or between the carbon atoms of the alkylene group, and examples thereof include —O—$CH_2$—, —$CH_2$—O—$CH_2$—, —S—$CH_2$—, and —$CH_2$—S—$CH_2$—. A" is preferably an alkylene group having 1 to 5 carbon atoms or —O—, more preferably an alkylene group having 1 to 5 carbon atoms, and most preferably a methylene group.

Specific examples of the groups each represented by General Formulae (a2-r-1) to (a2-r-7) are shown below.

[Chemical Formula 31]

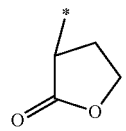

(r-lc-1-1)

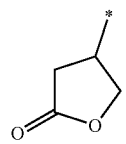

(r-lc-1-2)

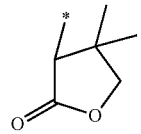

(r-lc-1-3)

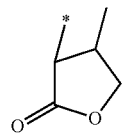

(r-lc-1-4)

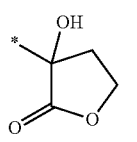
(r-lc-1-5)
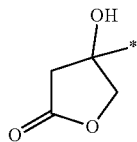
(r-lc-1-6)
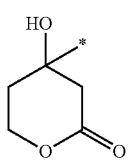
(r-lc-1-7)
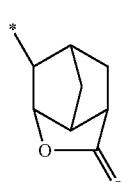
(r-lc-2-1)
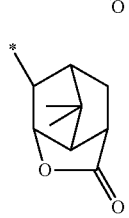
(r-lc-2-2)
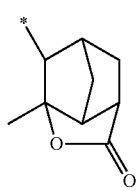
(r-lc-2-3)
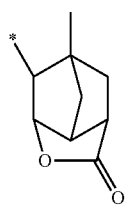
(r-lc-2-4)
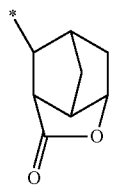
(r-lc-2-5)
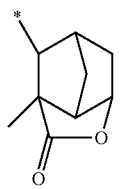
(r-lc-2-6)
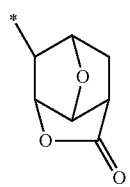
(r-lc-2-7)
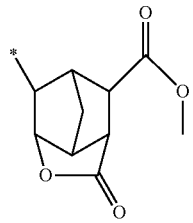
(r-lc-2-8)
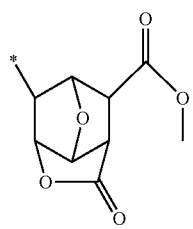
(r-lc-2-9)
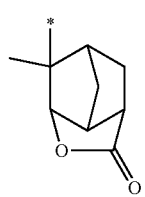
(r-lc-2-10)
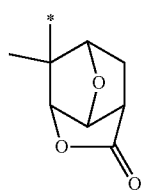
(r-lc-2-11)
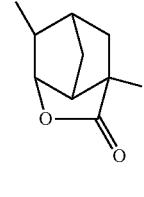
(r-lc-2-12)
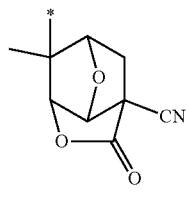
(r-lc-2-13)

-continued
(r-lc-2-14)
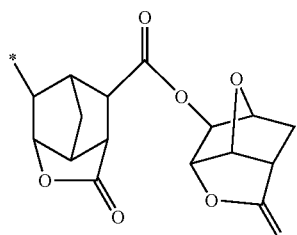
(r-lc-2-15)
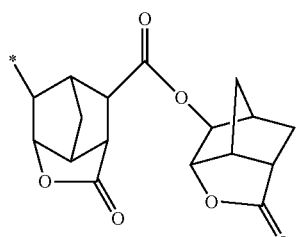
(r-lc-2-16)
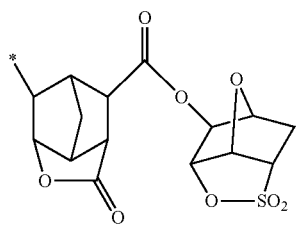
(r-lc-2-17)
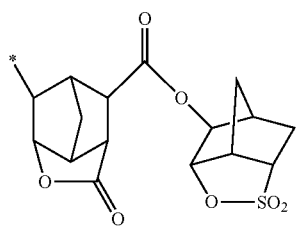
(r-lc-2-18)
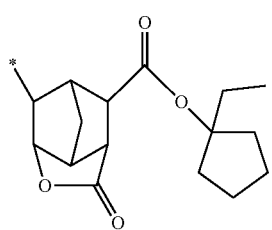
(r-lc-3-1)
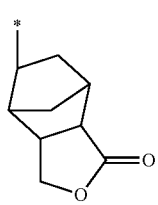
(r-lc-3-2)
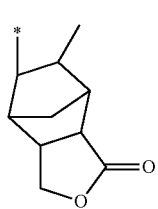
-continued
(r-lc-3-3)
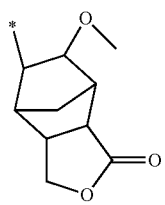
(r-lc-3-4)
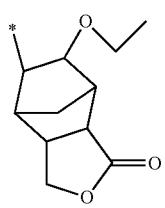
(r-lc-3-5)
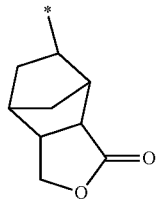
[Chemical Formula 32]
(r-lc-4-1)
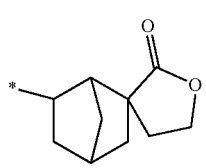
(r-lc-4-2)
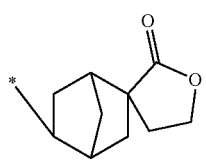
(r-lc-4-3)
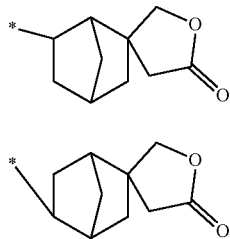
(r-lc-4-4)
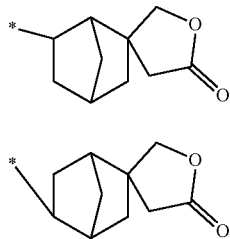
(r-lc-4-5)
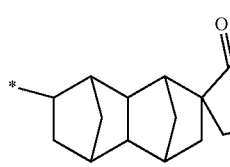
(r-lc-4-6)
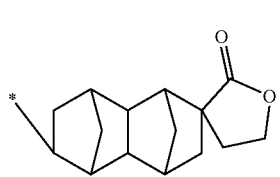

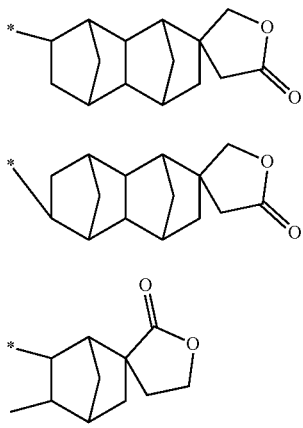

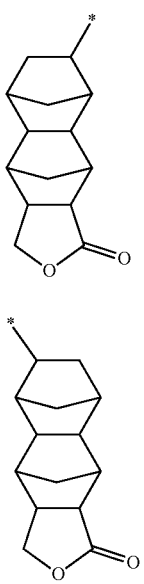

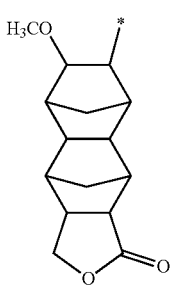

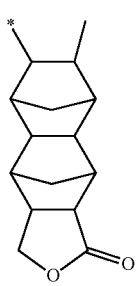

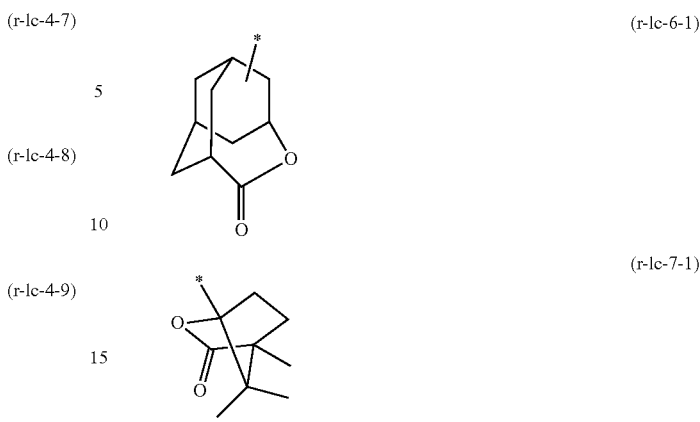

The "—$SO_2$—-containing cyclic group" indicates a cyclic group having a ring containing —$SO_2$— in the ring skeleton thereof. Specifically, the —$SO_2$—-containing cyclic group is a cyclic group in which the sulfur atom (S) in —$SO_2$— forms a part of the ring skeleton of the cyclic group. In a case where the ring containing —$SO_2$— in the ring skeleton thereof is counted as the first ring and the group contains only the ring, the group is referred to as a monocyclic group. Further, in a case where the group has other ring structures, the group is referred to as a polycyclic group regardless of the structures. The —$SO_2$—-containing cyclic group may be a monocyclic group or a polycyclic group. As the —$SO_2$—-containing cyclic group, a cyclic group containing —O—$SO_2$— in the ring skeleton thereof, in other words, a cyclic group containing a sultone ring in which —O—S— in the —O—$SO_2$— group forms a part of the ring skeleton thereof is particularly preferable.

More specific examples of the —$SO_2$—-containing cyclic group include groups each represented by General Formulae (a5-r-1) to (a5-r-4) shown below.

[Chemical Formula 33]

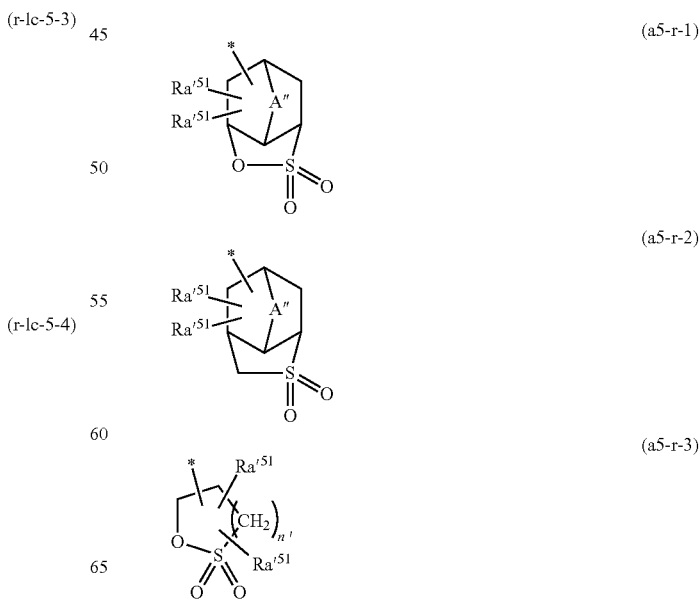

(a5-r-4)

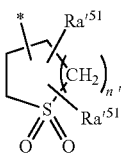

[In the formulae, each Ra'$^{51}$ independently represents a hydrogen atom, an alkyl group, an alkoxy group, a halogen atom, a halogenated alkyl group, a hydroxyl group, —COOR", —OC(═O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an oxygen atom, a sulfur atom, or an alkylene group having 1 to 5 carbon atoms, which may contain an oxygen atom or a sulfur atom; and n' represents an integer in a range of 0 to 2.]

In General Formulae (a5-r-1) and (a5-r-2), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(═O)R", and the hydroxyalkyl group as Ra'$^{51}$ include the same groups as those described above in the explanation of Ra'$^{21}$ in General Formulae (a2-r-1) to (a2-r-7).

Specific examples of the groups each represented by General Formulae (a5-r-1) to (a5-r-4) are shown below. In the formulae shown below, "Ac" represents an acetyl group.

[Chemical Formula 34]

(r-sl-1-1)

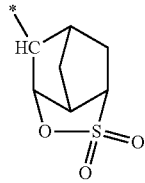

(r-sl-1-2)

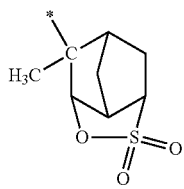

(r-sl-1-3)

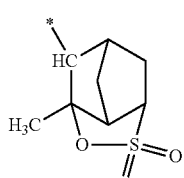

(r-sl-1-4)

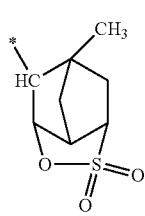

(r-sl-1-5)

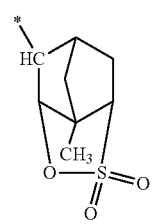

(r-sl-1-6)

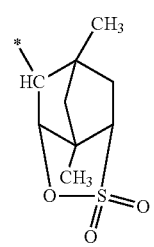

(r-sl-1-7)

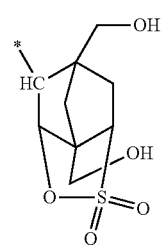

(r-sl-1-8)

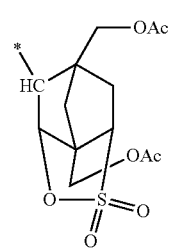

(r-sl-1-9)

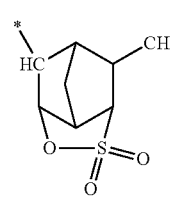

(r-sl-1-10)

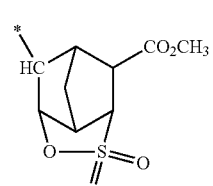

(r-sl-1-11)

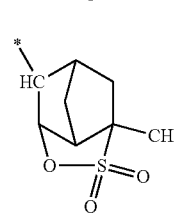

-continued
(r-sl-1-12)
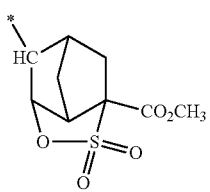
(r-sl-1-13)
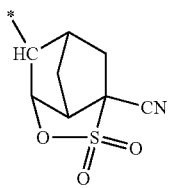
(r-sl-1-14)
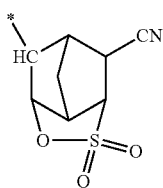
(r-sl-1-15)
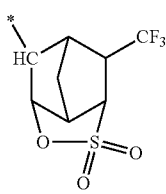
(r-sl-1-16)
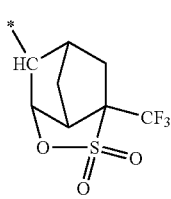
(r-sl-1-17)
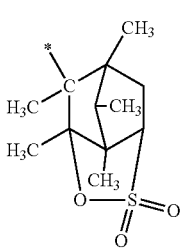
(r-sl-1-18)
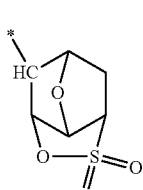
(r-sl-1-19)
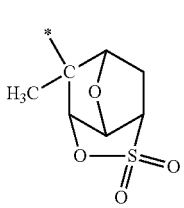
-continued
(r-sl-1-20)
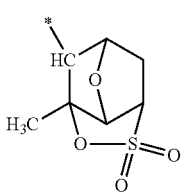
(r-sl-1-21)
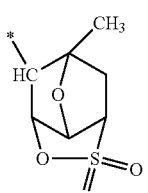
[Chemical Formula 35]
(r-sl-1-22)
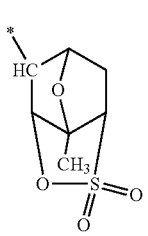
(r-sl-1-23)
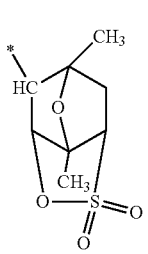
(r-sl-1-24)
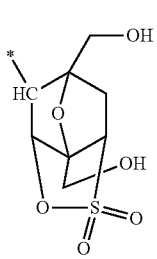
(r-sl-1-25)
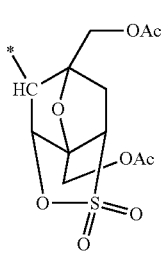
(r-sl-1-26)
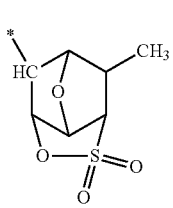

-continued (r-sl-1-27) 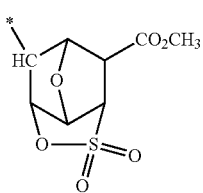

(r-sl-1-28) 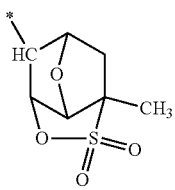

(r-sl-1-29) 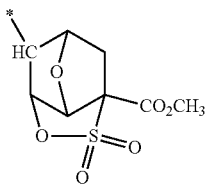

(r-sl-1-30) 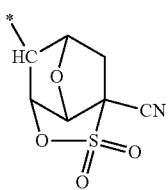

(r-sl-1-31) 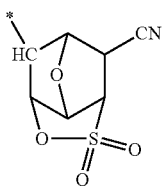

(r-sl-1-32) 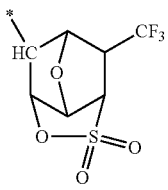

(r-sl-1-33)

[Chemical Formula 36]

(r-sl-2-1) 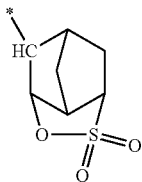

(r-sl-2-2) 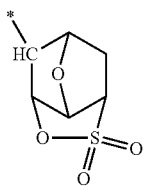

(r-sl-3-1) 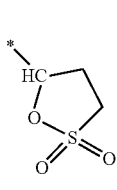

(r-sl-4-1) 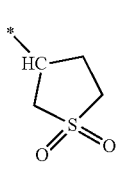

The "carbonate-containing cyclic group" indicates a cyclic group having a ring (a carbonate ring) containing —O—C(═O)—O— in the ring skeleton thereof. In a case where the carbonate ring is counted as the first ring and the group contains only the carbonate ring, the group is referred to as a monocyclic group. Further, in a case where the group has other ring structures, the group is referred to as a polycyclic group regardless of the structures. The carbonate-containing cyclic group may be a monocyclic group or a polycyclic group.

The carbonate ring-containing cyclic group is not particularly limited, and any carbonate ring-containing cyclic group may be used. Specific examples thereof include groups each represented by General Formulae (ax3-r-1) to (ax3-r-3) shown below.

[Chemical Formula 37]

(ax3-r-1) 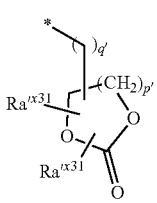

(ax3-r-2) 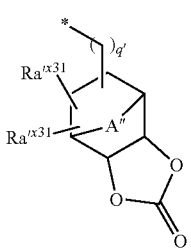

(ax3-r-3)

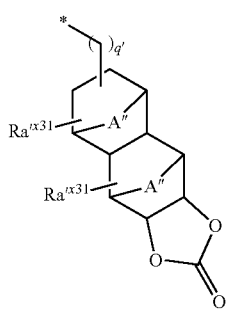

[In the formulae, each $Ra^{\prime x31}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; R" represents a hydrogen atom, an alkyl group, a lactone-containing cyclic group, a carbonate-containing cyclic group, or a —SO$_2$—-containing cyclic group; A" represents an oxygen atom, a sulfur atom, or an alkylene group having 1 to 5 carbon atoms, which may contain an oxygen atom or a sulfur atom; and p' represents an integer in a range of 0 to 3, and q' is 0 or 1.]

In General Formulae (ax3-r-2) and (ax3-r-3), A" has the same definition as that for A" in General Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group as $Ra^{\prime 31}$ include the same groups as those described above in the explanation of $Ra^{\prime 21}$ in General Formulae (a2-r-1) to (a2-r-7).

Specific examples of the groups each represented by General Formulae (ax3-r-1) to (ax3-r-3) are shown below.

[Chemical Formula 38]

(r-cr-1-1)

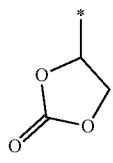

(r-cr-1-2)

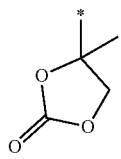

(r-cr-1-3)

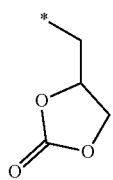

(r-cr-1-4)

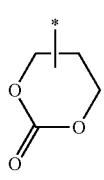

(r-cr-1-5)

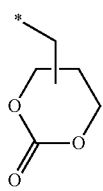

(r-cr-1-6)

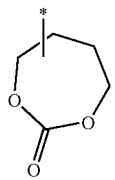

(r-cr-1-7)

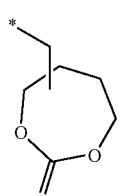

(r-cr-2-1)

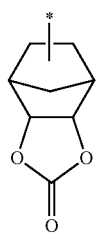

(r-cr-2-2)

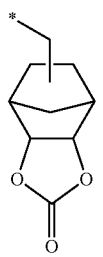

(r-cr-2-3)

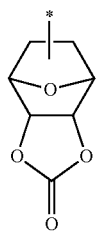

(r-cr-2-4)

(r-cr-3-1)

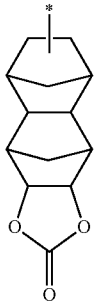

(r-cr-3-2)

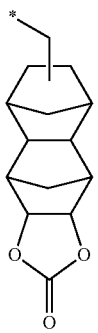

(r-cr-3-3)

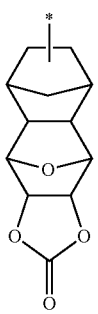

(r-cr-3-4)

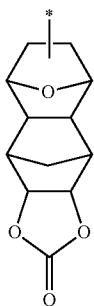

(r-cr-3-5)

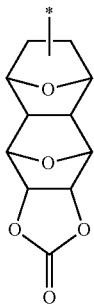

Among them, the constitutional unit (a2) is preferably a constitutional unit derived from acrylic acid ester in which the hydrogen atom bonded to the carbon atom at the α-position may be substituted with a substituent.

The constitutional unit (a2) is preferably a constitutional unit represented by General Formula (a2-1).

[Chemical Formula 39]

(a2-1)

[In the formula, R represents a hydrogen atom, an alkyl group having 1 to 5 carbon atoms, or a halogenated alkyl group having 1 to 5 carbon atoms. $Ya^{21}$ represents a single bond or a divalent linking group. $La^{21}$ represents —O—, —COO—, —CON(R')—, —OCO—, —CONHCO— or —CONHCS—, and R' represents a hydrogen atom or a methyl group. However, in a case where $La^{21}$ represents —O—, $Ya^{21}$ does not represent —CO—. $Ra^{21}$ represents a lactone-containing cyclic group, a carbonate-containing cyclic group, or a —$SO_2$—-containing cyclic group.]

In General Formula (a2-1), R has the same definition as described above. R is preferably a hydrogen atom, an alkyl group having 1 to 5 carbon atoms, or a fluorinated alkyl group having 1 to 5 carbon atoms, and particularly preferably a hydrogen atom or a methyl group in terms of industrial availability.

In General Formula (a2-1), the divalent linking group as $Ya^{21}$ is not particularly limited, and suitable examples thereof include a divalent hydrocarbon group which may have a substituent and a divalent linking group having a hetero atom.

Divalent Hydrocarbon Group Which may have Substituent:

In a case where $Ya^{21}$ represents a divalent hydrocarbon group which may have a substituent, the hydrocarbon group may be an aliphatic hydrocarbon group or an aromatic hydrocarbon group.

Aliphatic Hydrocarbon Group as $Ya^{21}$

The aliphatic hydrocarbon group indicates a hydrocarbon group that has no aromaticity. The aliphatic hydrocarbon group may be saturated or unsaturated. In general, it is preferable that the aliphatic hydrocarbon group be saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear aliphatic hydrocarbon group preferably has 1 to 10 carbon atoms, more preferably 1 to 6 carbon atoms, still more preferably 1 to 4 carbon atoms, and most preferably 1 to 3 carbon atoms.

The linear aliphatic hydrocarbon group is preferably a linear alkylene group, and specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group preferably has 2 to 10 carbon atoms, more preferably 3 to 6 carbon atoms, still more preferably 3 or 4 carbon atoms, and most preferably 3 carbon atoms.

The branched aliphatic hydrocarbon group is preferably a branched alkylene group, and specific examples thereof include alkylalkylene groups, for example, alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. The alkyl group in the alkylalkylene group is preferably a linear alkyl group having 1 to 5 carbon atoms.

The linear or branched aliphatic hydrocarbon group may or may not have a substituent. Examples of the substituent include a fluorine atom, a fluorinated alkyl group having 1 to 5 carbon atoms, which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed in a linear or branched aliphatic hydrocarbon group. Examples of the linear or branched aliphatic hydrocarbon group include the same groups as those described above.

The cyclic aliphatic hydrocarbon group preferably has 3 to 20 carbon atoms and more preferably 3 to 12 carbon atoms.

The cyclic aliphatic hydrocarbon group may be a polycyclic group or a monocyclic group. The monocyclic alicyclic hydrocarbon group is preferably a group in which two hydrogen atoms have been removed from a monocycloalkane. The monocycloalkane preferably has 3 to 6 carbon atoms, and specific examples thereof include cyclopentane and cyclohexane. The polycyclic alicyclic hydrocarbon group is preferably a group in which two hydrogen atoms have been removed from a polycycloalkane, and the polycycloalkane is preferably a group having 7 to 12 carbon atoms. Specific examples of the polycyclic alicyclic hydrocarbon group include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, and a carbonyl group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and still more preferably a methoxy group or an ethoxy group.

The halogen atom as the substituent is preferably a fluorine atom.

Examples of the halogenated alkyl group as the substituent include groups in which part or all of hydrogen atoms in the above-described alkyl groups have been substituted with the above-described halogen atoms.

In the cyclic aliphatic hydrocarbon group, a part of carbon atoms constituting the ring structure thereof may be substituted with a substituent containing a hetero atom. The substituent containing a hetero atom is preferably —O—, —C(=O)—O—, —S—, —S(=O)$_2$—, or —S(=O)$_2$—O—.

Aromatic Hydrocarbon Group as Ya$^{21}$

An aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring preferably has 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms.

Specific examples of the aromatic ring include aromatic hydrocarbon rings such as benzene, naphthalene, anthracene, and phenanthrene; and an aromatic heterocyclic ring in which a part of carbon atoms constituting the above-described aromatic hydrocarbon ring have been substituted with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group in which two hydrogen atoms have been removed from the above-described aromatic hydrocarbon ring or aromatic heterocyclic ring (an arylene group or a heteroarylene group); a group in which two hydrogen atoms have been removed from an aromatic compound having two or more aromatic rings (such as biphenyl or fluorene); and a group in which one hydrogen atom of a group (an aryl group or a heteroaryl group) in which one hydrogen atoms has been removed from the above-described aromatic hydrocarbon ring or aromatic heterocyclic ring has been substituted with an alkylene group (for example, a group in which one hydrogen atom has been further removed from an aryl group in arylalkyl groups such as a benzyl group, a phenethyl group, a 1-naphthylmethyl group, a 2-naphthylmethyl group, a 1-naphthylethyl group, or a 2-naphthylethyl group). The alkylene group bonded to the aryl group or the heteroaryl group preferably has 1 to 4 carbon atoms, more preferably 1 or 2 carbon atoms, and particularly preferably 1 carbon atoms.

With respect to the aromatic hydrocarbon group, the hydrogen atom which the aromatic hydrocarbon group has may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group having 1 to 5 carbon atoms, and a methyl group, an ethyl group, a propyl group, an n-butyl group, or a tert-butyl group is most preferable.

Examples of the alkoxy group, the halogen atom, and the halogenated alkyl group, as the substituent, include the same groups as those exemplified as the substituent that is substituted for a hydrogen atom which the cyclic aliphatic hydrocarbon group has.

Divalent Linking Group Containing Hetero Atom

In a case where $Ya^{21}$ represents a divalent linking group containing a hetero atom, preferred examples of the linking group include —O—, —C(=O)—O—, —O—C(=O)—, —C(=O)—, —O—C(=O)—O—, —C(=O)—NH—, —NH—, —NH—C(=NH)— (H may be substituted with a substituent such as an alkyl group, an acyl group, or the like), —S—, —S(=O)$_2$—, —S(=O)$_2$—O—, and a group represented by General Formula —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represent a divalent hydrocarbon group which may have a substituent, O represents an oxygen atom, and m" represents an integer in a range of 0 to 3].

In a case where the divalent linking group containing a hetero atom is —C(=O)—NH—, —C(=O)—NH—C(=O)—, —NH—, or —NH—C(=NH)—, H may be substituted with a substituent such as an alkyl group, an acyl group, or the like. The substituent (an alkyl group, an acyl group, or the like) preferably has 1 to 10 carbon atoms, more preferably 1 to 8 carbon atoms, and most preferably 1 to 5 carbon atoms.

In General Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$—, and —Y$^{21}$—S(=O)$_2$—O—Y$^{22}$—, Y$^{21}$, and Y$^{22}$ each independently represent a divalent hydrocarbon group which may have a substituent. Examples of the divalent hydrocarbon group include those (mentioned as the divalent hydrocarbon group which may have a substituent) in the description of the above-described divalent linking group as $Ya^{21}$.

$Y^{21}$ is preferably a linear aliphatic hydrocarbon group, more preferably a linear alkylene group, still more preferably a linear alkylene group having 1 to 5 carbon atoms, and particularly preferably a methylene group or an ethylene group.

$Y^{22}$ is preferably a linear or branched aliphatic hydrocarbon group and more preferably a methylene group, an ethylene group, or an alkylmethylene group. The alkyl group in the alkylmethylene group is preferably a linear alkyl group having 1 to 5 carbon atoms, more preferably a linear alkyl group having 1 to 3 carbon atoms, and most preferably a methyl group.

In the group represented by Formula —[Y$^{21}$—C(=O)—O]$_{m''}$—Y$^{22}$—, m" represents an integer in a range of 0 to 3, preferably an integer in a range of 0 to 2, more preferably 0 or 1, and particularly preferably 1. In other words, it is particularly preferable that the group represented by Formula —[Y$^{21}$—C(=O)—O]$_{m''}$—Y$^{22}$— represent a group represented by Formula —Y$^{21}$—C(=O)—O—Y$^{22}$—. Among these, a group represented by Formula —(CH$_2$)$_{a'}$—C(=O)—O—(CH$_2$)$_{b'}$— is preferable. In the formula, a' represents an integer in a range of 1 to 10, preferably an integer in a range of 1 to 8, more preferably an integer in a range of 1 to 5, still more preferably 1 or 2, and most preferably 1. b' represents an integer in a range of 1 to 10, preferably an integer in a range of 1 to 8, more preferably an integer in a range of 1 to 5, still more preferably 1 or 2, and most preferably 1.

Among the above, $Ya^{21}$ is preferably a single bond, an ester bond [—C(=O)—O—], an ether bond (—O—), a linear or branched alkylene group, or a combination thereof.

In General Formula (a2-1), $Ra^{21}$ represents a lactone-containing cyclic group, a —SO$_2$—-containing cyclic group, or a carbonate-containing cyclic group.

Suitable examples of the lactone-containing cyclic group, the —SO$_2$—-containing cyclic group, and the carbonate-containing cyclic group as $Ra^{21}$ include groups each represented by General Formulae (a2-r-1) to (a2-r-7), groups each represented by General Formulae (a5-r-1) to (a5-r-4), and groups each represented by General Formulae (ax3-r-1) to (ax3-r-3) described above.

Among them, a lactone-containing cyclic group or a —SO$_2$—-containing cyclic group is preferable, and groups each represented by General Formula (a2-r-1), (a2-r-2), (a2-r-6), or (a5-r-1) are more preferable. Specifically, groups each represented by any of Chemical Formulae (r-1c-1-1) to (r-1c-1-7), (r-1c-2-1) to (r-1c-2-18), (r-1c-6-1), (r-s1-1-1), and (r-s1-1-18) are more preferable.

The constitutional unit (a2) which the component (A1) has may be one kind or may be two or more kinds.

In a case where the component (A1) has the constitutional unit (a2), the proportion of the constitutional unit (a2) in the component (A1) is preferably in a range of 5% to 60% by mole, more preferably in a range of 10% to 60% by mole, still more preferably in a range of 20% to 55% by mole, and particularly preferably in a range of 30% to 50% by mole with respect to the total amount (100% by mole) of all constitutional units constituting the component (A1).

In a case where the proportion of the constitutional unit (a2) is equal to or greater than the lower limit value of the above-described preferred range, the effect obtained by allowing the component (A1) to contain the constitutional unit (a2) can be sufficiently achieved by the effect described above. In a case where the proportion of the constitutional unit (a2) is equal to or lower than the upper limit value of the above-described preferred range, balance with other constitutional units can be obtained, and various lithography characteristics are improved.

In Regard to Constitutional Unit (a3):

The component (A1) may further have, as necessary, a constitutional unit (a3) (provided that a constitutional unit corresponding to the constitutional unit (a1) or the constitutional unit (a2) is excluded) containing a polar group-containing aliphatic hydrocarbon group, in addition to the constitutional unit (a1). In a case where the component (A1) has the constitutional unit (a3), the hydrophilicity of the component (A) is increased, which contributes to an improvement in resolution. Further, acid diffusion length can be appropriately adjusted.

Examples of the polar group include a hydroxyl group, a cyano group, a carboxy group, or a hydroxyalkyl group in which a part of hydrogen atoms of the alkyl group have been substituted with a fluorine atom, and the polar group is particularly preferably a hydroxyl group.

Examples of the aliphatic hydrocarbon group include a linear or branched hydrocarbon group (preferably an alkylene group) having 1 to 10 carbon atoms, and a cyclic aliphatic hydrocarbon group (a cyclic group). The cyclic group may be a monocyclic group or a polycyclic group. For example, these cyclic groups can be suitably selected from a large number of groups that have been proposed in resins for a resist composition for an ArF excimer laser.

In a case where the cyclic group is a monocyclic group, the monocyclic group preferably has 3 to 10 carbon atoms. Among them, a constitutional unit derived from an acrylic acid ester that includes an aliphatic monocyclic group containing a hydroxyl group, cyano group, carboxy group, or a hydroxyalkyl group in which a part of hydrogen atoms of the alkyl group have been substituted with a fluorine atom are particularly preferable. Examples of the monocyclic group include a group in which two or more hydrogen atoms have been removed from a monocycloalkane. Specific examples of the monocyclic group a include group in which two or more hydrogen atoms have been removed from a monocycloalkane such as cyclopentane, cyclohexane, or cyclooctane. Among these monocyclic groups, a group in which two or more hydrogen atoms have been removed from cyclopentane or a group in which two or more hydrogen atoms have been removed from cyclohexane are industrially preferable.

In a case where the cyclic group is a polycyclic group, the polycyclic group preferably has 7 to 30 carbon atoms. Among them, a constitutional unit derived from an acrylic acid ester that includes an aliphatic polycyclic group containing a hydroxyl group, cyano group, carboxy group, or a hydroxyalkyl group in which a part of hydrogen atoms of the alkyl group have been substituted with a fluorine atom is particularly preferable.

Examples of the polycyclic group include groups in which two or more hydrogen atoms have been removed from a bicycloalkane, tricycloalkane, tetracycloalkane, or the like. Specific examples thereof include a group in which two or more hydrogen atoms have been removed from a polycycloalkane such as adamantane, norbornane, isobornane, tricyclodecane, or tetracyclododecane. Among these polycyclic groups, a group in which two or more hydrogen atoms have been removed from adamantane, a group in which two or more hydrogen atoms have been removed from norbornane, or a group in which two or more hydrogen atoms have been removed from tetracyclododecane are industrially preferable.

The constitutional unit (a3) is not particularly limited, and any constitutional unit may be used as long as the constitutional unit contains a polar group-containing aliphatic hydrocarbon group.

The constitutional unit (a3) is a constitutional unit derived from acrylic acid ester in which the hydrogen atom bonded to the carbon atom at the α-position may be substituted with a substituent, and a constitutional unit containing a polar group-containing aliphatic hydrocarbon group is preferable.

In a case where the hydrocarbon group in the polar group-containing aliphatic hydrocarbon group is a linear or branched hydrocarbon group having 1 to 10 carbon atoms, the constitutional unit (a3) is preferably a constitutional unit derived from a hydroxyethyl ester of acrylic acid.

Further, as the constitutional unit (a3), in a case where the hydrocarbon group in the polar group-containing aliphatic hydrocarbon group is a polycyclic group, a constitutional unit represented by General Formula (a3-1), a constitutional unit represented by General Formula (a3-2), and a constitutional unit represented by General Formula (a3-3) are preferable, and in a case where the hydrocarbon group is a monocyclic group, a constitutional unit represented by General Formula (a3-4) is preferable.

[Chemical Formula 40]

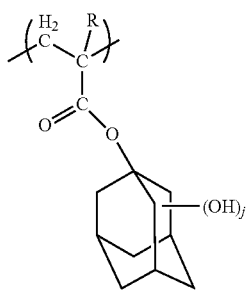

(a3-1)

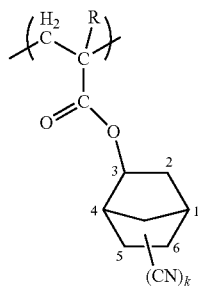

(a3-2)

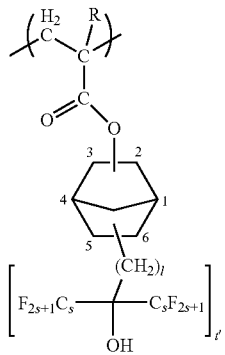

(a3-3)

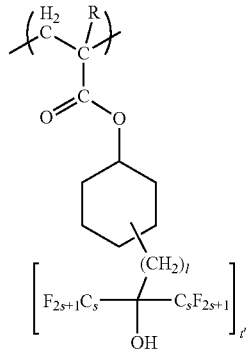

(a3-4)

[In the formulae, R has the same definition as described above, j represents an integer in a range of 1 to 3, k represents an integer in a range of 1 to 3, t' represents an integer in a range of 1 to 3, l represents an integer in a range of 0 to 5, and s represents an integer in a range of 1 to 3.]

In General Formula (a3-1), j preferably represents 1 or 2 and more preferably 1. In a case where j represents 2, it is preferable that the hydroxyl groups be bonded to the 3- and 5-positions of the adamantyl group. In a case where j represents 1, it is preferable that the hydroxyl group be bonded to the 3-position of the adamantyl group.

It is preferable that j represent 1, and it is particularly preferable that the hydroxyl group be bonded to the 3-position of the adamantyl group.

In General Formula (a3-2), k preferably represents 1. The cyano group is preferably bonded to the 5- or 6-position of the norbornyl group.

In General Formula (a3-3), it is preferable that t' represent 1. It is preferable that l represent 1. It is preferable that s represent 1. Further, it is preferable that a 2-norbornyl group or 3-norbornyl group be bonded to the terminal of the carboxy group of the acrylic acid. It is preferable that the fluorinated alkyl alcohol be bonded to the 5- or 6-position of the norbornyl group.

In General Formula (a3-4), it is preferable that t' represent 1 or 2. It is preferable that 1 represent 0 or 1. It is preferable that s represent 1. It is preferable that the fluorinated alkyl alcohol be bonded to the 3- or 5-position of the cyclohexyl group.

The constitutional unit (a3) which the component (A1) has may be one kind or may be two or more kinds.

In a case where the component (A1) has the constitutional unit (a3), the proportion of the constitutional unit (a3) is preferably in a range of 1% to 30% by mole, more preferably in a range of 2% to 25% by mole, and still more preferably in a range of 5% to 20% by mole, with respect to the total amount (100% by mole) of all constitutional units constituting the component (A1).

In a case where the proportion of the constitutional unit (a3) is equal to or greater than the lower limit value of the above-described preferred range, the effect obtained by allowing the component (A1) to contain the constitutional unit (a3) can be sufficiently achieved by the effect described above. In a case where the proportion of the constitutional unit (a3) is equal to or lower than the upper limit value of the above-described preferred range, balance with other constitutional units can be obtained, and various lithography characteristics are improved.

In Regard to Constitutional Unit (a4):

The component (A1) may further have, in addition to the constitutional unit (a1), a constitutional unit (a4) containing an acid non-dissociable aliphatic cyclic group.

In a case where the component (A1) has the constitutional unit (a4), the dry etching resistance of the formed resist pattern is improved. Further, the hydrophobicity of the component (A) increases. The improvement in hydrophobicity contributes to the improvement in resolution, a resist pattern shape, and the like, particularly in the case of a solvent developing process. The "acid non-dissociable cyclic group" in the constitutional unit (a4) is a cyclic group that remains in the constitutional unit without being dissociated even in a case where an acid acts thereto in a case where the acid is generated in the resist composition upon exposure (for example, in a case where the acid is generated from the constitutional unit that generates an acid upon exposure or the component (B)).

Examples of the constitutional unit (a4) preferably include a constitutional unit derived from an acrylic acid ester including an acid non-dissociable aliphatic cyclic group. As the cyclic group, many cyclic groups conventionally known as cyclic groups used as a resin component of a resist composition for ArF excimer laser, KrF excimer laser (preferably ArF excimer laser), or the like can be used.

The cyclic group is particularly preferably at least one selected from a tricyclodecyl group, an adamantyl group, a tetracyclododecyl group, an isobornyl group, and a norbornyl group, from the viewpoint of industrial availability. These polycyclic groups may have, as a substituent, a linear or branched alkyl group having 1 to 5 carbon atoms.

Specific examples of the constitutional unit (a4) include constitutional units each represented by General Formulae (a4-1) to (a4-7).

[Chemical Formula 41]

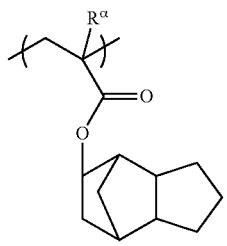
(a4-1)

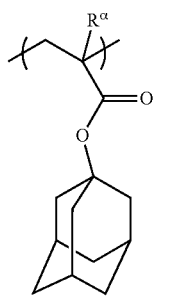
(a4-2)

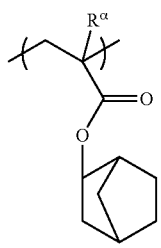
(a4-3)

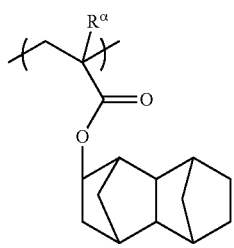
(a4-4)

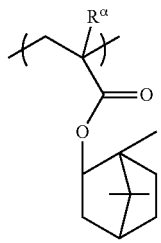
(a4-5)

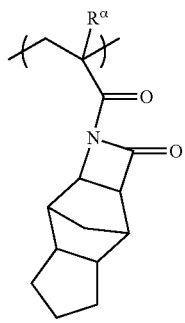
(a4-6)

-continued

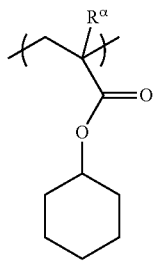
(a4-7)

[In the formula, $R^\alpha$ is the same as above.]

The constitutional unit (a4) which the component (A1) has may be one kind or may be two or more kinds.

In a case where the component (A1) has the constitutional unit (a4), the proportion of the constitutional unit (a4) is preferably in a range of 1% to 40% by mole and more preferably in a range of 5% to 20% by mole, with respect to the total (100% by mole) of all constitutional units constituting the component (A1).

In a case where the proportion of the constitutional unit (a4) is equal to or greater than the lower limit value of the preferred range, the effect that is obtained by allowing the component (A1) to contain the constitutional unit (a4) can be sufficiently achieved. In a case where the proportion of the constitutional unit (a4) is equal to or lower than the upper limit value of the preferred range, the balance with other constitutional units is obtained easily.

In Regard to Constitutional Unit (st):

The constitutional unit (st) is a constitutional unit derived from styrene or a styrene derivative. A "constitutional unit derived from styrene" means a constitutional unit that is formed by the cleavage of an ethylenic double bond of styrene. A "constitutional unit derived from a styrene derivative" means a constitutional unit (provided that a constitutional unit corresponding to the constitutional unit (a10) is excluded) formed by the cleavage of an ethylenic double bond of a styrene derivative.

The "styrene derivative" means a compound in which at least a part of hydrogen atoms of styrene are substituted with a substituent. Examples of the styrene derivative include a derivative in which the hydrogen atom at the α-position of styrene is substituted with a substituent, a derivative in which one or more hydrogen atoms of the benzene ring of styrene are substituted with a substituent, and a derivative in which the hydrogen atom at the α-position of styrene and one or more hydrogen atoms of the benzene ring are substituted with a substituent.

Examples of the substituent that is substituted for the hydrogen atom at the α-position of styrene include an alkyl group having 1 to 5 carbon atoms or a halogenated alkyl group having 1 to 5 carbon atoms.

The alkyl group having 1 to 5 carbon atoms is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an isopentyl group, and a neopentyl group.

The halogenated alkyl group having 1 to 5 carbon atoms is a group in which part or all of hydrogen atoms in the alkyl group having 1 to 5 carbon atoms have been substituted with a halogen atom. The halogen atom is particularly preferably a fluorine atom.

The substituent that is substituted for the hydrogen atom at the α-position of styrene is preferably an alkyl group having 1 to 5 carbon atoms or a fluorinated alkyl group having 1 to 5 carbon atoms, more preferably an alkyl group having 1 to 3 carbon atoms or a fluorinated alkyl group having 1 to 3 carbon atoms, and still more preferably a methyl group from the viewpoint of industrial availability.

Examples of the substituent that is substituted for the hydrogen atom of the benzene ring of styrene include an alkyl group, an alkoxy group, a halogen atom, and a halogenated alkyl group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and still more preferably a methoxy group or an ethoxy group.

The halogen atom as the substituent is preferably a fluorine atom.

Examples of the halogenated alkyl group as the substituent include groups in which part or all of hydrogen atoms in the above-described alkyl groups have been substituted with the above-described halogen atoms.

The substituent that is substituted for the hydrogen atom of the benzene ring of styrene is preferably an alkyl group having 1 to 5 carbon atoms, more preferably a methyl group or an ethyl group, and still more preferably a methyl group.

The constitutional unit (st) is preferably a constitutional unit derived from styrene or a constitutional unit derived from a styrene derivative in which the hydrogen atom at the α-position of styrene is substituted with an alkyl group having 1 to 5 carbon atoms or a halogenated alkyl group having 1 to 5 carbon atoms, more preferably a constitutional unit derived from styrene, or a constitutional unit derived from a styrene derivative in which the hydrogen atom at the α-position of styrene is substituted with a methyl group, and still more preferably a constitutional unit derived from styrene.

The constitutional unit (st) which the component (A1) has may be one kind or may be two or more kinds.

In a case where the component (A1) has the constitutional unit (st), the proportion of the constitutional unit (st) is preferably in a range of 1% to 30% by mole and more preferably in a range of 3% to 20% by mole with respect to the total amount (100% by mole) of all constitutional units constituting the component (A1).

The component (A1) contained in the resist composition may be used alone or in a combination of two or more kinds thereof.

In the resist composition according to the present embodiment, examples of the component (A1) include a polymer compound having a repeated structure of the constitutional unit (a1).

Examples of the preferred component (A1) include a polymer compound having a repeated structure of the constitutional unit (a1) and the constitutional unit (a10).

Examples of the more preferred component (A1) include a polymer compound having a repeated structure of the constitutional unit (a1), the constitutional unit (a10), and the constitutional unit (a3).

In this case, the proportion of the constitutional unit (a1) in each of the polymer compounds described above is preferably in a range of 5% to 80% by mole, more preferably in a range of 10% to 75% by mole, still more preferably in a range of 30% to 70% by mole, and particularly preferably in a range of 40% to 60% by mole, with respect to the total amount (100% by mole) of all constitutional units constituting the polymer compound.

In addition, the proportion of the constitutional unit (a10) in each of the polymer compounds described above is preferably in a range of 5% to 80% by mole, more preferably in a range of 10% to 75% by mole, still more preferably in a range of 30% to 70% by mole, and particularly preferably in a range of 40% to 60% by mole, with respect to the total amount (100% by mole) of all constitutional units constituting the polymer compound.

The molar ratio of the constitutional unit (a1) to the constitutional unit (a10) in the polymer compound (the constitutional unit (a1):the constitutional unit (a10)) is preferably in a range of 3:6 to 6:1, more preferably in a range of 4:5 to 7:3, and still more preferably in a range of 5:4 to 2:1.

In a case where the constitutional unit (a3) is included in the polymer compound, the proportion of the constitutional unit (a3) is preferably in a range of 1% to 20% by mole, more preferably in a range of 2% to 15% by mole, and still more preferably in a range of 5% to 10% by mole, with respect to the total amount (100% by mole) of all constitutional units constituting the polymer compound.

The component (A1) can be produced by dissolving, in a polymerization solvent, each monomer from which the constitutional unit is derived, adding thereto a radical polymerization initiator such as azobisisobutyronitrile (AIBN) or dimethyl azobisisobutyrate (for example, V-601) to carry out polymerization.

Alternatively, the component (A1) can be produced by dissolving, in a polymerization solvent, a monomer from which the constitutional unit (a1) is derived and, as necessary, a monomer from which a constitutional unit other than the constitutional unit (a1) is derived, and adding thereto a radical polymerization initiator such as described above to carry out polymerization and then carry outing a deprotection reaction.

Further, a —C(CF$_3$)$_2$—OH group may be introduced into the terminal of the component (A1) during the polymerization using a chain transfer agent such as HS—CH$_2$—CH$_2$—CH$_2$—C(CF$_3$)$_2$—OH in combination. As described above, a copolymer into which a hydroxyalkyl group, formed by substitution of a part of hydrogen atoms in the alkyl group with fluorine atoms, has been introduced is effective for reducing development defects and reducing line edge roughness (LER: uneven irregularities of a line side wall).

The weight-average molecular weight (Mw) (based on the polystyrene-equivalent value determined by gel permeation chromatography (GPC)) of the component (A1), which is not particularly limited, is preferably in a range of 1,000 to 50,000, more preferably in a range of 2,000 to 30,000, and still more preferably in a range of 3,000 to 20,000.

In a case where Mw of the component (A1) is equal to or lower than the upper limit value of this preferred range, the resist composition exhibits sufficient solubility in a solvent for a resist such that the resist composition can be used as a resist. On the other hand, in a case where Mw of the component (A1) is equal to or greater than the lower limit value of this preferred range, dry etching resistance and the cross-sectional shape of the resist pattern become excellent.

Further, the dispersity (Mw/Mn) of the component (A1) is not particularly limited; however, it is preferably in a range of 1.0 to 4.0, more preferably in a range of 1.0 to 3.0, and particularly preferably in a range of 1.0 to 2.0. Mn represents the number-average molecular weight.

In Regard to Component (A2)

In the resist composition according to the present embodiment, a base material component (hereinafter, referred to as a "component (A2)") exhibiting changed solubility in a developing solution under action of acid, which does not correspond to the component (A1), may be used in combination as the component (A).

The component (A2) is not particularly limited and may be freely selected and used from a large number of conventionally known base material components for the chemical amplification-type resist composition.

As the component (A2), a polymer compound or a low-molecular-weight compound may be used alone or in a combination of two or more kinds thereof.

The proportion of the component (A1) in the component (A) is preferably 25% by mass or greater, more preferably 50% by mass or greater, still more preferably 75% by mass or greater, and may be 100% by mass with respect to the total mass of the component (A). In a case where the proportion is 25% by mass or more, a resist pattern having various excellent lithography characteristics such as high sensitivity, resolution, and roughness amelioration can be easily formed.

The content of the component (A) in the resist composition according to the present embodiment may be adjusted depending on the resist film thickness to be formed and the like.

<Component (D0)>

The component (D0) is a compound represented by General Formula (d0).

In the resist composition of the present aspect, in a case where the component (D0) is contained, a resist pattern having good fine resolution can be formed.

[Chemical Formula 42]

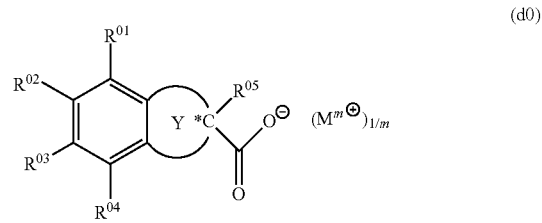

(d0)

[In the formula, R$^{01}$, R$^{02}$, R$^{03}$, and R$^{04}$ each independently represent a hydrogen atom, a hydroxy group, a halogen atom, or an alkyl group having 1 to 5 carbon atoms. Alternatively, R$^{01}$ and R$^{02}$, R$^{02}$ and R$^{03}$, or R$^{03}$ and R$^{04}$ are bonded to each other to form an aromatic ring. The aromatic ring may have a substituent. R$^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group. m represents an integer of 1 or more, and M$^{m+}$ represents an m-valent organic cation.]

<<Anion Moiety in General Formula (d0)>>

In General Formula (d0), R$^{01}$, R$^{02}$, R$^{03}$ and R$^{04}$ each independently represent a hydrogen atom, a hydroxy group, a halogen atom, or an alkyl group having 1 to 5 carbon atoms. Alternatively, R$^{01}$ and R$^{02}$, R$^{02}$ and R$^{03}$, or R$^{03}$ and R$^{04}$ are bonded to each other to form an aromatic ring. The aromatic ring may have a substituent. R$^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group.

In General Formula (d0), $R^{o1}$, $R^{o2}$, $R^{o3}$ and $R^{o4}$ each independently represent a hydrogen atom, a hydroxy group, a halogen atom, or an alkyl group having 1 to 5 carbon atoms. In General Formula (d0), examples of the halogen atom as R01, $R^{o2}$, $R^{o3}$, and $R^{o4}$ include a fluorine atom, a chlorine atom, a bromine atom, and an iodine atom, and among these, a fluorine atom is preferable from the viewpoint of hydrophobicity.

In General Formula (d0), $R^{o1}$ and $R^{o2}$, $R^{o2}$ and $R^{o3}$, or $R^{o3}$ and $R^{o4}$ are bonded to each other to form an aromatic ring. The aromatic ring that is formed by bonding $R^{o1}$ and $R^{o2}$, $R^{o2}$ and $R^{o3}$, or $R^{o3}$ and $R^{o4}$ to each other is not particularly limited as long as it is a cyclic conjugated system having (4n+2) π electrons, and may be monocyclic or polycyclic. The aromatic ring is preferably formed of 5 to 30 carbon atoms, more preferably 5 to 20 carbon atoms, still more preferably 6 to 15 carbon atoms, and particularly preferably 6 to 12 carbon atoms. For example, in a case where $R^{o1}$ and $R^{o2}$ are bonded to each other to form an aromatic ring, an aromatic ring containing two carbons (carbons that form a benzene ring) to which $R^{o1}$ and $R^{o2}$ are each bonded is formed. The same applies to the case where $R^{o2}$ and $R^{o3}$ or $R^{o3}$ and $R^{o4}$ are bonded to each other to form an aromatic ring.

In General Formula (d0), specific examples of the aromatic ring that is formed by bonding $R^{o1}$ and $R^{o2}$, $R^{o2}$ and $R^{o3}$, or $R^{o3}$ and $R^{o4}$ to each other include aromatic hydrocarbon rings such as benzene, fluorene, naphthalene, anthracene, and phenanthrene; and aromatic heterocyclic rings in which a part of carbon atoms constituting the above-described aromatic hydrocarbon rings have been substituted with a hetero atom. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Among these, the aromatic ring in General Formula (d0) is preferably an aromatic hydrocarbon ring, more preferably benzene or naphthalene, and particularly preferably benzene since the effects of the present invention are further enhanced.

In General Formula (d0), the aromatic ring that is formed by bonding $R^{o1}$ and $R^{o2}$, $R^{o2}$ and $R^{o3}$, or $R^{o3}$ and $R^{o4}$ to each other may have a substituent. Examples of the substituent which may be contained in the aromatic ring that is formed by bonding $R^{o1}$ and $R^{o2}$, $R^{o2}$ and $R^{o3}$, or $R^{o3}$ and $R^{o4}$ to each other include the same substituent as the substituent which may be contained in the cyclic hydrocarbon group as $Ra'^{3}$ described above. That is, examples of the substituent which the cyclic hydrocarbon group as $Ra'^{3}$ may have include —$R^{P1}$, —$R^{P2}$—O—$R^{P1}$, —$R^{P2}$—CO—$R^{P1}$, —$R^{P2}$—CO—O$R^{P1}$, —$R^{P2}$—O—CO—$R^{P1}$, —$R^{P2}$—OH, —$R^{P2}$—CN, and —$R^{P2}$—COOH (hereinafter, these substituents are also collectively referred to as "$Ra^{x5}$").

In General Formula (d0), Y represents a group that forms an alicyclic group together with *C (a carbon atom). The alicyclic group may be polycyclic or monocyclic. In the present embodiment, Y is preferably a monocyclic alicyclic group. Further, the alicyclic group that is formed by Y is preferably a saturated hydrocarbon group.

In Y in General Formula (d0), in a case of including the two carbon atoms of the benzene ring adjacent to Y and *C (a carbon atom) that forms Y, the number of carbon atoms of the carbon atoms which form the alicyclic group is preferably in a range of 4 to 8, more preferably in a range of 5 to 7, and still more preferably 5 or 6. That is, the alicyclic group that is formed by Y is preferably a 4- to 8-membered ring, more preferably a 5- to 7-membered ring, and still more preferably a 5- or 6-membered ring.

In General Formula (d0), the alicyclic group that is formed by Y may have a substituent. Examples of the substituent which Y may have include the same group as the substituent which the cyclic hydrocarbon group as $Ra'^{3}$ may have.

Further, in Y in General Formula (d0), at least one of the carbon atoms that form the alicyclic group is substituted with an ether bond, a thioether bond, a carbonyl group, a sulfinyl group, or a sulfonyl group. Among the carbon atoms that form the alicyclic group as Y, the number of carbon atoms that are substituted with an ether bond, a thioether bond, a carbonyl group, a sulfinyl group, or a sulfonyl group is preferably at least one, more preferably two or more, and particularly preferably two.

Specific examples of the preferred anion moiety in General Formula (d0) are shown below.

[Chemical Formula 43]

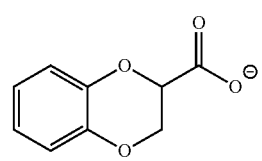

(d-1)

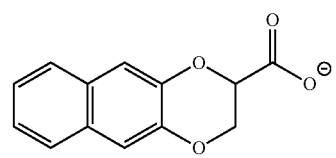

(d-2)

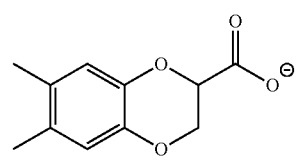

(d-3)

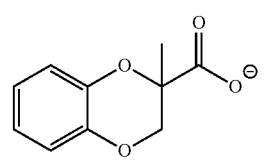

(d-4)

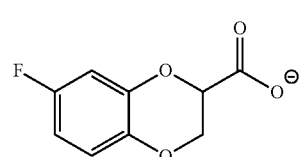

(d-5)

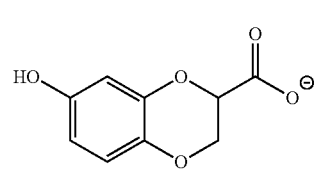

(d-6)

(d-7)
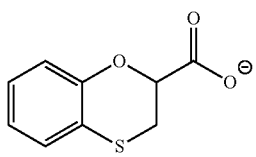
(d-8)
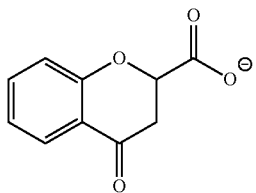
[Chemical Formula 44]
(d-9)
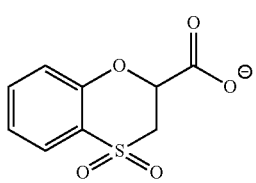
(d-10)
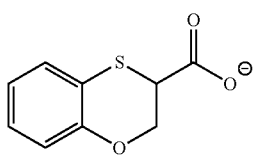
(d-11)
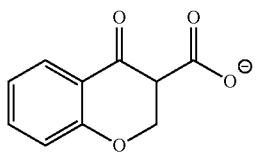
(d-12)
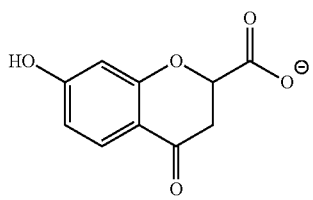
(d-13)
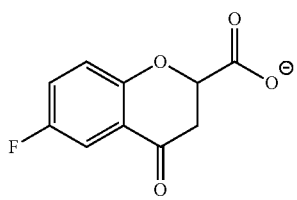
(d-14)
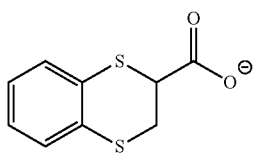
(d-15)
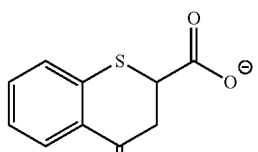
(d-16)
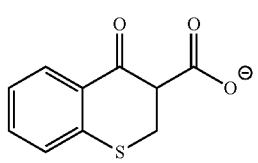
[Chemical Formula 45]
(d-17)
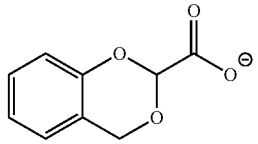
(d-18)
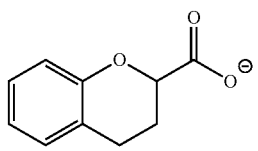
(d-19)
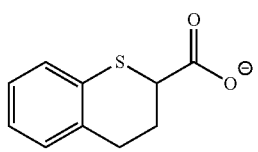
(d-20)
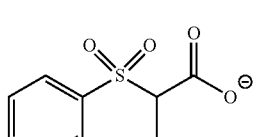
(d-21)
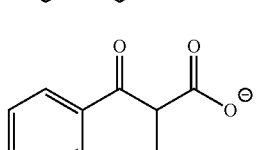
(d-22)
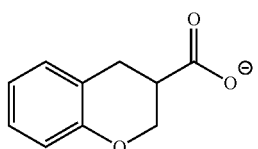
(d-23)

-continued
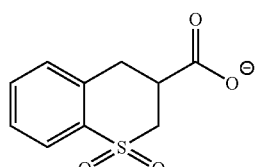
(d-24)
[Chemical Formula 46]
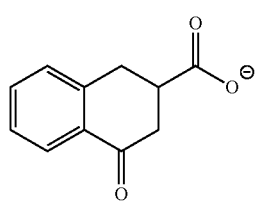
(d-25)
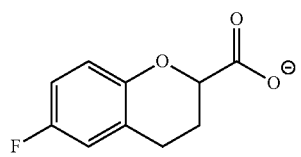
(d-26)
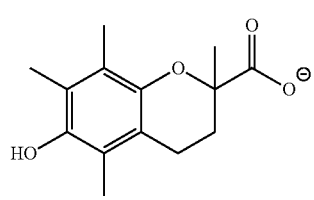
(d-27)
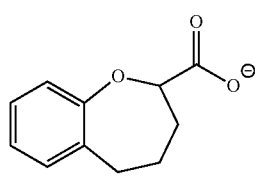
(d-28)
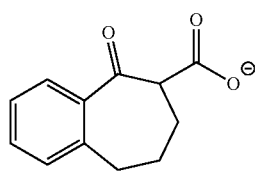
(d-29)
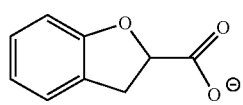
(d-30)
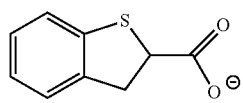
(d-31)
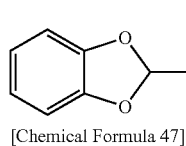
(d-32)
[Chemical Formula 47]
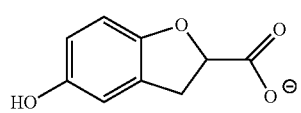
(d-33)
-continued
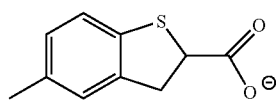
(d-34)
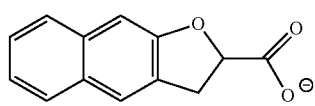
(d-35)
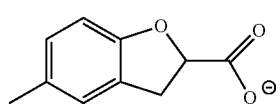
(d-36)
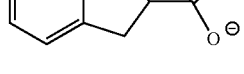
(d-37)
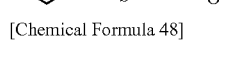
(d-38)
[Chemical Formula 48]
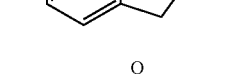
(d-39)
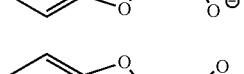
(d-40)
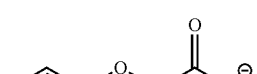
(d-41)
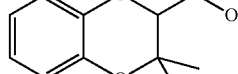
(d-42)
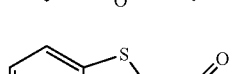
(d-43)
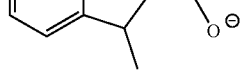
(d-44)

(d-45)

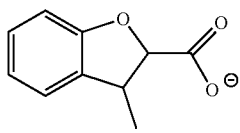

Even in the above anions, among the carbon atoms that form the alicyclic group as Y in General Formula (d0), the number of carbon atoms that are substituted with an ether bond, a thioether bond, a carbonyl group, a sulfinyl group, or a sulfonyl group is preferably at least one and more preferably two or more.

Among the specific examples of the above anions, Chemical Formula (d-1), (d-3), (d-7), (d-8), (d-9), (d-18), (d-31), or (d-32) is preferable.

<<$(M^{m+})_{1/m}$ in General Formula (d0): Cation Moiety>>

In General Formula (d0), $M^{m+}$ represents an m-valent organic cation.

The organic cation as $M^{m+}$ is preferably an onium cation and more preferably a sulfonium cation or an iodonium cation. m represents an integer of 1 or greater.

Preferred examples of the cation moiety $((M^{m+})_{1/m})$ include organic cations each represented by General Formulae (ca-1) to (ca-5).

[Chemical Formula 49]

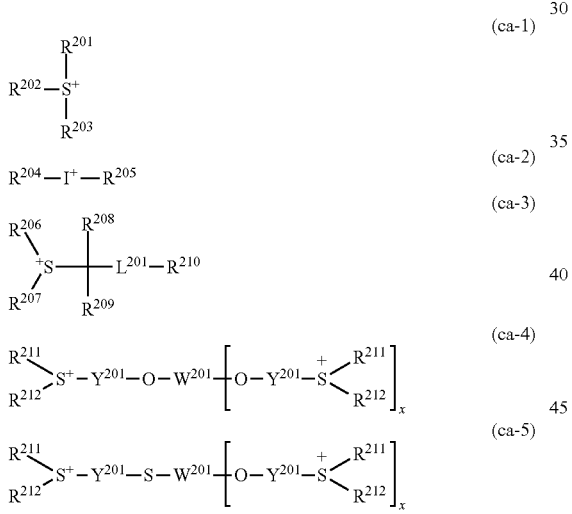

[In the formula, $R^{201}$ to $R^{207}$, $R^{211}$, and $R^{212}$ each independently represent an aryl group, an alkyl group, or an alkenyl group, each of which may have a substituent. $R^{201}$ to $R^{203}$, $R^{206}$ and $R^{207}$, or $R^{211}$ and $R^{212}$ may be bonded to each other to form a ring together with the sulfur atoms in the formulae. $R^{208}$ and $R^{209}$ each independently represent a hydrogen atom or an alkyl group having 1 to 5 carbon atoms. $R^{210}$ represents an aryl group which may have a substituent, an alkyl group which may have a substituent, an alkenyl group which may have a substituent, or a —$SO_2$—containing cyclic group which may have a substituent. $L^{201}$ represents —C(=O)— or —C(=O)—O—. $Y^{201}$s each independently represent an arylene group, an alkylene group, or an alkenylene group. x represents 1 or 2. $W^{201}$ represents an (x+1)-valent linking group.]

In General Formulae (ca-1) to (ca-5), examples of the aryl group as $R^{201}$ to $R^{207}$, $R^{211}$, and $R^{212}$ include an unsubstituted aryl group having 6 to 20 carbon atoms, and a phenyl group or a naphthyl group is preferable.

The alkyl group as $R^{201}$ to $R^{207}$, $R^{211}$, and $R^{212}$ is preferably a chain-like or cyclic alkyl group preferably has 1 to 30 carbon atoms.

The alkenyl group as $R^{201}$ to $R^{207}$, $R^{211}$, and $R^{212}$ preferably has 2 to 10 carbon atoms.

Examples of the substituent which may be included in $R^{201}$ to $R^{207}$ and $R^{210}$ to $R^{212}$ include an alkyl group, a halogen atom, a halogenated alkyl group, a carbonyl group, a cyano group, an amino group, an aryl group, and groups each represented by General Formulae (ca-r-1) to (ca-r-7) shown above.

[Chemical Formula 50]

| | [ca-r-1] |
|---|---|
| —O—R'$^{201}$ | |

[ca-r-2]

—O—C(=O)—O—R'$^{201}$

[ca-r-3]

—O—C(=O)—R'$^{201}$

[ca-r-4]

—O—CH$_2$—O—R'$^{201}$

[ca-r-5]

—O—C(=O)—CH$_2$—O—C(=O)—R'$^{201}$

[ca-r-6]

—O—S(=O)$_2$—R'$^{201}$

[ca-r-7]

—O—CH$_2$—C(=O)—O—CH$_2$—C(=O)—O—R'$^{201}$

[In the formulae, R'$^{201}$s each independently represent a hydrogen atom, a cyclic group which may have a substituent, a chain-like alkyl group which may have a substituent, or a chain-like alkenyl group which may have a substituent.]

Cyclic Group which may have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated. In general, it is preferable that the aliphatic hydrocarbon group be saturated.

The aromatic hydrocarbon group as R'$^{201}$ is a hydrocarbon group having an aromatic ring. The aromatic hydrocarbon group preferably has 3 to 30 carbon atoms, more preferably 5 to 30 carbon atoms, still more preferably 5 to 20 carbon atoms, particularly preferably 6 to 15 carbon atoms, and most preferably 6 to 10 carbon atoms. Here, the number of carbon atoms in a substituent is not included in the number of carbon atoms.

Specific examples of the aromatic ring which the aromatic hydrocarbon group has as $R'^{201}$ include benzene, fluorene, naphthalene, anthracene, phenanthrene, biphenyl, or an aromatic heterocyclic ring in which some carbon atoms constituting any of these aromatic rings have been substituted with a hetero atom. Examples of the hetero atom in the aromatic heterocyclic rings include an oxygen atom, a sulfur atom, and a nitrogen atom.

Specific examples of the aromatic hydrocarbon group as $R'^{201}$ include a group in which one hydrogen atom has been removed from the above-described aromatic ring (an aryl group such as a phenyl group or a naphthyl group) and a group in which one hydrogen atom in the aromatic ring has been substituted with an alkylene group (an arylalkyl group such as a benzyl group, a phenethyl group, a 1-naphthylmethyl group, a 2-naphthylmethyl group, 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

Examples of the cyclic aliphatic hydrocarbon group as $R'^{201}$ include aliphatic hydrocarbon groups containing a ring in the structure thereof.

Examples of the aliphatic hydrocarbon group containing a ring in the structure thereof include an alicyclic hydrocarbon group (a group in which one hydrogen atom has been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group in which one or more hydrogen atoms have been removed from a monocycloalkane. The monocycloalkane preferably has 3 to 6 carbon atoms, and specific examples thereof include cyclopentane and cyclohexane. The polycyclic alicyclic hydrocarbon group is preferably a group in which one or more hydrogen atoms have been removed from a polycycloalkane, and the polycycloalkane preferably has 7 to 30 carbon atoms. Among polycycloalkanes, a polycycloalkane having a bridged ring-based polycyclic skeleton, such as adamantane, norbornane, isobornane, tricyclodecane, or tetracyclododecane, and a polycycloalkane having a condensed ring-based polycyclic skeleton, such as a cyclic group having a steroid skeleton are preferable.

Among them, the cyclic aliphatic hydrocarbon group as $R'^{201}$ is preferably a group in which one or more hydrogen atoms have been removed from a monocycloalkane or a polycycloalkane, more preferably a group in which one hydrogen atom has been removed from a polycycloalkane, particularly preferably an adamantyl group or a norbornyl group, and most preferably an adamantyl group.

The linear or branched aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and particularly preferably 1 to 3 carbon atoms.

The linear aliphatic hydrocarbon group is preferably a linear alkylene group, and specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The branched aliphatic hydrocarbon group is preferably a branched alkylene group, and specific examples thereof include alkylalkylene groups, for example, alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. The alkyl group in the alkylalkylene group is preferably a linear alkyl group having 1 to 5 carbon atoms.

The cyclic hydrocarbon group as $R'^{201}$ may contain a hetero atom such as a heterocyclic ring. Specific examples thereof include lactone-containing cyclic groups each represented by General Formulae (a2-r-1) to (a2-r-7), —SO$_2$—-containing cyclic groups each represented by General Formulae (a5-r-1) to (a5-r-4), and other heterocyclic groups each represented by Chemical Formulae (r-hr-1) to (r-hr-16).

Examples of the substituent of the cyclic group as $R'^{201}$ include an alkyl group, an alkoxy group, a halogen atom, a halogenated alkyl group, a hydroxyl group, a carbonyl group, and a nitro group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

The halogen atom as the substituent is preferably a fluorine atom.

Examples of the above-described halogenated alkyl group as the substituent include a group in which part or all of hydrogen atoms in an alkyl group having 1 to 5 carbon atoms such as a methyl group, an ethyl group, a propyl group, an n-butyl group, or a tert-butyl group have been substituted with the above-described halogen atom.

The carbonyl group as the substituent is a group that substitutes a methylene group (—CH$_2$—) constituting the cyclic hydrocarbon group.

Chain-Like Alkyl Group which may have Substituent:

The chain-like alkyl group as $R'^{201}$ may be linear or branched.

The linear alkyl group preferably has 1 to 20 carbon atoms, more preferably 1 to 15 carbon atoms, and most preferably 1 to 10 carbon atoms.

The branched alkyl group preferably has 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which may have Substituent:

Such a chain-like alkenyl group as $R'^{201}$ may be linear or branched, preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the above, the chain-like alkenyl group is preferably a linear alkenyl group, more preferably a vinyl group or a propenyl group, and particularly preferably a vinyl group.

Examples of the substituent in the chain-like alkyl group or alkenyl group as $R'^{201}$, an alkoxy group, a halogen atom, a halogenated alkyl group, a hydroxyl group, a carbonyl group, a nitro group, an amino group, a cyclic group as $R'^{201}$ or the like may be used.

As the cyclic group which may have a substituent, the chain-like alkyl group which may have a substituent, or the chain-like alkenyl group which may have a substituent, as $R'^{201}$, a group that is the same as the acid-dissociable group represented by above-described General Formula (a1-r-2) can be mentioned as the cyclic group which may have a substituent or the chain-like alkyl group which may have a substituent, in addition to the groups described above.

Among them, $R'^{201}$ is preferably a cyclic group which may have a substituent and more preferably a cyclic hydrocarbon group which may have a substituent. More specific examples thereof preferably include a phenyl group, a naphthyl group, a group in which one or more hydrogen atoms have been removed from a polycycloalkane, lactone-containing cyclic groups each represented by any of General Formulae (a2-r-1) to (a2-r-7), and —$SO_2$—-containing cyclic groups each represented by any of General Formulae (a5-r-1) to (a5-r-4).

In General Formulae (ca-1) to (ca-5), in a case where $R^{201}$ to $R^{203}$, $R^{206}$ and $R^{207}$, or $R^{211}$ and $R^{212}$ are bonded to each other to form a ring with a sulfur atom in the formula, these groups may be bonded to each other via a hetero atom such as a sulfur atom, an oxygen atom or a nitrogen atom, or a functional group such as a carbonyl group, —SO—, —$SO_2$—, —$SO_3$—, —COO—, —CONH—, or —N($R_N$)— (here, $R_N$ represents an alkyl group having 1 to 5 carbon atoms). As the ring to be formed, a ring containing the sulfur atom in the formula in the ring skeleton thereof is preferably a 3- to 10-membered ring and particularly preferably a 5- to 7-membered ring including the sulfur atom. Specific examples of the ring to be formed include a thiophene ring, a thiazole ring, a benzothiophene ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represent a hydrogen atom or an alkyl group having 1 to 5 carbon atoms and are preferably a hydrogen atom or an alkyl group having 1 to 3 carbon atoms. In a case where $R^{208}$ and $R^{209}$ each independently represent an alkyl group, $R^{208}$ and $R^{209}$ may be bonded to each other to form a ring.

$R^{210}$ represents an aryl group which may have a substituent, an alkyl group which may have a substituent, an alkenyl group which may have a substituent, or a —$SO_2$—-containing cyclic group which may have a substituent.

Examples of the aryl group as $R^{210}$ include an unsubstituted aryl group having 6 to 20 carbon atoms, and a phenyl group or a naphthyl group is preferable.

The alkyl group as $R^{210}$, a chain-like or cyclic alkyl group having 1 to 30 carbon atoms is preferable.

The alkenyl group as $R^{210}$ preferably has 2 to 10 carbon atoms.

The —$SO_2$—-containing cyclic group which may have a substituent, as $R^{210}$, is preferably a "—$SO_2$—-containing polycyclic group", and more preferably a group represented by General Formula (a5-r-1).

$Y^{201}$s each independently represent an arylene group, an alkylene group, or an alkenylene group.

Examples of the arylene group as $Y^{201}$ include groups in which one hydrogen atom has been removed from an aryl group mentioned as the aromatic hydrocarbon group represented by $R^{101}$ in General Formula (b-1) described above.

Examples of the alkylene group and alkenylene group as $Y^{201}$ include groups in which one hydrogen atom has been removed from the chain-like alkyl group or the chain-like alkenyl group as $R^{101}$ in General Formula (b-1) described above.

In General Formula (ca-4), x represents 1 or 2.

$W^{201}$ represents an (x+1)-valent linking group, that is, a divalent or trivalent linking group.

The divalent linking group as $W^{201}$ is preferably a divalent hydrocarbon group which may have a substituent, and as examples thereof include the same divalent hydrocarbon group, which may have a substituent, as $Ya^{21}$ in General Formula (a2-1). The divalent linking group as $W^{201}$ may be linear, branched, or cyclic and is preferably cyclic. Among these, an arylene group having both terminals at which two carbonyl groups are combined is preferable. Examples of the arylene group include a phenylene group and a naphthylene group, and a phenylene group is particularly preferable.

Examples of the trivalent linking group as $W^{201}$ include a group in which one hydrogen atom has been removed from the above-described divalent linking group as $W^{201}$ and a group in which the divalent linking group has been bonded to another divalent linking group. The trivalent linking group as $W^{201}$ is preferably a group in which two carbonyl groups are bonded to an arylene group.

Specific examples of the suitable cation represented by Chemical Formula (ca-1) include cations each represented by General Formulae (ca-1-1) to (ca-1-71) shown below.

[Chemical Formula 51]

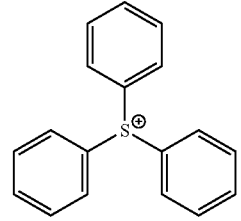

(ca-1-1)

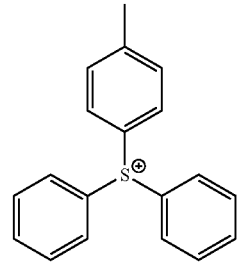

(ca-1-2)

(ca-1-3)
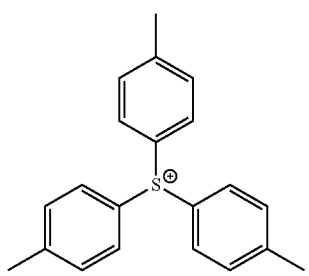
(ca-1-4)
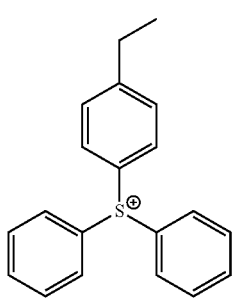
(ca-1-5)
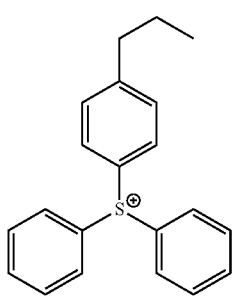
(ca-1-6)
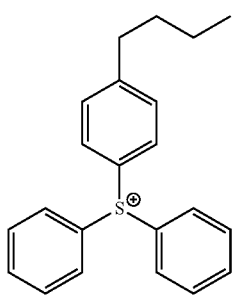
(ca-1-7)
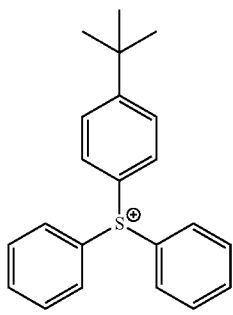
(ca-1-8)
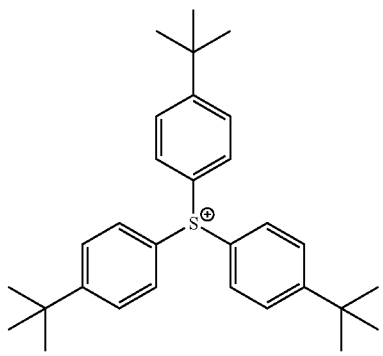
(ca-1-9)
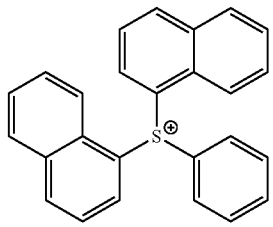
(ca-1-10)
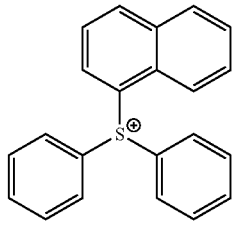
(ca-1-11)
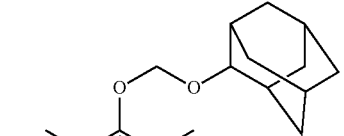
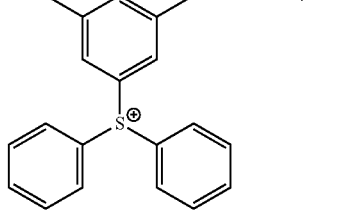
(ca-1-12)
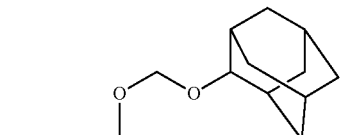
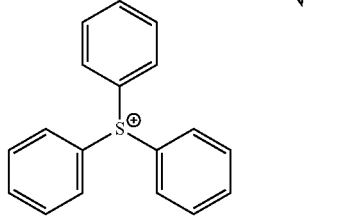

-continued
(ca-1-13)
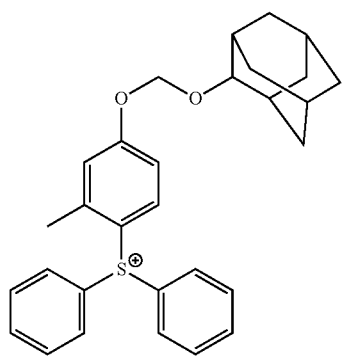
(ca-1-14)
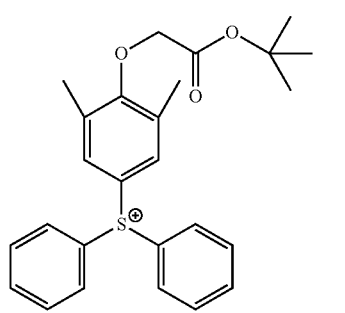
(ca-1-15)
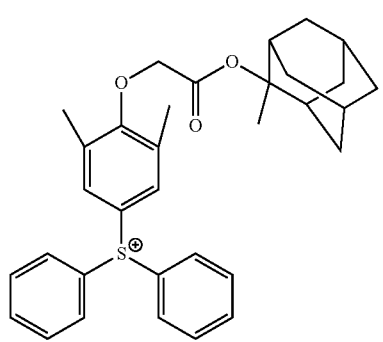
(ca-1-16)
-continued
[Chemical Formula 52]
(ca-1-17)
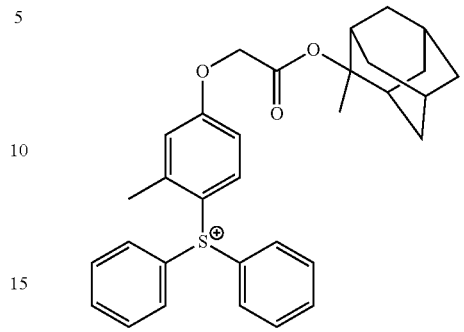
(ca-1-18)
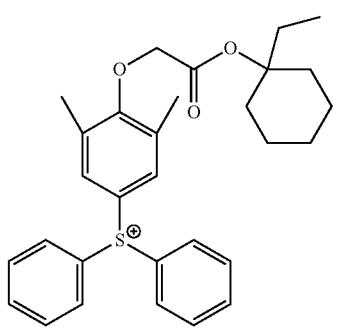
(ca-1-19)
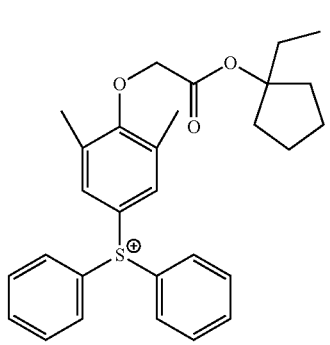
(ca-1-20)
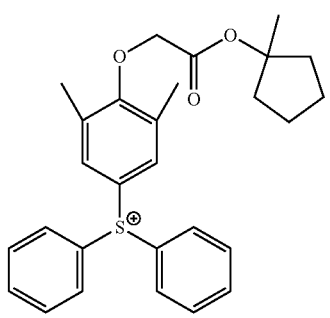

(ca-1-21) 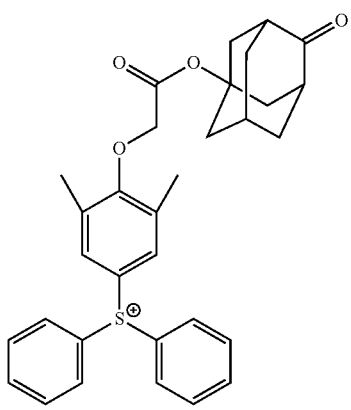
(ca-1-25) 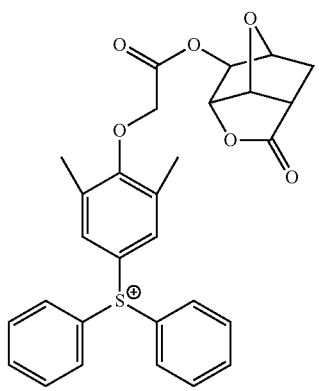
(ca-1-22) 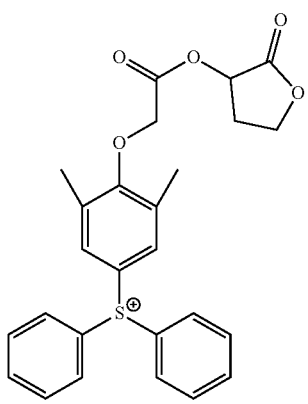
(ca-1-26) 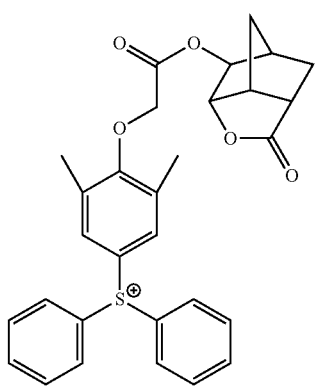
(ca-1-23) 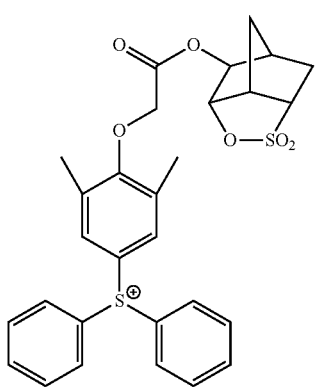
(ca-1-27) 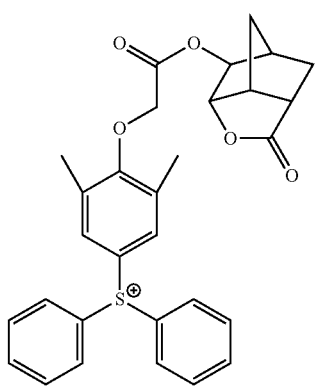
(ca-1-24)
(ca-1-28) 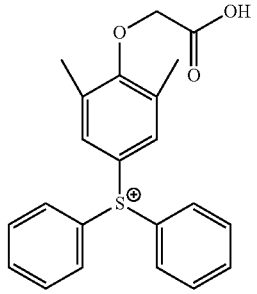

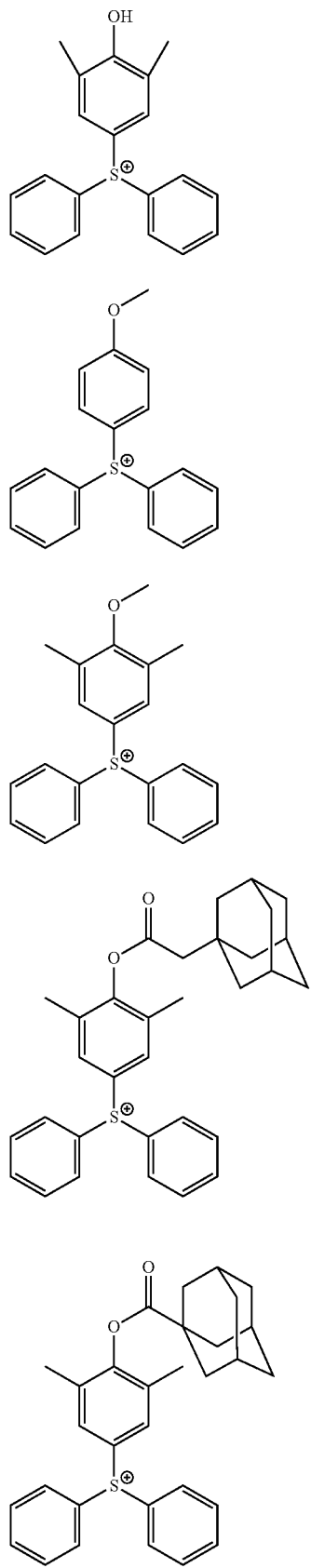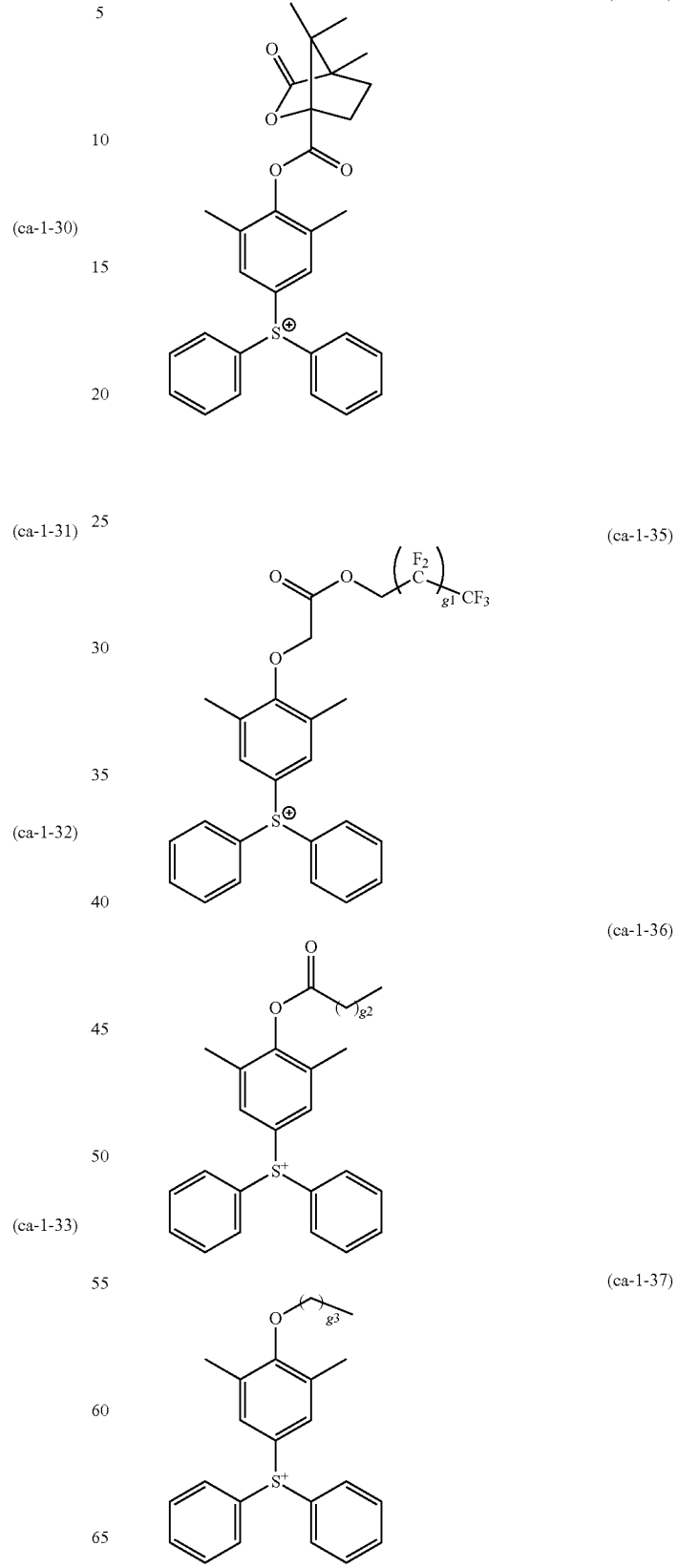

(ca-1-38)
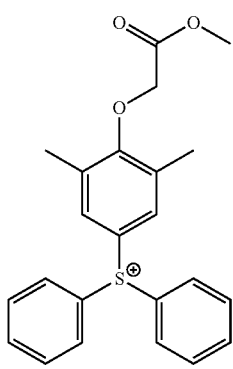
(ca-1-39)
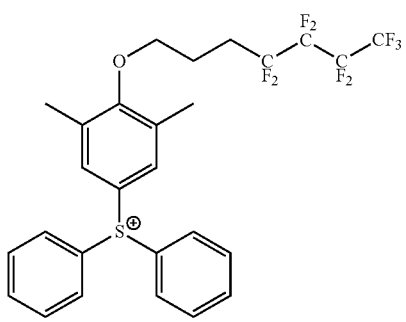
(ca-1-40)
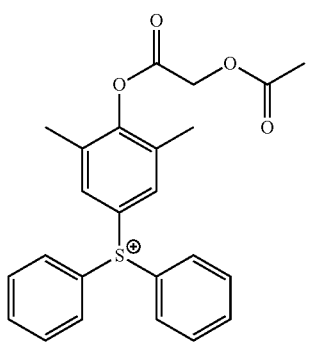
(ca-1-41)
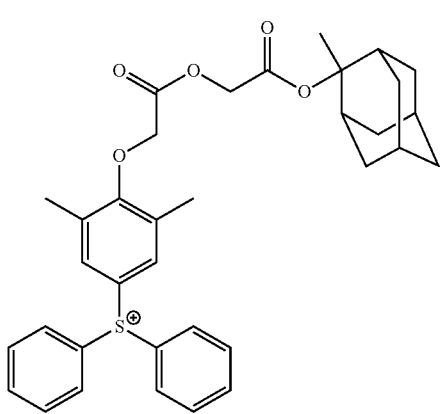
(ca-1-42)
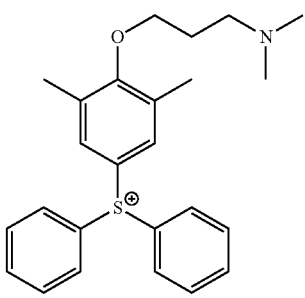
(ca-1-43)
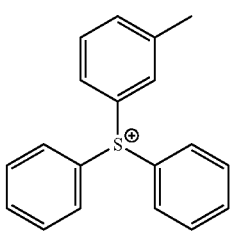
(ca-1-44)
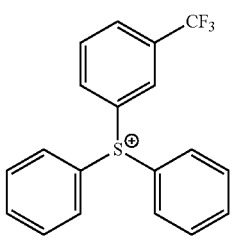
(ca-1-45)
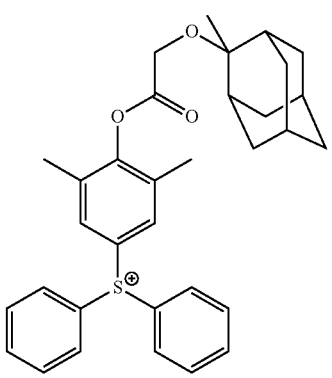
(ca-1-46)
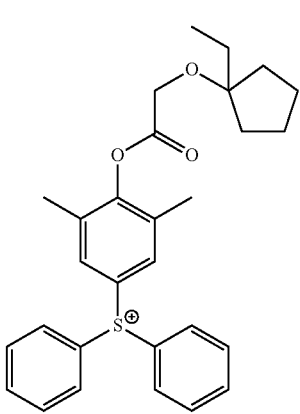

(ca-1-47)
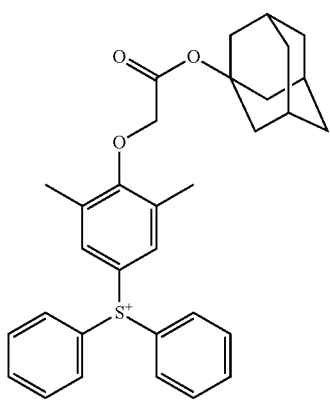
[In the formula, g1, g2, and g3 represent the numbers of repetitions, g1 is an integer in a range of 1 to 5, g2 is an integer in a range of 0 to 20, and g3 is an integer in a range of 0 to 20.]
[Chemical Formula 54]
(ca-1-48)
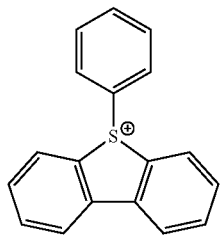
(ca-1-49)
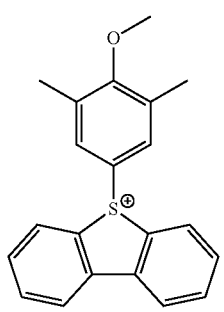
(ca-1-50)
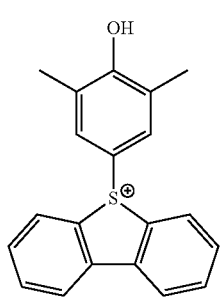
(ca-1-51)
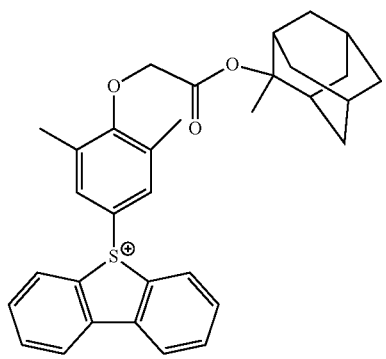
(ca-1-52)
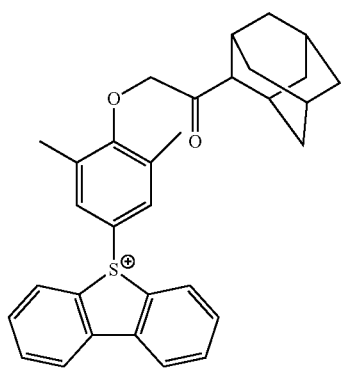
(ca-1-53)
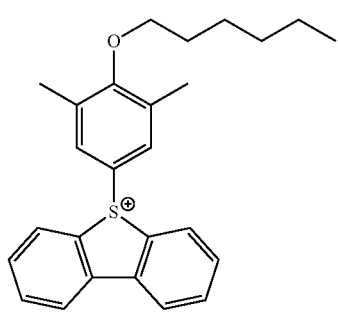
(ca-1-54)
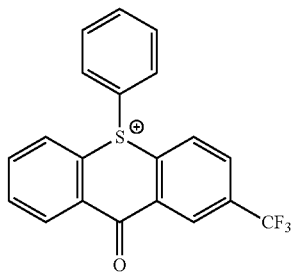
[Chemical Formula 55]
(ca-1-55)
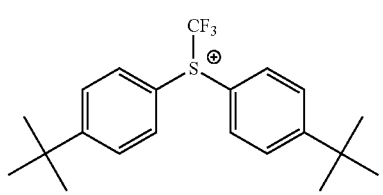

-continued (ca-1-56)

(ca-1-57)

(ca-1-58)

(ca-1-59)

(ca-1-60)

(ca-1-61)

[Chemical Formula 56]

(ca-1-62)

(ca-1-63)

-continued (ca-1-64)

(ca-1-65)

(ca-1-66)

(ca-1-67)

-continued

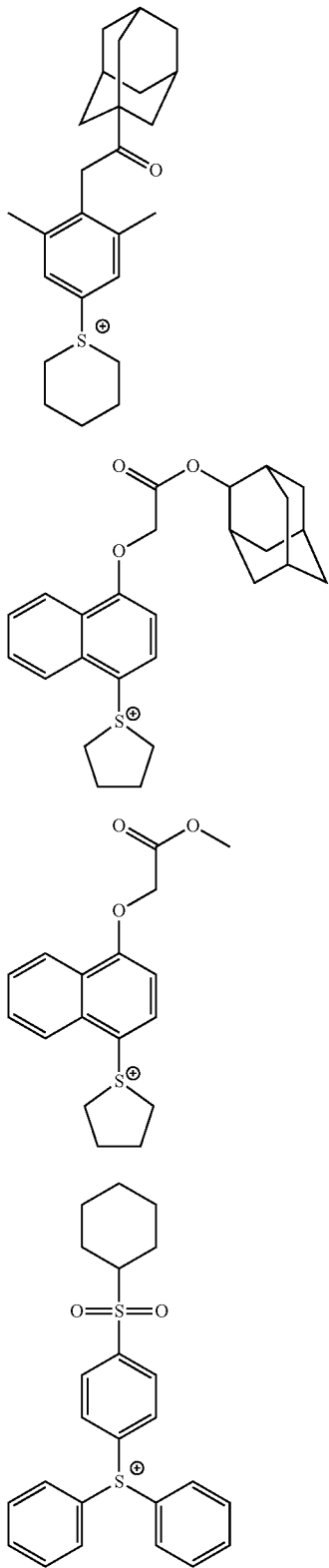

(ca-1-68)

(ca-1-69)

(ca-1-70)

(ca-1-71)

[In the formula, R″²⁰¹ represents a hydrogen atom or a substituent, and examples of the substituent include the same substituent as that exemplified as the substituent which $R^{201}$ to $R^{207}$ and $R^{210}$ to $R^{212}$ may have.]

Specific examples of suitable cations represented by General Formula (ca-2) include a diphenyliodonium cation and a bis(4-tert-butylphenyl)iodonium cation.

Specific examples of the suitable cations each represented by General Formula (ca-3) include cations each represented by General Formulae (ca-3-1) to (ca-3-6) shown below.

[Chemical Formula 57]

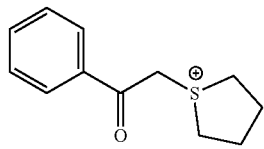

(ca-3-1)

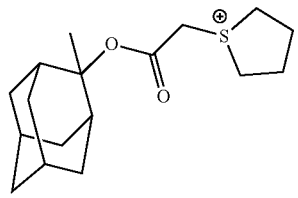

(ca-3-2)

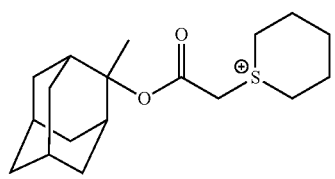

(ca-3-3)

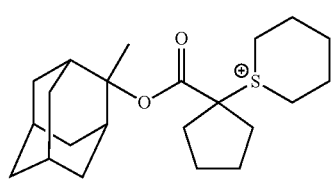

(ca-3-4)

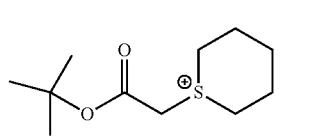

(ca-3-5)

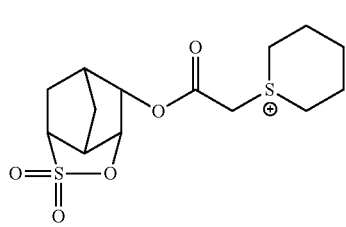

(ca-3-6)

Specific examples of the suitable cations each represented by General Formula (ca-4) include cations each represented by General Formulae (ca-4-1) and (ca-4-2) shown below.

[Chemical Formula 58]
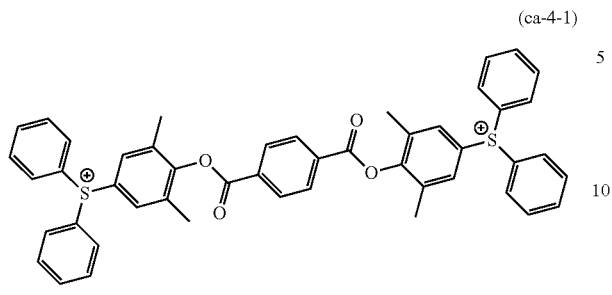
(ca-4-1)
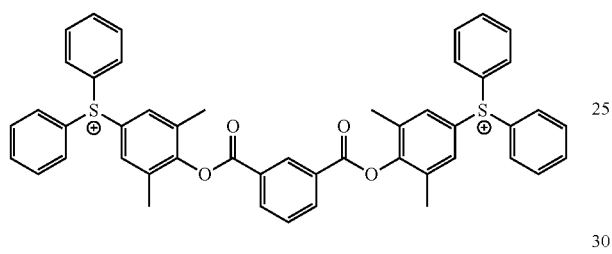
(ca-4-2)
Specific examples of the suitable cations each represented by General Formula (ca-5) include cations each represented by General Formulae (ca-5-1) to (ca-5-3) shown below.
[Chemical Formula 59]
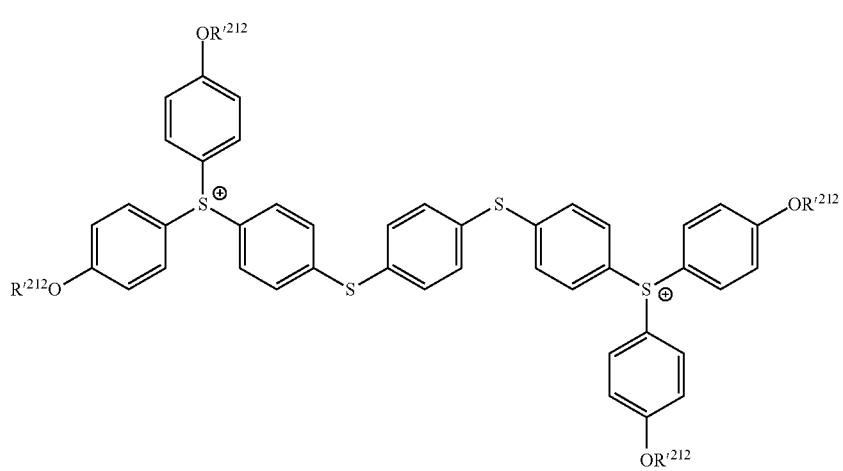
(ca-5-1)

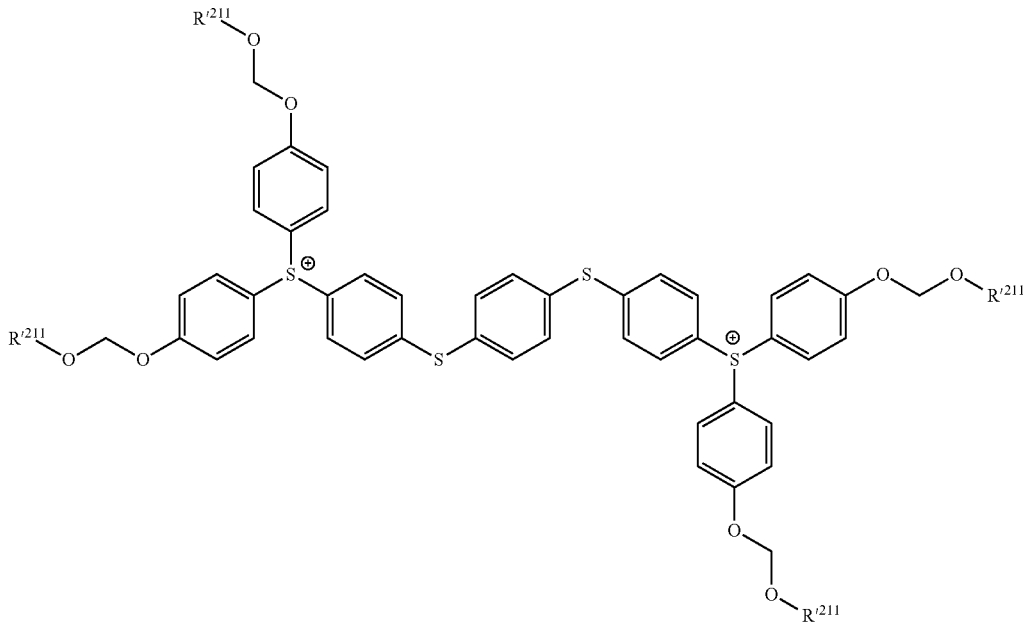

(ca-5-2)

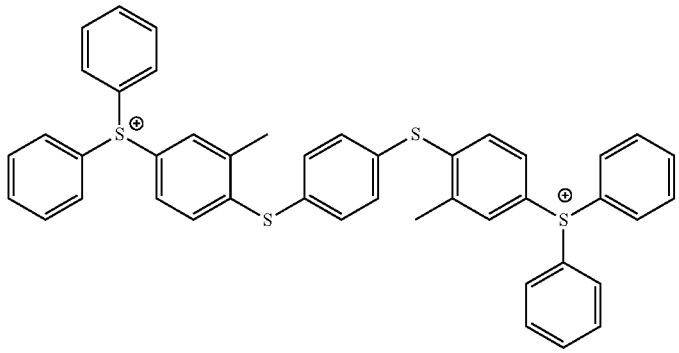

(ca-5-3)

Among the above cations, as the cation moiety $((M^{m+})_{1/m})$, a cation represented by General Formula (ca-1) is preferable.

In the resist composition according to the present embodiment, the component (D0) may be used alone or in a combination of two or more kinds thereof.

The content of the component (D0) in the resist composition is preferably in a range of 1 to 35 parts by mass, more preferably in a range of 2 to 25 parts by mass, still more preferably in a range of 3 to 15 parts by mass, and particularly preferably in a range of 3 to 10 parts by mass, with respect to 100 parts by mass of the component (A).

In a case where the content of the component (D0) is set to be equal to or lower than the above upper limit value, pattern formation can be sufficiently carried out. Further, in a case where the content of the component (D0) is set to be equal to or greater than the above lower limit value, the fine resolution is enhanced.

<Optional Component>

The resist composition according to the present embodiment may further contain another component (an optional component) in addition to the component (A) and the component (D0) which are described above. Examples of the optional component include the component (B), a component (D), a component (E), a component (F), and a component (S), which are described below.

<<Acid Generator Component (B)>>

The resist composition according to the present embodiment may further contain an acid generator component (B) (hereinafter, referred to as a "component (B)") generating an acid upon exposure, in addition to the component (A). However, the compound (D0) is excluded from the component (B).

The component (B) is not particularly limited, and those which have been proposed as an acid generator for a chemical amplification-type resist composition in the related art can be used.

Examples of such an acid generator are numerous and include onium salt-based acid generators such as an iodonium salt and a sulfonium salt; an oxime sulfonate-based acid generator; diazomethane-based acid generators such as bisalkyl or bisaryl sulfonyl diazomethanes and poly(bissulfonyl)diazomethanes; nitrobenzyl sulfonate-based acid generators; iminosulfonate-based acid generators; and disulfone-based acid generators.

Examples of the onium salt-based acid generator include a compound represented by General Formula (b-1) (hereinafter, also referred to as a "component (b-1)"), a compound represented by General Formula (b-2) (hereinafter, also referred to as a "component (b-2)"), and a compound represented by General Formula (b-3) (hereinafter, also referred to as a "component (b-3)").

[Chemical Formula 60]

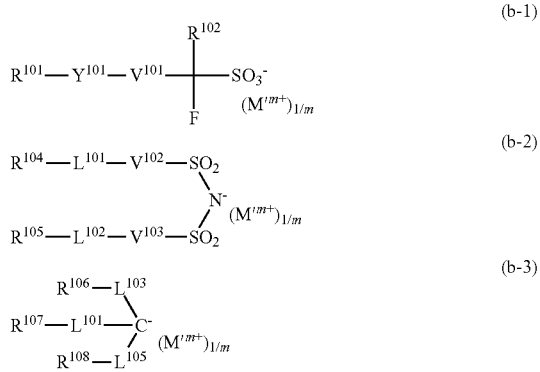

[In the formulae, $R^{101}$ and $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other to form a ring structure. $R^{102}$ represents a fluorinated alkyl group having 1 to 5 carbon atoms or a fluorine atom. $Y^{101}$ represents a divalent linking group containing an oxygen atom or a single bond. $V^{101}$ to $V^{103}$ each independently represents a single bond, an alkylene group, or a fluorinated alkylene group. $L^{101}$ and $L^{102}$ each independently represent a single bond or an oxygen atom. $L^{103}$ to $L^{105}$ each independently represents a single bond, —CO—, or —SO$_2$—. m represents an integer of 1 or greater, and represents an m-valent onium cation.]

{Anion Moiety}

Anion in Component (b-1)

In General Formula (b-1), $R^{101}$ represents a cyclic group which may have a substituent, a chain-like alkyl group which may have a substituent, or a chain-like alkenyl group which may have a substituent.

Cyclic Group which may have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated. In general, it is preferable that the aliphatic hydrocarbon group be saturated.

The aromatic hydrocarbon group as $R^{101}$ is a hydrocarbon group having an aromatic ring. The aromatic hydrocarbon group preferably has 3 to 30 carbon atoms, more preferably 5 to 30, still more preferably 5 to 20, particularly preferably 6 to 15, and most preferably 6 to 10. Here, the number of carbon atoms in a substituent is not included in the number of carbon atoms.

Specific examples of the aromatic ring the aromatic hydrocarbon group has as $R^{101}$ include benzene, fluorene, naphthalene, anthracene, phenanthrene, biphenyl, or an aromatic heterocyclic ring in which some carbon atoms constituting any of these aromatic rings have been substituted with a hetero atom. Examples of the hetero atom in the aromatic heterocyclic rings include an oxygen atom, a sulfur atom, and a nitrogen atom.

Specific examples of the aromatic hydrocarbon group as $R^{101}$ include a group in which one hydrogen atom has been removed from the above-described aromatic ring (an aryl group such as a phenyl group or a naphthyl group) and a group in which one hydrogen atom in the aromatic ring has been substituted with an alkylene group (an arylalkyl group such as a benzyl group, a phenethyl group, a 1-naphthylmethyl group, a 2-naphthylmethyl group, 1-naphthylethyl group, or a 2-naphthylethyl group). The alkylene group (an alkyl chain in the arylalkyl group) preferably has 1 to 4 carbon atoms, more preferably 1 or 2 carbon atoms, and particularly preferably 1 carbon atom.

Examples of the cyclic aliphatic hydrocarbon group as $R^{101}$ include aliphatic hydrocarbon groups containing a ring in the structure thereof.

Examples of the aliphatic hydrocarbon group containing a ring in the structure thereof include an alicyclic hydrocarbon group (a group in which one hydrogen atom has been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed in a linear or branched aliphatic hydrocarbon group.

The alicyclic hydrocarbon group preferably has 3 to 20 carbon atoms and more preferably 3 to 12 carbon atoms.

The alicyclic hydrocarbon group may be a polycyclic group or a monocyclic group. The monocyclic alicyclic hydrocarbon group is preferably a group in which one or more hydrogen atoms have been removed from a monocycloalkane. The monocycloalkane preferably has 3 to 6 carbon atoms, and specific examples thereof include cyclopentane and cyclohexane. The polycyclic alicyclic hydrocarbon group is preferably a group in which one or more hydrogen atoms have been removed from a polycycloalkane, and the polycycloalkane preferably has 7 to 30 carbon atoms. Among polycycloalkanes, a polycycloalkane having a bridged ring-based polycyclic skeleton, such as adamantane, norbornane, isobornane, tricyclodecane, or tetracyclododecane, and a polycycloalkane having a condensed ring-based polycyclic skeleton, such as a cyclic group having a steroid skeleton are preferable.

Among them, the cyclic aliphatic hydrocarbon group as $R^{101}$ is preferably a group in which one or more hydrogen atoms have been removed from a monocycloalkane or a polycycloalkane, more preferably a group in which one hydrogen atom has been removed from a polycycloalkane, particularly preferably an adamantyl group or a norbornyl group, and most preferably an adamantyl group.

The linear aliphatic hydrocarbon group which may be bonded to the alicyclic hydrocarbon group preferably has 1 to 10 carbon atoms, more preferably 1 to 6 carbon atoms, still more preferably 1 to 4 carbon atoms, and most preferably 1 to 3 carbon atoms. The linear aliphatic hydrocarbon group is preferably a linear alkylene group, and specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The branched aliphatic hydrocarbon group which may be bonded to the alicyclic hydrocarbon group preferably has 2 to 10 carbon atoms, more preferably 3 to 6 carbon atoms, still more preferably 3 or 4 carbon atoms, and most preferably 3 carbon atoms. The branched aliphatic hydrocarbon group is preferably a branched alkylene group, and specific examples thereof include alkylalkylene groups, for example, alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH (CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH₃)CH₂CH₂—, and —CH₂CH(CH₃)CH₂—; and alkyltetramethylene groups such as —CH(CH₃)CH₂CH₂CH₂—, and —CH₂CH(CH₃)CH₂CH₂—. The alkyl group in the alkylalkylene group is preferably a linear alkyl group having 1 to 5 carbon atoms.

The cyclic hydrocarbon group as $R^{101}$ may contain a hetero atom such as a heterocyclic ring. Specific examples thereof include lactone-containing cyclic groups each represented by General Formulae (a2-r-1) to (a2-r-7), —SO₂—containing cyclic groups each represented by General Formulae (a5-r-1) to (a5-r-4), and other heterocyclic groups each represented by Chemical Formulae (r-hr-1) to (r-hr-16). In the formulae, *represents a bonding site that is bonded to $Y^{101}$ in General Formula (b-1).

[Chemical Formula 61]

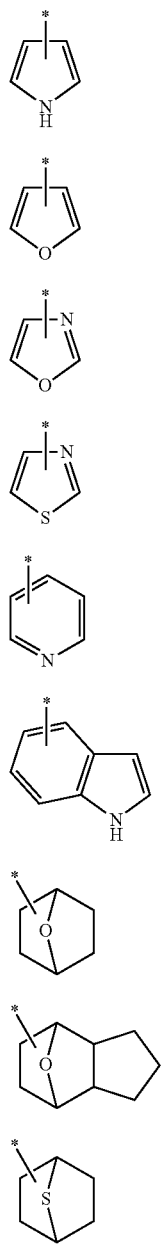

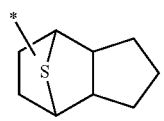

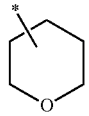

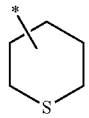

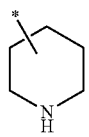

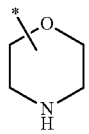

Examples of the substituent of the cyclic group as $R^{101}$ include an alkyl group, an alkoxy group, a halogen atom, a halogenated alkyl group, a hydroxyl group, a carbonyl group, and a nitro group.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom as the substituent include a fluorine atom, a chlorine atom, a bromine atom, and an iodine atom, and a fluorine atom is preferable.

Examples of the above-described halogenated alkyl group as the substituent include a group in which part or all of hydrogen atoms in an alkyl group having 1 to 5 carbon atoms such as a methyl group, an ethyl group, a propyl group, an n-butyl group, or a tert-butyl group have been substituted with the above-described halogen atom.

The carbonyl group as the substituent is a group that substitutes a methylene group (—CH₂—) constituting the cyclic hydrocarbon group.

The cyclic hydrocarbon group as $R^{101}$ may be a condensed ring-type group containing a condensed ring in which an aliphatic hydrocarbon ring and an aromatic ring are condensed. Examples of the condensed ring include a condensed ring in which one or more aromatic rings are condensed with a polycycloalkane having a bridged ring-based polycyclic skeleton. Specific examples of the bridged ring-based polycycloalkane include bicycloalkanes such as bicyclo[2.2.1]heptane (norbornane) and bicyclo[2.2.2]octane. The condensed ring type is preferably a group containing a condensed ring in which two or three aromatic rings are condensed with a bicycloalkane and more preferably a group containing a condensed ring in which two or three aromatic rings are condensed with bicyclo[2.2.2]octane. Specific examples of the condensed ring-type group as $R^{101}$ include those represented by General Formulae (r-br-1) to (r-br-2). In the formulae, * represents a bonding site that is bonded to $Y^{101}$ in General Formula (b-1).

[Chemical Formula 62]

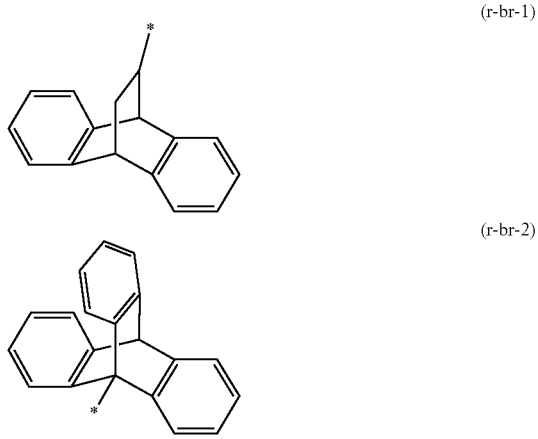

(r-br-1)

(r-br-2)

Examples of the substituent which the condensed ring-type group as $R^{101}$ may have include an alkyl group, an alkoxy group, a halogen atom, a halogenated alkyl group, a hydroxyl group, a carbonyl group, a nitro group, an aromatic hydrocarbon group, and an alicyclic hydrocarbon group.

Examples of the alkyl group, the alkoxy group, the halogen atom, and the halogenated alkyl group, as the substituent of the condensed ring-type group, include the same groups as those described as the substituent of the cyclic group as $R^{101}$.

Examples of the aromatic hydrocarbon group as the substituent of the condensed ring-type group include a group in which one hydrogen atom has been removed from the above-described aromatic ring (an aryl group, for example, a phenyl group and a naphthyl group), a group in which one hydrogen atom in the aromatic ring has been substituted with an alkylene group (for example, arylalkyl groups such as a benzyl group, a phenethyl group, a 1-naphthylmethyl group, a 2-naphthylmethyl group, 1-naphthylethyl group, and a 2-naphthylethyl group), and heterocyclic groups each represented by General Formulae (r-hr-1) to (r-hr-6).

Examples of the alicyclic hydrocarbon group as the substituent of the condensed ring-type group include a group in which one hydrogen atom has been removed from monocycloalkanes such as cyclopentane and cyclohexane; a group in which one hydrogen atom has been removed from polycycloalkanes such as adamantane, norbornane, isobornane, tricyclodecane, and tetracyclododecane; lactone-containing cyclic groups each represented by General Formulae (a2-r-1) to (a2-r-7); —SO$_2$—-containing cyclic groups each represented by General Formulae (a5-r-1) to (a5-r-4); and heterocyclic groups each represented by General Formulae (r-hr-7) to (r-hr-16).

Chain-Like Alkyl Group which may have Substituent:

The chain-like alkyl group as $R^{101}$ may be linear or branched.

The linear alkyl group preferably has 1 to 20 carbon atoms, more preferably 1 to 15 carbon atoms, and most preferably 1 to 10 carbon atoms.

The branched alkyl group preferably has 3 to 20 carbon atoms, more preferably 3 to 15, and most preferably 3 to 10. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

Chain-Like Alkenyl Group which may have Substituent:

A chain-like alkenyl group as $R^{101}$ may be linear or branched, and the chain-like alkenyl group preferably has 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, and a 2-methylpropenyl group.

Among the above, the chain-like alkenyl group is preferably a linear alkenyl group, more preferably a vinyl group or a propenyl group, and particularly preferably a vinyl group.

Examples of the substituent in the chain-like alkyl group or alkenyl group as $R^{101}$, include an alkoxy group, a halogen atom, a halogenated alkyl group, a hydroxyl group, a carbonyl group, a nitro group, an amino group, and a cyclic group as $R^{101}$.

Among the above, $R^{101}$ is preferably a cyclic group which may have a substituent and more preferably a cyclic hydrocarbon group which may have a substituent. More specific examples of the preferred cyclic hydrocarbon group include a phenyl group, a naphthyl group, a group in which one or more hydrogen atoms have been removed from a polycycloalkane, lactone-containing cyclic groups each represented by any of General Formulae (a2-r-1) to (a2-r-7), and —SO$_2$—-containing cyclic groups each represented by any of General Formulae (a5-r-1) to (a5-r-4).

In General Formula (b-1), $Y^{101}$ represents a single bond or a divalent linking group containing an oxygen atom.

In a case where $Y^{101}$ represents a divalent linking group containing an oxygen atom, $Y^{101}$ may contain an atom other than an oxygen atom. Examples of atoms other than an oxygen atom include a carbon atom, a hydrogen atom, a sulfur atom, and a nitrogen atom.

Examples of divalent linking groups containing an oxygen atom include non-hydrocarbon-based oxygen atom-containing linking groups such as an oxygen atom (an ether bond; —O—), an ester bond (—C(=O)—O—), an oxycarbonyl group (—O—C(=O)—), an amide bond (—C(=O)—NH—), a carbonyl group (—C(=O)—), or a carbonate bond (—O—C(=O)—O—); and combinations of the above-described non-hydrocarbon-based oxygen atom-containing linking groups with an alkylene group. Furthermore, a sulfonyl group (—SO$_2$—) may be linked to the combination. Examples of divalent linking groups containing an oxygen atom include linking groups each represented by General Formulae (y-a1-1) to (y-a1-7) shown below.

[Chemical Formula 63]

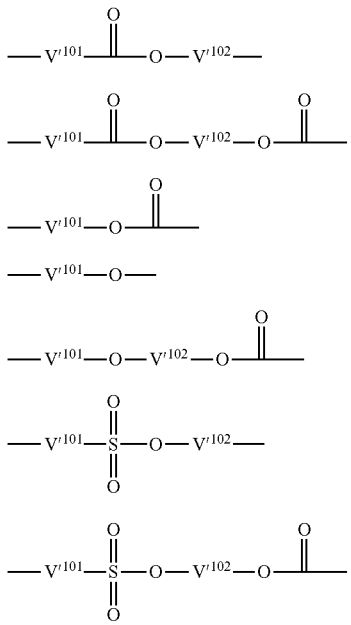

(y-a1-1)
(y-a1-2)
(y-a1-3)
(y-a1-4)
(y-a1-5)
(y-a1-6)
(y-a1-7)

[In the formulae, $V'^{101}$ represents a single bond or an alkylene group having 1 to 5 carbon atoms, and $V'^{102}$ represents a divalent saturated hydrocarbon group having 1 to 30 carbon atoms.]

The divalent saturated hydrocarbon group as $V'^{102}$ is preferably an alkylene group having 1 to 30 carbon atoms, more preferably an alkylene group having 1 to 10 carbon atoms, and still more preferably an alkylene group having 1 to 5 carbon atoms.

The alkylene group as $V'^{101}$ and $V'^{102}$ may be a linear alkylene group or a branched alkylene group, and a linear alkylene group is preferable.

Specific examples of the alkylene group as $V'^{101}$ and $V'^{102}$ include a methylene group [—$CH_2$—]; an alkylmethylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, or —$C(CH_2CH_3)_2$—; an ethylene group [—$CH_2CH_2$—]; an alkylethylene group such as —$CH(CH_3)CH_2$—, —$CH(CH_3)CH(CH_3)$—, —$C(CH_3)_2CH_2$—, or —$CH(CH_2CH_3)CH_2$—; a trimethylene group (n-propylene group) [—$CH_2CH_2CH_2$—]; an alkyltrimethylene group such as —$CH(CH_3)CH_2CH_2$— or —$CH_2CH(CH_3)CH_2$—; a tetramethylene group [—$CH_2CH_2CH_2CH_2$—]; an alkyltetramethylene group such as —$CH(CH_3)CH_2CH_2CH_2$—, or —$CH_2CH(CH_3)CH_2CH_2$—; and a pentamethylene group [—$CH_2CH_2CH_2CH_2CH_2$—].

Further, a part of a methylene group in the alkylene group as $V'^{101}$ and $V'^{102}$ may be substituted with a divalent aliphatic cyclic group having 5 to 10 carbon atoms. The aliphatic cyclic group is preferably a divalent group in which one hydrogen atom has been removed from the cyclic aliphatic hydrocarbon group (a monocyclic aliphatic hydrocarbon group or a polycyclic aliphatic hydrocarbon group) as $Ra^{r3}$ in General Formula (a1-r-1), and a cyclohexylene group, a 1,5-adamantylene group, or a 2,6-adamantylene group is more preferable.

$Y^{101}$ preferably represents a divalent linking group containing an ester bond or a divalent linking group containing an ether bond and more preferably linking groups each represented by General Formulae (y-a1-1) to (y-a1-5).

In General Formula (b-1), $V^{101}$ represents a single bond, an alkylene group, or a fluorinated alkylene group. The alkylene group and the fluorinated alkylene group as $V^{101}$ preferably have 1 to 4 carbon atoms. Examples of the fluorinated alkylene group as $V^{101}$ include a group in which part or all of hydrogen atoms in the alkylene group as $V^{101}$ have been substituted with a fluorine atom. Among these examples, as $V^{101}$, a single bond or a fluorinated alkylene group having 1 to 4 carbon atoms is preferable.

In General Formula (b-1), $R^{102}$ represents a fluorine atom or a fluorinated alkyl group having 1 to 5 carbon atoms. $R^{102}$ preferably represents a fluorine atom or a perfluoroalkyl group having 1 to 5 carbon atoms and more preferably a fluorine atom.

As a specific example of the anion moiety represented by General Formula (b-1), in a case where $Y^{101}$ represents a single bond, a fluorinated alkylsulfonate anion such as a trifluoromethanesulfonate anion or a perfluorobutanesulfonate anion can be mentioned; and in a case where $Y^{101}$ represents a divalent linking group containing an oxygen atom, anions represented by General Formulae (an-1) to (an-3) shown below can be mentioned.

[Chemical Formula 64]

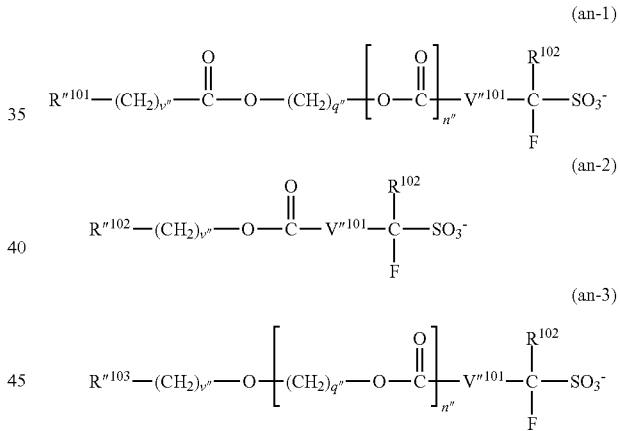

(an-1)
(an-2)
(an-3)

[In the formula, $R'''^{101}$ represents an aliphatic cyclic group which may have a substituent, monovalent heterocyclic groups each represented by Chemical Formulae (r-hr-1) to (r-hr-6), a condensed ring-type group represented by General Formula (r-br-1) or (r-br-2), and a chain-like alkyl group which may have a substituent. $R'''^{102}$ is an aliphatic cyclic group which may have a substituent, a condensed ring-type group represented by General Formula (r-br-1) or (r-br-2), lactone-containing cyclic groups each represented by General Formulae (a2-r-1), (a2-r-3) to (a2-r-7), or —$SO_2$—containing cyclic groups each represented by General Formulae (a5-r-1) to (a5-r-4). $R'''^{103}$ represents an aromatic cyclic group which may have a substituent, an aliphatic cyclic group which may have a substituent, or a chain-like alkenyl group which may have a substituent. $V'''^{101}$ represents a single bond, an alkylene group having 1 to 4 carbon atoms, or a fluorinated alkylene group having 1 to 4 carbon atoms. $R^{102}$ represents a fluorine atom or a fluorinated alkyl group having 1 to 5 carbon atoms. Each $v''$ independently represents an integer in a range of 0 to 3, each q″ independently represents an integer in a range of 0 to 20, and n″ represents 0 or 1.]

The aliphatic cyclic group as $R''^{101}$, $R''^{102}$, and $R''^{103}$ which may have a substituent is preferably the group exemplified as the cyclic aliphatic hydrocarbon group as $R^{101}$ in General Formula (b-1). Examples of the substituent include the same group as the substituent with which the cyclic aliphatic hydrocarbon group as $R^{101}$ in General Formula (b-1) may be substituted.

The aromatic cyclic group as $R''^{103}$ in General Formula (b-1), which may have a substituent, is preferably the group exemplified as the aromatic hydrocarbon group for the cyclic hydrocarbon group as $R^{101}$ in General Formula (b-1). Examples of the substituent include the same groups as the substituent with which the aromatic hydrocarbon group as $R^{101}$ in General Formula (b-1) may be substituted.

The chain-like alkyl group as $R''^{101}$, which may have a substituent, is preferably the group exemplified as the chain-like alkyl group as $R^{101}$ in General Formula (b-1).

The chain-like alkenyl group as $R''^{103}$, which may have a substituent, is preferably the group exemplified as the chain-like alkenyl group as $R^{101}$ in General Formula (b-1).

Anion in Component (b-2)

In Formula (b-2), $R^{104}$ and $R^{105}$ each independently represent a cyclic group which may have a substituent, a chain-like alkyl group which may have a substituent, or a chain-like alkenyl group which may have a substituent, and are each the same as $R^{101}$ in Formula (b-1). However, $R^{104}$ and $R^{105}$ may be bonded to each other to form a ring.

$R^{104}$ and $R^{105}$ are preferably a chain-like alkyl group which may have a substituent and more preferably a linear or branched alkyl group or a linear or branched fluorinated alkyl group.

The chain-like alkyl group preferably has 1 to 10 carbon atoms, more preferably 1 to 7 carbon atoms, and still more preferably 1 to 3 carbon atoms. It is preferable that the number of carbon atoms in the chain-like alkyl group as $R^{104}$ and $R^{105}$ be small since the solubility in a solvent for a resist is also excellent in this range of the number of carbon atoms. Further, in the chain-like alkyl group as $R^{104}$ and $R^{105}$, it is preferable that the number of hydrogen atoms substituted with a fluorine atom be large since the acid strength increases and the transparency to high energy radiation of 250 nm or less or electron beams is improved. The proportion of fluorine atoms in the chain-like alkyl group, that is, the fluorination ratio is preferably in a range of 70% to 100% and more preferably in a range of 90% to 100%, and it is most preferable that the chain-like alkyl group be a perfluoroalkyl group in which all hydrogen atoms be substituted with a fluorine atom.

in General Formula (b-2), $V^{102}$ and $V^{103}$ each independently represent a single bond, an alkylene group, or a fluorinated alkylene group, and has the same definition as that for $V^{101}$ in General Formula (b-1).

in General Formula (b-2), $L^{101}$ and $L^{102}$ each independently represent a single bond or an oxygen atom.

Anion in Component (b-3)

In Formula (b-3), $R^{106}$ to $R^{108}$ each independently represents a cyclic group which may have a substituent, chain-like alkyl group which may have a substituent, or a chain-like alkenyl group which may have a substituent, and examples thereof include the same group as $R^{101}$ in Formula (b-1).

In General Formula (b-3), $L^{103}$ to $L^{105}$ each independently represents a single bond, —CO—, or —SO$_2$—.

Among the above, the anion moiety of the component (B) is preferably an anion of the component (b-1). Among these, an anion represented by any one of General Formulae (an-1) to (an-3) is more preferable, an anion represented by any one of General Formula (an-1) or (an-2) is still more preferable, and an anion represented by General Formula (an-2) is particularly preferable.

{Cation Moiety}

In General Formulae (b-1), (b-2), and (b-3), $M'^{m+}$ represents an m-valent onium cation. Among them, a sulfonium cation and an iodonium cation are preferable.

m represents an integer of 1 or greater.

Preferred examples of the cation moiety $((M^{m+})_{1/m})$ include organic cations each represented by General Formulae (ca-1) to (ca-5). Examples thereof include organic cations each represented by General Formulae (ca-1) to (ca-5).

Specific examples of the suitable cations each represented by General Formula (ca-1) include cations each represented by General Formulae (ca-1-1) and (ca-1-71) shown below.

Specific examples of suitable cations represented by General Formula (ca-2) include a diphenyliodonium cation and a bis(4-tert-butylphenyl)iodonium cation.

Specific examples of the suitable cations each represented by General Formula (ca-3) include cations each represented by General Formulae (ca-3-1) and (ca-3-6) shown below.

Specific examples of the suitable cations each represented by General Formula (ca-4) include cations each represented by General Formulae (ca-4-1) and (ca-4-2) shown below.

Specific examples of the suitable cations each represented by General Formula (ca-5) include cations each represented by General Formulae (ca-5-1) to (ca-5-3) shown below.

Among the above, the cation moiety $[(M'^{m+})_{1/m}]$ is preferably a cation represented by General Formula (ca-1), and more preferably cations each represented by General Formulae (ca-1-1) to (ca-1-71).

In the resist composition according to the present embodiment, the component (B) may be used alone or in a combination of two or more kinds thereof.

In a case where the resist composition contains the component (B), the content of the component (B) in the resist composition is preferably less than 50 parts by mass, more preferably in a range of 1 to 40 parts by mass, and still more preferably in a range of 5 to 25 parts by mass with respect to 100 parts by mass of the component (A).

In a case where the content of the component (B) is set to be in the preferred range described above, pattern formation can be satisfactorily carried out. Further, in a case where each component of the resist composition is dissolved in an organic solvent, the above range is preferable since a uniform solution is easily obtained and the storage stability of the resist composition is improved.

<<Base Component (D)>>

The resist composition of the present aspect may contain an acid diffusion-controlling agent component (hereinafter, referred to as a "component (D)") other than the component (D0) as long as the effects of the present invention are not impaired.

The component (D) acts as a quencher (an acid diffusion-controlling agent) which traps the acid generated in the resist composition upon exposure.

Examples of the component (D) include a photodecomposable base (D1) having an acid diffusion controllability (hereinafter, referred to as a "component (D1)") which is lost by the decomposition upon exposure and a nitrogen-containing organic compound (D2) (hereinafter, referred to as a "component (D2)") which does not correspond to the component (D1). Among these, the photodecomposable base (the component (D1)) is preferable since it is easy to enhance the characteristics of high sensitivity, roughness reduction, and suppression of the occurrence of coating defects.

In Regard to Component (D1)

In a case where a resist composition containing the component (D1) is obtained, the contrast between the exposed portion and the unexposed portion of the resist film can be further improved at the time of the formation of a resist pattern.

The component (D1) is not particularly limited as long as it is decomposed upon exposure and loses the acid diffusion controllability. The component (D1) is preferably one or more compounds selected from the group consisting of a compound represented by General Formula (d1-1) (hereinafter, referred to as a "component (d1-1)"), a compound represented by General Formula (d1-2) (hereinafter, referred to as a "component (d1-2)"), and a compound represented by General Formula (d1-3) (hereinafter, referred to as a "component (d1-3)").

At the exposed portion of the resist film, the components (d1-1) to (d1-3) are decomposed and then lose the acid diffusion controllability (basicity), and thus the components (d1-1) to (d1-3) cannot act as a quencher, whereas the components (d1-1) to (d1-3) act as a quencher at the unexposed portion of the resist film.

[Chemical Formula 65]

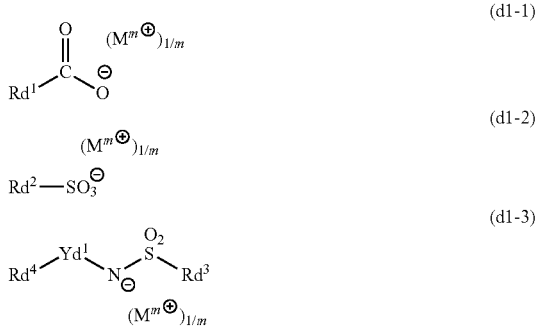

[In the formulae, $Rd^1$ to $Rd^4$ represent cyclic groups which may have a substituent, chain-like alkyl groups which may have a substituent, or chain-like alkenyl groups which may have a substituent. Here, the carbon atom adjacent to the S atom as $Rd^2$ in General Formula (d1-2) has no fluorine atom bonded thereto. $Yd^1$ represents a single bond or a divalent linking group. m represents an integer of 1 or greater, and each $M^{m+}$ independently represents an m-valent organic cation.]

{Component (d1-1)}

Anion Moiety

In General Formula (d1-1), $Rd^1$ represents a cyclic group which may have a substituent, a chain-like alkyl group which may have a substituent, or a chain-like alkenyl group which may have a substituent, and examples thereof include the same group as $R'^{201}$.

Among these, $Rd^1$ is preferably an aromatic hydrocarbon group which may have a substituent, an aliphatic cyclic group which may have a substituent, or a chain-like alkyl group which may have a substituent. Examples of the substituent which these groups may have include a hydroxyl group, an oxo group, an alkyl group, an aryl group, a fluorine atom, a fluorinated alkyl group, lactone-containing cyclic groups each represented by any of General Formulae (a2-r-1) to (a2-r-7) described above, an ether bond, an ester bond, and a combination thereof. In a case where an ether bond or an ester bond is included as the substituent, the substituent may be bonded via an alkylene group, and linking groups each represented by any of Formulae (y-a1-1) to (y-a1-5) are preferable as the substituent.

As the aromatic hydrocarbon group, a phenyl group, a naphthyl group, and a polycyclic structure (a polycyclic structure including a bicyclooctane skeleton and a ring structure other than the bicyclooctane skeleton) including a bicyclooctane skeleton can be suitably mentioned.

The aliphatic cyclic group is preferably a group in which one or more hydrogen atoms have been removed from a polycycloalkane such as adamantane, norbornane, isobornane, tricyclodecane, or tetracyclododecane.

The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl group, or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, or a 4-methylpentyl group.

In a case where the chain-like alkyl group is a fluorinated alkyl group having a fluorine atom or a fluorinated alkyl group as a substituent, the fluorinated alkyl group preferably has 1 to 11 carbon atoms, more preferably 1 to 8 carbon atoms, and still more preferably 1 to 4 carbon atoms. The fluorinated alkyl group may contain an atom other than a fluorine atom. Examples of the atom other than a fluorine atom include an oxygen atom, a sulfur atom, and a nitrogen atom.

As $Rd^1$, a fluorinated alkyl group in which part or all of hydrogen atoms constituting a linear alkyl group have been substituted with a fluorine atom is preferable, and a fluorinated alkyl group in which all of the hydrogen atoms constituting a linear alkyl group have been substituted with a fluorine atom (a linear perfluoroalkyl group) is particularly preferable.

Specific examples of the preferred anion moiety for the component (d1-1) are shown below.

[Chemical Formula 66]

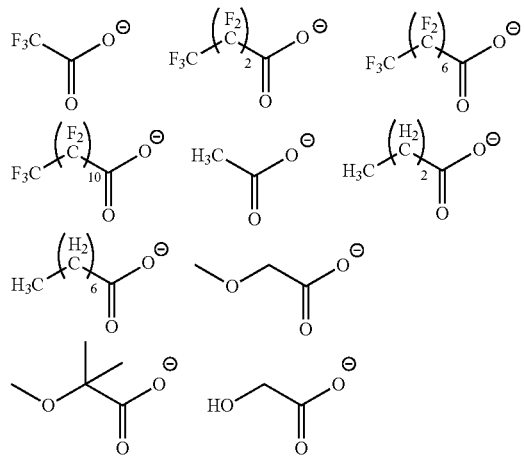

-continued

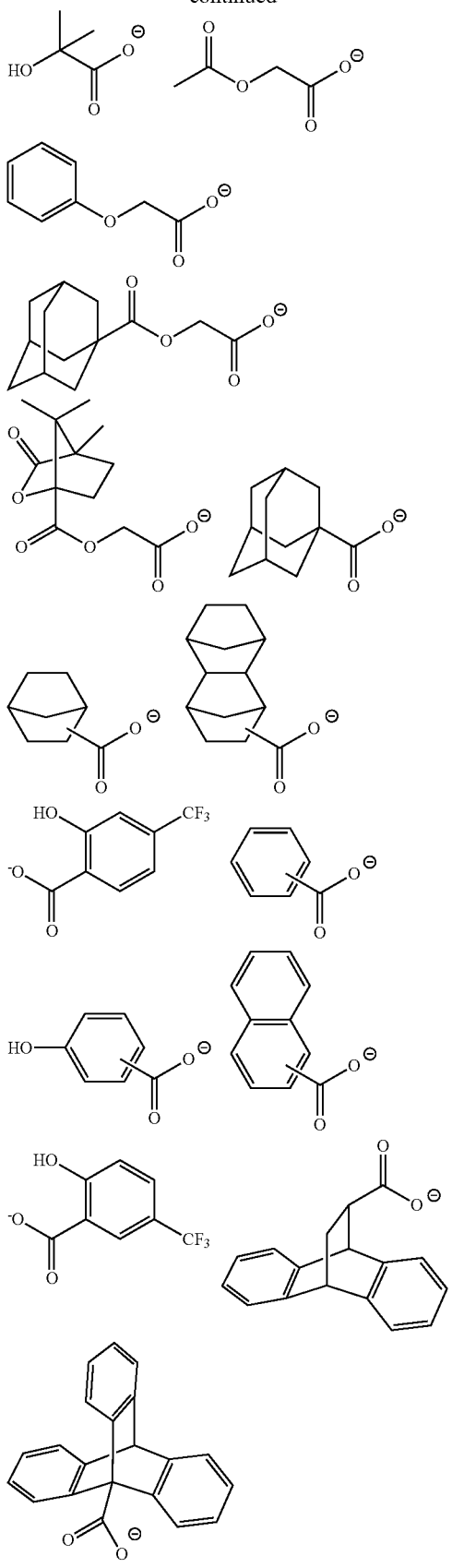

Cation Moiety

In General Formula (d1-1), $M^{m+}$ represents an m-valent organic cation.

Suitable examples of the organic cation as $M^{m+}$ include the same organic cation as those each represented by General Formulae (ca-1) to (ca-5), the cation represented by General Formula (ca-1) is preferable, and cations each represented by General Formulae (ca-1-1) to (ca-1-71) are more preferable.

The component (d1-1) may be used alone or in a combination of two or more kinds thereof.

{Component (d1-2)}

Anion Moiety

In General Formula (d1-2), $Rd^2$ represents a cyclic group which may have a substituent, a chain-like alkyl group which may have a substituent, or a chain-like alkenyl group which may have a substituent, and examples thereof include the same group as $R'^{201}$.

Here, the carbon atom adjacent to the S atom in $Rd^2$ has no fluorine atom bonded thereto (the carbon atom adjacent to the S atom in $Rd^2$ is not substituted with a fluorine atom). As a result, the anion of the component (d1-2) becomes an appropriately weak acid anion, thereby improving the quenching ability of the component (D).

$Rd^2$ is preferably a chain-like alkyl group which may have a substituent or an aliphatic cyclic group which may have a substituent. The chain-like alkyl group preferably has 1 to 10 carbon atoms and more preferably 3 to 10 carbon atoms. The aliphatic cyclic group is more preferably a group (which may have a substituent) in which one or more hydrogen atoms have been removed from adamantane, norbornane, isobornane, tricyclodecane, tetracyclododecane, or the like; and a group in which one or more hydrogen atoms have been removed from camphor or the like.

The hydrocarbon group as $Rd^2$ may have a substituent. Examples of the substituent include the same substituent as that which the hydrocarbon group (an aromatic hydrocarbon group, an aliphatic cyclic group, or a chain-like alkyl group) as $Rd^1$ in General Formula (d1-1) may have.

Specific examples of the preferred anion moiety for the component (d1-2) are shown below.

[Chemical Formula 67]

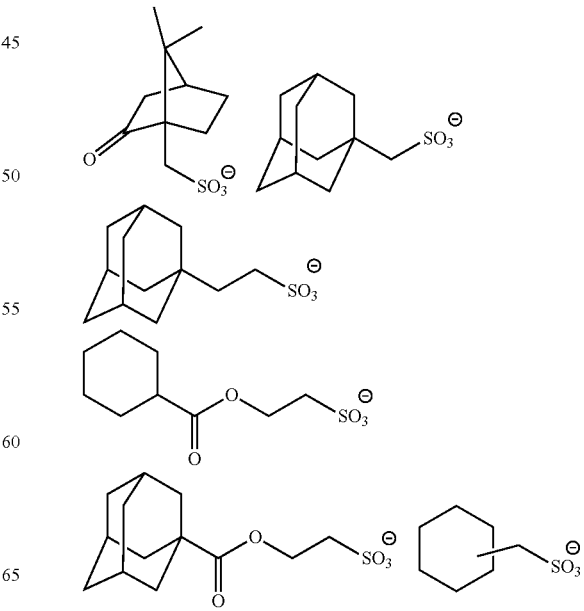

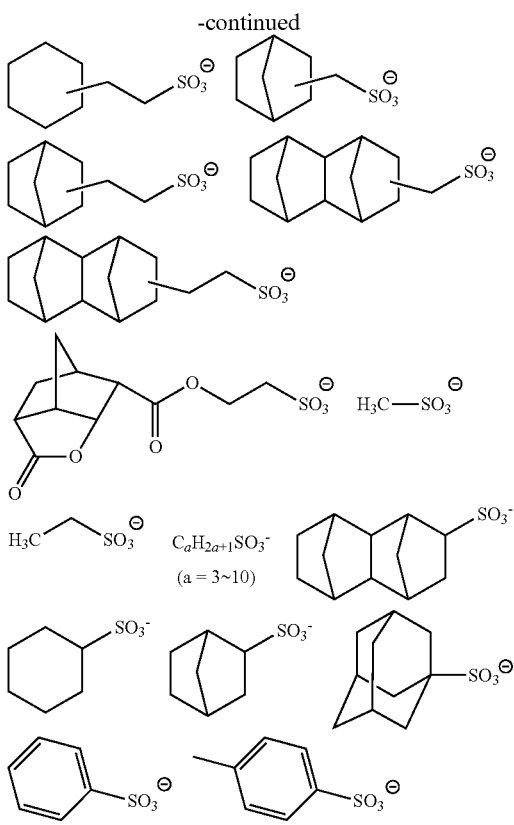

Cation Moiety

In General Formula (d1-2), $M^{m+}$ represents an m-valent organic cation and is the same as $M^{m+}$ in General Formula (d1-1).

The component (d1-2) may be used alone or in a combination of two or more kinds thereof.

{Component (d1-3)}

Anion Moiety

In General Formula (d1-3), $Rd^3$ represents a cyclic group which may have a substituent, a chain-like alkyl group which may have a substituent, or a chain-like alkenyl group which may have a substituent, examples thereof include the same groups as $R'^{201}$, and a cyclic group containing a fluorine atom, a chain-like alkyl group, or a chain-like alkenyl group is preferable. Among them, a fluorinated alkyl group is preferable, and the same fluorinated alkyl group as that described above as $Rd^1$ is more preferable.

In General Formula (d1-3), $Rd^4$ represents a cyclic group which may have a substituent, a chain-like alkyl group which may have a substituent, or a chain-like alkenyl group which may have a substituent, and examples thereof include the same group as $R'^{201}$.

Among them, an alkyl group which may have a substituent, an alkoxy group which may have a substituent, an alkenyl group which may have a substituent, or a cyclic group which may have a substituent is preferable.

The alkyl group as $Rd^4$ is preferably a linear or branched alkyl group having 1 to 5 carbon atoms, and specific examples thereof include a methyl group, an ethyl group, a propyl group, an isopropyl group, an n-butyl group, an isobutyl group, a tert-butyl group, a pentyl group, an iso-pentyl group, and a neopentyl group. A part of hydrogen atoms in the alkyl group as $Rd^4$ may be substituted with a hydroxyl group, a cyano group, or the like.

The alkoxy group as $Rd^4$ is preferably an alkoxy group having 1 to 5 carbon atoms, and specific examples of the alkoxy group having 1 to 5 carbon atoms include a methoxy group, an ethoxy group, an n-propoxy group, an iso-propoxy group, an n-butoxy group, and a tert-butoxy group. Among these, a methoxy group and an ethoxy group are preferable.

Examples of the alkenyl group as $Rd^4$ include the same group as $R'^{201}$, and a vinyl group, a propenyl group (an allyl group), a 1-methylpropenyl group, or a 2-methylpropenyl group is preferable. These groups may have an alkyl group having 1 to 5 carbon atoms or a halogenated alkyl group having 1 to 5 carbon atoms as a substituent.

Examples of the cyclic group as $Rd^4$ include the same cyclic group as $R'^{201}$ and an alicyclic group in which one or more hydrogen atoms have been removed from a cycloalkane such as cyclopentane, cyclohexane, adamantane, norbornane, isobornane, tricyclodecane, or tetracyclododecane, or an aromatic group such as a phenyl group or a naphthyl group is preferable. In a case where $Rd^4$ represents an alicyclic group, the resist composition can be satisfactorily dissolved in an organic solvent, thereby improving lithography characteristics. In a case where $Rd^4$ is an aromatic group, the resist composition is excellent in light absorption efficiency and thus has good sensitivity and lithography characteristics in the lithography using EUV or the like as a light source for exposure.

In General Formula (d1-3), $Yd^1$ represents a single bond or a divalent linking group.

The divalent linking group as $Yd^1$ is not particularly limited, and examples thereof include a divalent hydrocarbon group (an aliphatic hydrocarbon group or an aromatic hydrocarbon group) which may have a substituent and a divalent linking group containing a hetero atom. The divalent linking groups are the same as those described above as the divalent hydrocarbon group which may have a substituent and the divalent linking group containing a hetero atom described above as the divalent linking group as $Ya^{21}$ in General Formula (a2-1).

As $Yd^1$, a carbonyl group, an ester bond, an amide bond, an alkylene group, or a combination of these is preferable. As the alkylene group, a linear or branched alkylene group is more preferable, and a methylene group or an ethylene group is still more preferable.

Specific examples of the preferred anion moiety for the component (d1-3) are shown below.

[Chemical Formula 68]

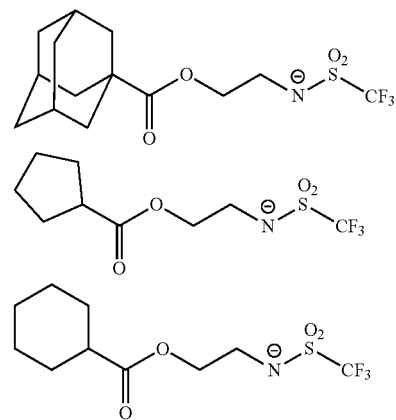

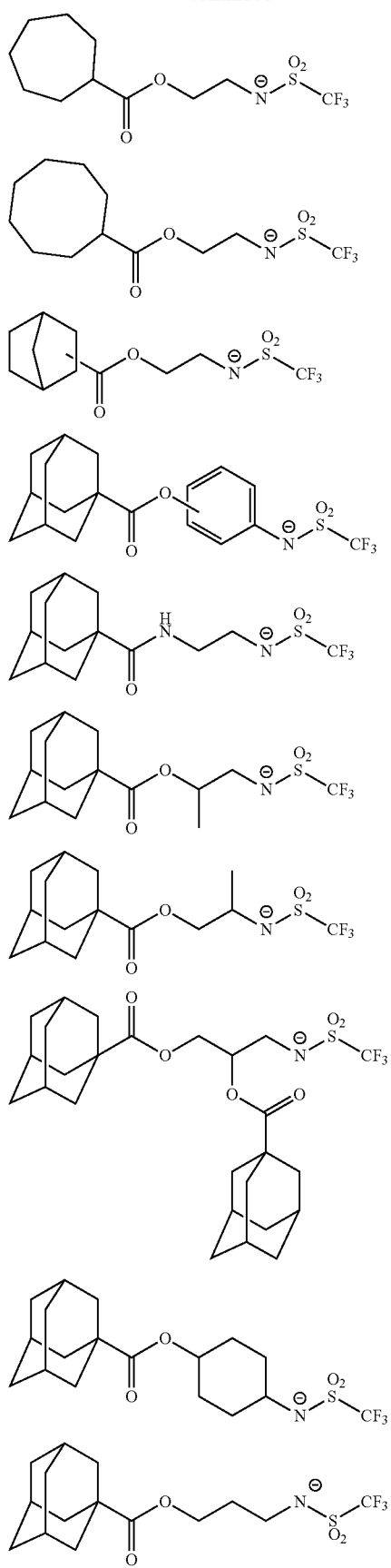
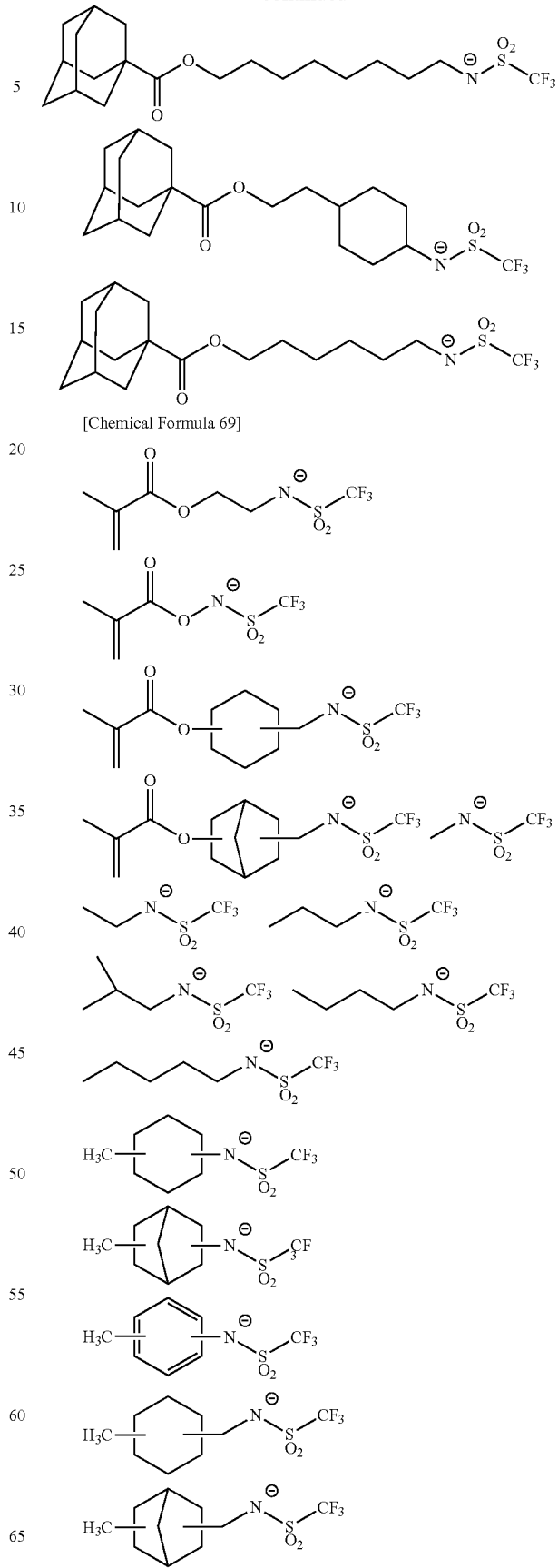
[Chemical Formula 69]

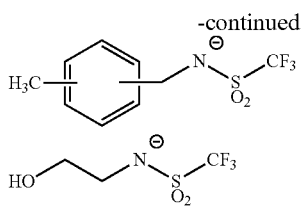

Cation Moiety

In General Formula (d1-3), $M^{m+}$ represents an m-valent organic cation and is the same as $M^{m+}$ in General Formula (d1-1).

The component (d1-3) may be used alone or in a combination of two or more kinds thereof.

As the component (D1), only one of the above-described components (d1-1) to (d1-3) or a combination of two or more kinds thereof may be used.

In a case where the resist composition contains the component (D1), the content of the component (D1) in the resist composition is preferably less than 0.5 to 20 parts by mass, more preferably in a range of 1 to 15 parts by mass, and still more preferably in a range of 5 to 10 parts by mass with respect to 100 parts by mass of the component (A).

In a case where the content of the component (D1) is equal to or greater than the preferred lower limit value, excellent lithography characteristics and an excellent resist pattern shape are easily obtained. On the other hand, in a case where the content of the component (D1) is equal to or lower than the upper limit value, the sensitivity can be maintained satisfactorily and the throughput is also excellent.

Method of Producing Component (D1):

The methods of producing the components (d1-1) and (d1-2) are not particularly limited, and the components (d1-1) and (d1-2) can be produced by conventionally known methods.

Further, the method of producing the component (d1-3) is not particularly limited, and the component (d1-3) can be produced in the same manner as disclosed in United States Patent Application, Publication No. 2012-0149916.

In Regard to Component (D2)

The component (D) may contain a nitrogen-containing organic compound component (hereinafter, referred to as a "component (D2)") which does not correspond to the above-described component (D1).

The component (D2) is not particularly limited as long as it acts as an acid diffusion-controlling agent and does not correspond to the component (D1), and any known compound may be used. Among the above, aliphatic amines are preferable, and among the aliphatic amines, a secondary aliphatic amine or a tertiary aliphatic amine is more preferable.

An aliphatic amine is an amine having one or more aliphatic groups, and the aliphatic groups preferably have 1 to 12 carbon atoms.

Examples of these aliphatic amines include an amine in which at least one hydrogen atom of ammonia ($NH_3$) has been substituted with an alkyl group or hydroxyalkyl group having 12 or fewer carbon atoms (alkyl amines or alkyl alcohol amines) and a cyclic amine.

Specific examples of alkyl amines and alkyl alcohol amines include monoalkyl amines such as n-hexyl amine, n-heptyl amine, n-octyl amine, n-nonyl amine, and n-decyl amine; dialkyl amines such as diethyl amine, di-n-propyl amine, di-n-heptyl amine, di-n-octyl amine, and dicyclohexyl amine; trialkyl amines such as trimethyl amine, triethyl amine, tri-n-propyl amine, tri-n-butyl amine, tri-n-hexyl amine, tri-n-pentyl amine, tri-n-heptyl amine, tri-n-octyl amine, tri-n-nonyl amine, tri-n-decyl amine, and tri-n-dodecyl amine; and alkyl alcohol amines such as diethanol amine, triethanol amine, diisopropanol amine, triisopropanol amine, di-n-octanol amine, and tri-n-octanol amine Among these, trialkyl amines of 5 to 10 carbon atoms are preferable, and tri-n-pentyl amine and tri-n-octyl amine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanol amine triacetate, and triethanol amine triacetate is preferable.

In addition, as the component (D2), an aromatic amine may be used.

Examples of aromatic amines include 4-dimethylaminopyridine, pyrrole, indole, pyrazole, imidazole, and derivatives thereof, tribenzylamine, 2,6-diisopropylaniline, and N-tert-butoxycarbonylpyrrolidine.

The component (D2) may be used alone or in a combination of two or more kinds thereof.

In a case where the resist composition contains the component (D2), the content of the component (D2) in the resist composition is typically in a range of 0.01 to 5 parts by mass with respect to 100 parts by mass of the component (A). By setting the content within the above range, the resist pattern shape, the post-exposure temporal stability, and the like are improved.

<<At Least One Compound (E) Selected from the Group Consisting of Organic Carboxylic Acid, Phosphorus Oxo Acid, and Derivatives Thereof>>

For the intended purpose of preventing any deterioration in sensitivity, and improving the resist pattern shape and the post-exposure temporal stability, the resist composition according to the present embodiment may contain, as an optionally component, at least one compound (E) (hereinafter referred to as a component (E)) selected from the group consisting of an organic carboxylic acid, and a phosphorus oxo acid and a derivative thereof.

Examples of suitable organic carboxylic acids include acetic acid, malonic acid, citric acid, malic acid, succinic acid, benzoic acid, and salicylic acid.

Examples of phosphorus oxo acid include phosphoric acid, phosphonic acid, and phosphinic acid. Among these, phosphonic acid is particularly preferable.

Examples of phosphorus oxo acid derivatives include esters in which a hydrogen atom in the above-described oxo acids is substituted with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate, and dibenzyl phosphonate.

Examples of phosphinic acid derivatives include phosphinic acid esters and phenylphosphinic acid.

In the resist composition according to the present embodiment, the component (E) may be used alone or in a combination of two or more kinds thereof.

In a case where the resist composition contains the component (E), the content of the component (E) is typically in a range of 0.01 to 5 parts by mass with respect to 100 parts by mass of the component (A).

<<Fluorine Additive Component (F)>>

The resist composition according to the present embodiment may further include a fluorine additive component (hereinafter, referred to as a "component (F)") in order to impart water repellency to the resist film or to improve lithography characteristics.

As the component (F), a fluorine-containing polymer compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be mentioned.

Specific examples of the component (F) include polymers having a constitutional unit (f1) represented by General Formula (f1-1) shown below. This polymer is preferably a polymer (homopolymer) consisting of a constitutional unit (f1) represented by General Formula (f1-1) shown below; a copolymer of the constitutional unit (f1) and the constitutional unit (a1); and a copolymer of the constitutional unit (f1), a constitutional unit derived from acrylic acid or methacrylic acid, and the above-described constitutional unit (a1). As the constitutional unit (a1) to be copolymerized with the constitutional unit (f1), a constitutional unit derived from 1-ethyl-1-cyclooctyl (meth)acrylate and a constitutional unit derived from 1-methyl-1-adamantyl (meth)acrylate are preferable.

[Chemical Formula 70]

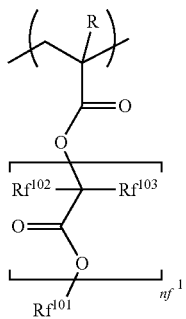

(f1-1)

[In the formula, R has the same definition as described above. $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other. $nf^1$ represents an integer in a range of 0 to 5 and $Rf^{101}$ represents an organic group containing a fluorine atom.]

In General Formula (f1-1), R bonded to the carbon atom at the α-position has the same definition as described above. R is preferably a hydrogen atom or a methyl group.

In General Formula (f1-1), the halogen atom of $Rf^{102}$ and $Rf^{103}$ is preferably a fluorine atom. Examples of the alkyl group having 1 to 5 carbon atoms as $Rf^{102}$ and $Rf^{103}$ include those described above as the alkyl group having 1 to 5 carbon atoms as R, and a methyl group or an ethyl group is preferable. Specific examples of the halogenated alkyl group having 1 to 5 carbon atoms as $Rf^{102}$ and $Rf^{103}$ include groups in which part or all of hydrogen atoms of the above-described alkyl groups of 1 to 5 carbon atoms have been substituted with a halogen atom. The halogen atom is preferably a fluorine atom. Among these examples, as $Rf^{102}$ and $Rf^{103}$ a hydrogen atom, a fluorine atom, or an alkyl group having 1 to 5 carbon atoms is preferable, and a hydrogen atom, a fluorine atom, a methyl group, or an ethyl group is more preferable.

In General Formula (f1-1), $nf^1$ represents an integer in a range of 0 to 5, preferably an integer in a range of 0 to 3, and more preferably an integer of 1 or 2.

In General Formula (f1-1), $Rf^{101}$ represents an organic group containing a fluorine atom and is preferably a hydrocarbon group containing a fluorine atom.

The hydrocarbon group containing a fluorine atom may be linear, branched, or cyclic, and preferably has 1 to 20 carbon atoms, more preferably 1 to 15 carbon atoms, and particularly preferably 1 to 10 carbon atoms.

In addition, in the hydrocarbon group containing a fluorine atom, 25% or more of the hydrogen atoms in the hydrocarbon group are preferably fluorinated, more preferably 50% or more are fluorinated, and particularly preferably 60% or more are fluorinated since the hydrophobicity of the resist film at the time of dipping exposure increases.

Among them, $Rf^{101}$ is preferably a fluorinated hydrocarbon group having 1 to 6 carbon atoms, more preferably a trifluoromethyl group, and particularly preferably —$CH_2$—$CF_3$, —$CH_2$—$CF_2$—$CF_3$, or —$CH(CF_3)_2$, —$CH_2$—$CH_2$—$CF_3$, or —$CH_2$—$CH_2$—$CF_2$—$CF_2$—$CF_2$—$CF_3$.

The weight-average molecular weight (Mw) (based on the polystyrene-equivalent value determined by gel permeation chromatography) of the component (F) is preferably in a range of 1,000 to 50,000, more preferably in a range of 5,000 to 40,000, and most preferably in a range of 10,000 to 30,000. In a case where the weight-average molecular weight is equal to or lower than the upper limit value of this range, the resist composition exhibits sufficiently satisfactory solubility in a solvent for a resist to be used as a resist. On the other hand, in a case where the weight-average molecular weight is equal to or greater than the lower limit value of this range, the water repellency of the resist film is excellent.

Further, the dispersity (Mw/Mn) of the component (F) is preferably in a range of 1.0 to 5.0, more preferably in a range of 1.0 to 3.0, and most preferably in a range of 1.0 to 2.5.

In the resist composition according to the present embodiment, the component (F) may be used alone or in a combination of two or more kinds thereof.

In a case where the resist composition contains the component (F), the content of the component (F) is typically at a proportion of 0.5 to 10 parts by mass, with respect to 100 parts by mass of the component (A).

<<Organic Solvent Component (S)>>

The resist composition according to the present embodiment may be produced by dissolving the resist materials in an organic solvent component (hereinafter, referred to as a "component (S)").

The component (S) may be any organic solvent which can dissolve the respective components to be used to obtain a uniform solution, and optional organic solvent can be suitably selected from those which are conventionally known as solvents for a chemical amplification-type resist composition and then used.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkyl ether (such as monomethyl ether, monoethyl ether, monopropyl ether or monobutyl ether) or monophenyl ether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzyl ether, cresylmethyl ether, diphenyl ether, dibenzyl ether, phenetole, butylphenyl ether, ethyl benzene, diethyl benzene, pentyl benzene, isopropyl benzene, toluene, xylene, cymene and mesitylene; and dimethylsulfoxide (DMSO).

In the resist composition according to the present embodiment, the component (S) may be used alone or as a mixed solvent of two or more kinds thereof. Among these, PGMEA, PGME, γ-butyrolactone, EL, and cyclohexanone are preferable.

Further, a mixed solvent obtained by mixing PGMEA with a polar solvent is also preferable as the component (S). The blending ratio (mass ratio) of the mixed solvent can be suitably determined, taking into consideration the compatibility of the PGMEA with the polar solvent, but is preferably in a range of 1:9 to 9:1 and more preferably in a range of 2:8 to 8:2.

More specifically, in a case where EL or cyclohexanone is blended as the polar solvent, the PGMEA:EL or cyclohexanone mass ratio is preferably in a range of 1:9 to 9:1 and more preferably in a range of 2:8 to 8:2. Alternatively, in a case where PGME is blended as the polar solvent, the PGMEA:PGME mass ratio is preferably in a range of 1:9 to 9:1, more preferably in a range of 2:8 to 8:2, and still more preferably in a range of 3:7 to 7:3. Furthermore, a mixed solvent of PGMEA, PGME, and cyclohexanone is also preferable.

Further, the component (S) is also preferably a mixed solvent of at least one selected from PGMEA and EL and γ-butyrolactone. In this case, as the mixing ratio, the mass ratio of the former to the latter is preferably in a range of 70:30 to 95:5.

The amount of the component (S) to be used is not particularly limited and is suitably set, depending on a thickness of a film to be coated, to a concentration at which the component (S) can be applied onto a substrate or the like.

Generally, the component (S) is used such that the solid content concentration of the resist composition is in a range of 0.1% to 20% by mass and preferably in a range of 0.2% to 15% by mass.

As desired, other miscible additives can also be added to the resist composition according to the present embodiment. For example, for improving the performance of the resist film, an additive resin, a dissolution inhibitor, a plasticizer, a stabilizer, a colorant, a halation prevention agent, and a dye can be suitably contained therein.

After dissolving the resist material in the component (S), the resist composition according to the present embodiment may be subjected to removal of impurities and the like by using a porous polyimide film, a porous polyamideimide film, or the like. For example, the resist composition may be filtered using a filter made of a porous polyimide film, a filter made of a porous polyamideimide film, or a filter made of a porous polyimide film and a porous polyamideimide film. Examples of the porous polyimide film and the porous polyamideimide film include those described in Japanese Unexamined Patent Application, First Publication No. 2016-155121.

The resist composition according to the present embodiment described above contains the base material component (A) and the compound (D0) represented by General Formula (d0).

The compound (D0) represented by General Formula (d0) contains an alicyclic group. The alicyclic group is a saturated hydrocarbon group. For this reason, the acid generated upon exposure is not trapped, and the decrease in the acid concentration in the exposed portion can be suppressed.

Further, since the compound (D0) represented by General Formula (d0) has a polar structure (an ether bond, a thioether bond, a carbonyl group, a sulfinyl group, or a sulfonyl group), it can be presumed that the balance between the hydrophilicity and the hydrophobicity and the diffusion control in the entire resist are properly controlled.

As a result, with the resist composition according to the present embodiment, a resist pattern having good fine resolution can be formed.

(Method of Forming Resist Pattern)

A method of forming a resist pattern according to the second aspect according to the present invention is a method including a step of forming a resist film on a support using the resist composition according to the first aspect of the present embodiment described above, a step of exposing the resist film, and a step of developing the exposed resist film to form a resist pattern.

Examples of one embodiment of such a method of forming a resist pattern include a method of forming a resist pattern carried out as described below.

First, the resist composition of the above-described embodiment is applied onto a support with a spinner or the like, and a baking (post-apply baking (PAB)) treatment is carried out, for example, at a temperature condition of 80° C. to 150° C. for 40 to 120 seconds, preferably for 60 to 90 seconds to form a resist film.

Following the selective exposure carried out on the resist film by, for example, exposure through a mask (mask pattern) having a predetermined pattern formed on the mask by using an exposure apparatus such as an electron beam lithography apparatus or an EUV lithography apparatus, or direct irradiation of the resist film for drawing with an electron beam without using a mask pattern, baking treatment (post-exposure baking (PEB)) is carried out, for example, under a temperature condition of 80° C. to 150° C. for 40 to 120 seconds and preferably 60 to 90 seconds.

Next, the resist film is subjected to a developing treatment. The developing treatment is carried out using an alkali developing solution in a case of an alkali developing process, and a developing solution containing an organic solvent (organic developing solution) in a case of a solvent developing process.

After the developing treatment, it is preferable to conduct a rinse treatment. As the rinse treatment, water rinsing using pure water is preferable in a case of an alkali developing process, and rinsing using a rinse liquid containing an organic solvent is preferable in a case of a solvent developing process.

In a case of a solvent developing process, after the developing treatment or the rinsing, the developing solution or the rinse liquid remaining on the pattern can be removed by a treatment using a supercritical fluid.

After the developing treatment or the rinse treatment, drying is conducted. As desired, baking treatment (postbaking) can be carried out following the developing treatment.

In this manner, a resist pattern can be formed.

The support is not specifically limited and a conventionally known support can be used. For example, substrates for electronic components, and such substrates having predetermined wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the support, any support having the above-described substrate on which an inorganic and/or organic film is provided may be used. As the inorganic film, an inorganic antireflection film (inorganic BARC) can be used. Examples of the organic film include an organic antireflection film (organic BARC) and an organic film such as a lower-layer organic film used in a multilayer resist method.

Here, the multilayer resist method is a method in which at least one layer of an organic film (lower-layer organic film) and at least one layer of a resist film (upper-layer resist film) are provided on a substrate, and a resist pattern formed on the upper-layer resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be carried out using radiation such as an ArF excimer laser, a KrF excimer laser, an $F_2$ excimer laser, extreme ultraviolet (EUV) rays, vacuum ultraviolet (VUV) rays, electron beams (EB), X-rays, or soft X-rays. The resist composition is highly useful for a KrF excimer laser, an ArF excimer laser, EB, or EUV, more useful for an ArF excimer laser, EB or EUV, and particularly useful for EB or EUV. That is, the method of forming a resist pattern according to the present embodiment is a particularly useful method in a case where the step of exposing the resist film includes an operation of exposing the resist film to extreme ultraviolet (EUV) rays or electron beams (EB).

The exposure of the resist film can be a general exposure (dry exposure) carried out in air or an inert gas such as nitrogen, or liquid immersion exposure (liquid immersion lithography).

In liquid immersion lithography is an exposure method in which the region between the resist film and the lens at the lowermost position of the lithography apparatus is pre-filled with a solvent (liquid immersion medium) that has a larger refractive index than the refractive index of air, and the exposure (dipping exposure) is carried out in this state.

As the liquid immersion medium, a solvent that exhibits a refractive index larger than the refractive index of air but smaller than the refractive index of the resist film to be exposed is preferable. The refractive index of the solvent is not particularly limited as long as it satisfies the above-described requirements.

Examples of the solvent which exhibits a refractive index that is larger than the refractive index of air but smaller than the refractive index of the resist film include water, fluorine-based inert liquids, silicon-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$, or $C_5H_3F_7$ as the main component, and the boiling point is preferably in a range of 70° to 180° C. and more preferably in a range of 80° to 160° C. A fluorine-based inert liquid having a boiling point in the above-described range is advantageous in that removing the medium used in the liquid immersion after the exposure can be carried out by a simple method.

As a fluorine-based inert liquid, a perfluoroalkyl compound in which all of the hydrogen atoms of the alkyl group are substituted with a fluorine atom is particularly preferable. Examples of these perfluoroalkyl compounds include perfluoroalkyl ether compounds and perfluoroalkyl amine compounds.

Specifically, an example of a suitable perfluoroalkyl ether compound is perfluoro(2-butyl-tetrahydrofuran) (boiling point of 102° C.), and an example of a suitable perfluoroalkyl amine compound is perfluorotributyl amine (boiling point of 174° C.).

As the liquid immersion medium, water is preferable in terms of cost, safety, environment, and versatility.

Examples of the alkali developing solution used for a developing treatment in an alkali developing process include an aqueous solution of 0.1% to 10% by mass tetramethylammonium hydroxide (TMAH).

As the organic solvent contained in the organic developing solution, which is used for a developing treatment in a solvent developing process, any one of the conventionally known organic solvents capable of dissolving the component (A) (component (A) prior to exposure) can be suitably selected from the conventionally known organic solvents. Specific examples of the organic solvent include polar solvents such as a ketone-based solvent, an ester-based solvent, an alcohol-based solvent, a nitrile-based solvent, an amide-based solvent, and an ether-based solvent, and hydrocarbon-based solvents.

A ketone-based solvent is an organic solvent containing C—C(=O)—C in the structure thereof. An ester-based solvent is an organic solvent containing C—C(=O)—O—C in the structure thereof. An alcohol-based solvent is an organic solvent containing an alcoholic hydroxyl group in the structure thereof. An "alcoholic hydroxyl group" indicates a hydroxyl group bonded to a carbon atom of an aliphatic hydrocarbon group. A nitrile-based solvent is an organic solvent containing a nitrile group in the structure thereof. An amide-based solvent is an organic solvent containing an amide group in the structure thereof. An ether-based solvent is an organic solvent containing C—O—C in the structure thereof.

Some organic solvents have a plurality of the functional groups which characterize the above-described solvents in the structure thereof. In such a case, the organic solvent can be classified as any type of solvent having a characteristic functional group. For example, diethylene glycol monomethyl ether can be classified as an alcohol-based solvent or an ether-based solvent.

A hydrocarbon-based solvent consists of a hydrocarbon which may be halogenated and does not have any substituent other than a halogen atom. The halogen atom is preferably a fluorine atom.

Among the above, the organic solvent contained in the organic developing solution is preferably a polar solvent and more preferably a ketone-based solvent, an ester-based solvent, or a nitrile-based solvent.

Examples of ketone-based solvent include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonyl alcohol, acetylcarbinol, acetophenone, methyl naphthyl ketone, isophorone, propylenecarbonate, γ-butyrolactone and methylamyl ketone (2-heptanone). Among these examples, the ketone-based solvent is preferably methylamyl ketone (2-heptanone).

Examples of the ester-based solvent include methyl acetate, butyl acetate, ethyl acetate, isopropyl acetate, amyl acetate, isoamyl acetate, ethyl methoxyacetate, ethyl ethoxyacetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, and propyl-3-methoxypropionate. Among these, the ester-based solvent is preferably butyl acetate.

Examples of the nitrile-based solvent include acetonitrile, propionitrile, valeronitrile, and butyronitrile.

As desired, the organic developing solution may have a conventionally known additive blended. Examples of the additive include surfactants. The surfactant is not particularly limited, and for example, an ionic or non-ionic fluorine-based and/or a silicon-based surfactant can be used. As the surfactant, a non-ionic surfactant is preferable, and a non-ionic fluorine surfactant or a non-ionic silicon-based surfactant is more preferable.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the organic developing solution.

The developing treatment can be carried out by a conventionally known developing method. Examples thereof include a method in which the support is immersed in the developing solution for a predetermined time (a dip method), a method in which the developing solution is cast upon the surface of the support by surface tension and maintained for a predetermined period (a puddle method), a method in which the developing solution is sprayed onto the surface of the support (spray method), and a method in which a developing solution is continuously ejected from a developing solution ejecting and applying nozzle and applied to a support which is scanned at a constant rate while being rotated at a constant rate (dynamic dispense method).

As the organic solvent contained in the rinse liquid used in the rinse treatment after the developing treatment in a case of a solvent developing process, an organic solvent hardly dissolving the resist pattern can be suitably selected and used, among the organic solvents mentioned as organic solvents that are used for the organic developing solution. In general, at least one kind of solvent selected from the group consisting of a hydrocarbon-based solvent, a ketone-based solvent, an ester-based solvent, an alcohol-based solvent, an amide-based solvent, and an ether-based solvent is used. Among these, at least one kind of solvent selected from the group consisting of a hydrocarbon-based solvent, a ketone-based solvent, an ester-based solvent, an alcohol-based solvent, and an amide-based solvent is preferable, at least one kind of solvent selected from the group consisting of an alcohol-based solvent and an ester-based solvent is more preferable, and an alcohol-based solvent is particularly preferable.

The alcohol-based solvent used for the rinse liquid is preferably a monohydric alcohol of 6 to 8 carbon atoms, and the monohydric alcohol may be linear, branched, or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, and benzyl alcohol. Among these, 1-hexanol, 2-heptanol, and 2-hexanol are preferable, and 1-hexanol and 2-hexanol are more preferable.

As the organic solvent, one kind of solvent may be used alone, or two or more kinds of solvents may be used in combination. Further, an organic solvent other than the above-described examples or water may be mixed thereto. However, in consideration of the development characteristics, the amount of water to be blended in the rinse liquid is preferably 30% by mass or less, more preferably 10% by mass or less, still more preferably 5% by mass or less, and most preferably 3% by mass or less with respect to the total amount of the rinse liquid.

A conventionally known additive can be blended with the rinse liquid as necessary. Examples of the additive include surfactants. Examples of the surfactant include the same surfactants as those described above, the surfactant is preferably a non-ionic surfactant and more preferably a non-ionic fluorine surfactant or a non-ionic silicon-based surfactant.

In a case where a surfactant is blended, the amount of the surfactant to be blended is typically in a range of 0.001% to 5% by mass, preferably in a range of 0.005% to 2% by mass, and more preferably in a range of 0.01% to 0.5% by mass with respect to the total amount of the rinse liquid.

The rinse treatment using a rinse liquid (washing treatment) can be carried out by a conventionally known rinse method. Examples of the rinse treatment method include a method in which the rinse liquid is continuously ejected and applied to the support while rotating it at a constant rate (rotational coating method), a method in which the support is immersed in the rinse liquid for a predetermined time (dip method), and a method in which the rinse liquid is sprayed onto the surface of the support (spray method).

According to the method of forming a resist pattern according to the present embodiment described above, since the resist composition according to the first aspect described above is used, it is possible to form a resist pattern that has the good fine resolution.

(Compound)

The compound according to the third aspect of the present invention is a compound represented by General Formula (d0).

[Chemical Formula 71]

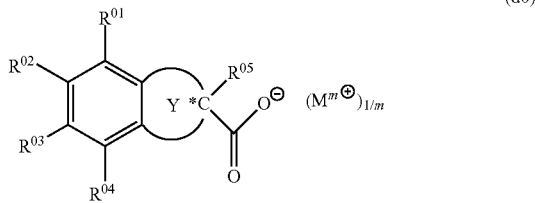

(d0)

[In the formula, $R^{01}$, $R^{02}$, $R^{03}$, and $R^{04}$ each independently represent a hydrogen atom, a hydroxy group, a halogen atom, or an alkyl group having 1 to 5 carbon atoms. Alternatively, $R^{01}$ and $R^{02}$, $R^{02}$ and $R^{03}$, or $R^{03}$ and $R^{04}$ are bonded to each other to form an aromatic ring. The aromatic ring may have a substituent. $R^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group. m represents an integer of 1 or more, and $M^{m+}$ represents an m-valent organic cation.]

The compound according to the third aspect is the same compound as the component (D0) described in the explanation of the resist composition according to the first aspect. The cation moiety and the anion moiety in General Formula (d0) are the same as above.

[Method of Producing Compound (Component (D0))]

The component (D0) is produced, for example, as follows. That is, in the presence of an appropriate base, a compound (d0-0-1) represented by General Formula (d0-0-1) and a salt exchange compound $Xh^-(M^{m+})_{1/m}$ represented by the following formula are subjected to a salt exchange reaction, whereby a compound represented by General Formula (d0) can be produced as the component (D0).

[Chemical Formula 72]

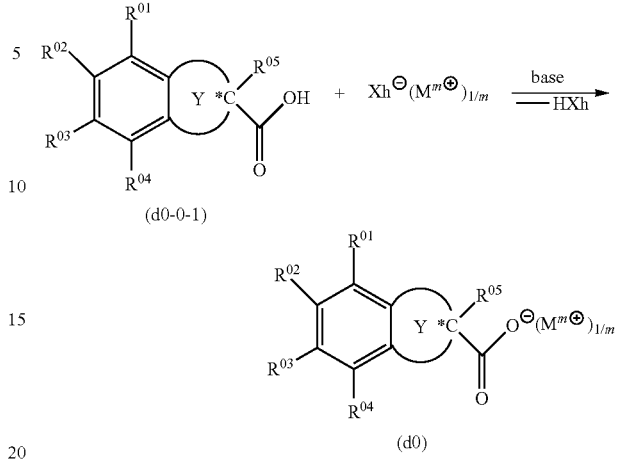

[In the formula, $R^{01}$, $R^{02}$, $R^{03}$, and $R^{04}$ each independently represent a hydrogen atom, a hydroxy group, a halogen atom, or an alkyl group having 1 to 5 carbon atoms. Alternatively, $R^{01}$ and $R^{02}$, $R^{02}$ and $R^{03}$, or $R^{03}$ and $R^{04}$ are bonded to each other to form an aromatic ring. The aromatic ring may have a substituent. $R^{05}$ represents a hydrogen atom or an alkyl group having 1 to 5 carbon atoms. Y represents a group that forms an alicyclic group together with *C (a carbon atom). The alicyclic group that is formed by Y may have a substituent. However, at least one of the carbon atoms that form the alicyclic group is substituted with an ether bond, a thioether bond, a carbonyl group, a sulfinyl group, or a sulfonyl group. m represents an integer of 1 or more, and $M^{m+}$ represents an m-valent organic cation. $Xh^-$ represents a halogen ion.]

In the above formula, examples of the halogen atom constituting the halogen ion of $Xh^-$ include a fluorine atom, a chlorine atom, a bromine atom, and an iodine atom, and among these, a fluorine atom is preferable.

Examples of the base include organic base such as an aqueous solution of tetramethylammonium hydroxide (TMAH), triethylamine, 4-dimethylaminopyridine (DMAP), and pyridine; and inorganic bases such as sodium hydride, $K_2CO_3$, and $Cs_2CO_3$.

The salt exchange between the compound (d0-0-1) and the organic cation ($M^{m+}$) can be carried out in the same manner as the conventionally known salt substitution method. For example, the compound (d0-0-1) and the salt exchange compound $Xh^-(M^{m+})_{1/m}$ are reacted by stirring or the like in a solvent such as water, dichloromethane, acetonitrile, or chloroform to carry out the salt exchange.

The reaction temperature is preferably in a range of about 0° C. to 100° C., more preferably in a range of about 0° C. to 50° C., and still more preferably room temperature.

The reaction time varies depending on the reactivity of the compound (d0-0-1) with the salt exchange compound, the reaction temperature, and the like; however, it is usually preferably 10 minutes or more and 24 hours or less, and more preferably 10 minutes or more and 12 hours or less. The reaction time is more preferably 30 minutes or more.

After the salt exchange reaction is completed, the compound in the reaction solution may be isolated and purified. Conventionally known methods can be used for isolation and purification, and for example, concentration, solvent extraction, distillation, crystallization, recrystallization, chromatography, and the like can be appropriately combined and used.

The structure of the compound obtained as described above can be identified by general organic analysis methods such as $^1$H-nuclear magnetic resonance (NMR) spectroscopy, $^{13}$C-NMR spectroscopy, $^{19}$F-NMR spectroscopy, infrared (IR) absorption spectroscopy, mass spectrometry (MS), elemental analysis, and X-ray crystal diffraction.

(Acid Diffusion-Controlling Agent)

The acid diffusion-controlling agent according to the fourth aspect of the present invention is made from the compound according to the third aspect described above.

Such an acid diffusion-controlling agent is useful as a quencher for a chemical amplification-type resist composition, for example, a quencher for the resist composition according to the first aspect described above. In a case where such an acid diffusion-controlling agent is used in a chemical amplification-type resist composition, a resist pattern having good fine resolution can be formed.

EXAMPLES

Hereinafter, the present invention will be described in more detail based on Examples, but the present invention is not limited to these Examples.

In present Examples, a compound represented by Chemical Formula (D0-1) is denoted by a "compound (D0-1)", and compounds represented by other chemical formulae are also denoted in the same manner.

Production Example of Compound

Production Example 1

1,4-benzodioxane-carboxylic acid (1.5 g, 8.4 mmol) and a compound A (2.9 g, 8.4 mmol) were dissolved in dichloromethane (35 g), and an aqueous solution (15.3 g) of 5% tetramethylammonium hydroxide (TMAH) was added thereto and reacted at room temperature for 30 minutes. After completion of the reaction, the aqueous phase was removed, and the organic phase was washed 10 times with ultrapure water (10 g). The organic phase was concentrated and dried using a rotary evaporator to obtain a compound (D0-1) (1.9 g, yield: 51.1%).

[Chemical Formula 73]

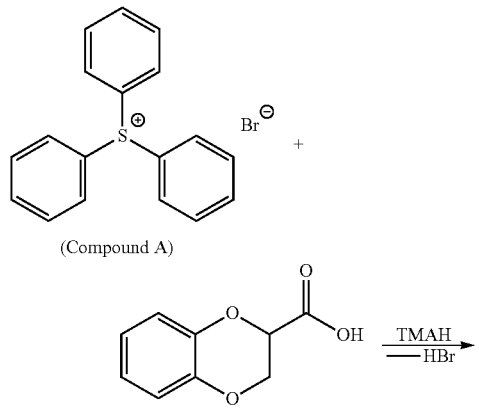

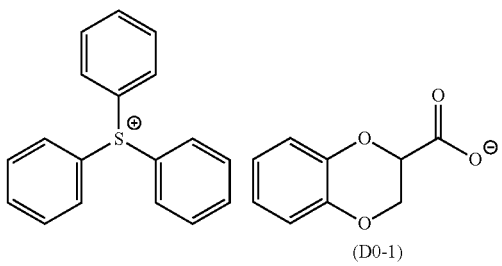

(D0-1)

The obtained compound (D0-1) was subjected to NMR measurement, and the structure thereof was identified from the following measurement results.

$^1$H-NMR (DMSO-d$^6$, 400 MHz) δ (ppm)=7.74 to 7.90 (m, 15H, ArH), 6.67 to 6.79 (m, ArH, 4H), 3.98 to 4.27 (m, —OCHCH$_2$O—, 3H)

Production Examples 2 to 8

Compounds (D0-2) to (D0-8) were obtained in the same manner as in (Production Example 1) described above, except that 1,4-benzodioxane-carboxylic acid in (Production Example 1) described above was changed to each of the corresponding carboxylic acids. The obtained compounds (D0-2) to (D0-8) are shown below.

[Chemical Formula 74]

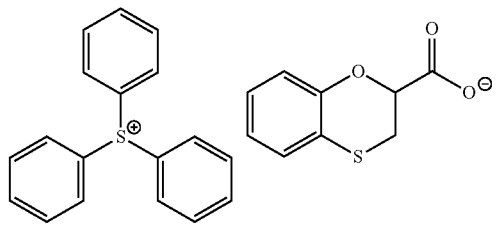

(D0-2)

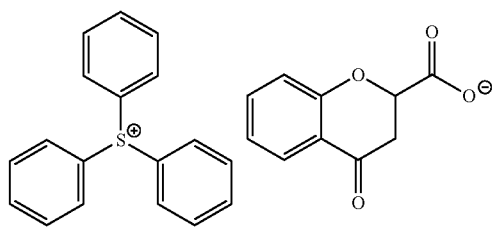

(D0-3)

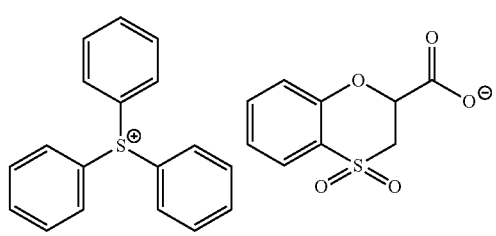

(D0-4)

(D0-5)
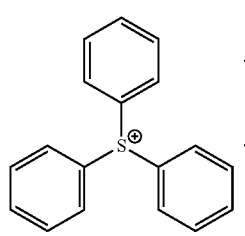

[Chemical Formula 75]

(Compound B)
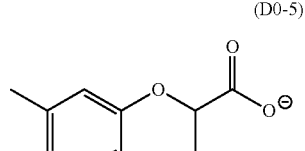

(D0-6)
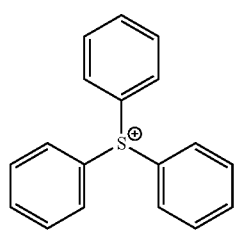

(Compound C)
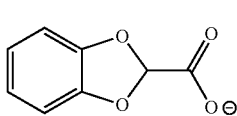

(Compound D)
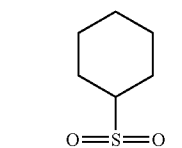

(D0-7)
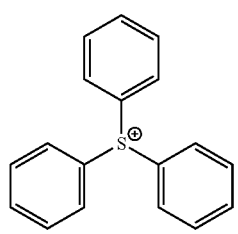

[Chemical Formula 76]

(D0-9)
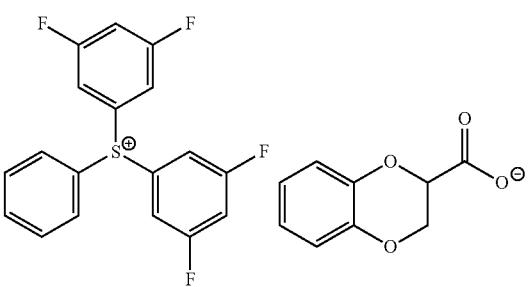

(D0-8)
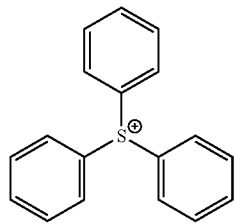

(D0-10)
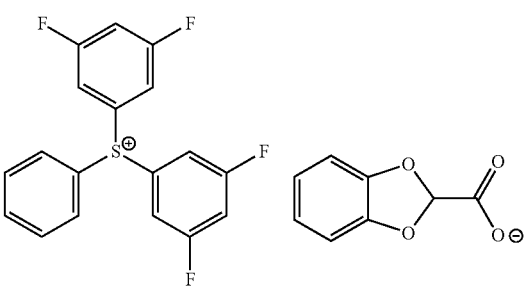

Production Examples 9 to 14

Compounds (D0-9) to (D0-14) were obtained in the same manner as in (Production Example 1) described above, except that 1,4-benzodioxane-carboxylic acid in (Production Example 1) described above was changed to each of the corresponding carboxylic acids, and the compound A in (Production Example 1) was changed to each of the corresponding compounds B, C, and D.

-continued

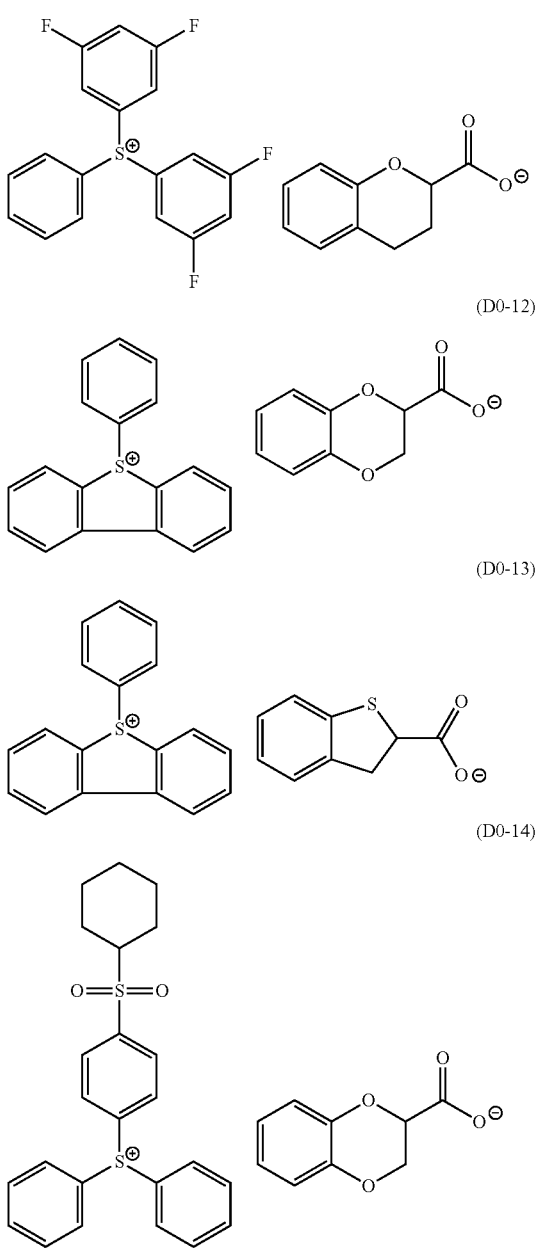

The obtained compounds (D0-2) to (D0-14) were subjected to NMR measurement, and the structures thereof were identified from the following measurement results.

Compound (D0-2): ¹H-NMR (DMSO-d⁶, 400 MHz) δ (ppm)=7.74 to 7.90 (m, 15H, ArH), 6.67 to 7.07 (m, ArH, 4H), 3.76 to 3.81 (m, —OCHCH₂S—, 1H), 2.95 to 3.09 (m, O—CHCH₂S—, 2H)

Compound (D0-3): ¹H-NMR (DMSO-d⁶, 400 MHz) δ (ppm)=7.74 to 7.90 (m, 15H, ArH), 6.85 to 7.70 (m, ArH, 4H), 4.02 to 4.06 (m, —OCHCH₂CO—, 1H), 2.73 to 2.88 (m, O—CHCH₂CO—, 2H)

Compound (D0-4): ¹H-NMR (DMSO-d⁶, 400 MHz) δ (ppm)=7.05 to 7.90 (m, ArH, 19H), 4.01 to 4.05 (m, —OCHCH₂SO₂—, 1H), 3.59 to 3.74 (m, O—CHCH₂SO₂—, 2H)

Compound (D0-5): ¹H-NMR (DMSO-d⁶, 400 MHz) δ (ppm)=7.74 to 7.90 (m, 15H, ArH), 6.76 (s, ArH, 2H), 3.98 to 4.27 (m, —OCHCH₂O—, 3H), 2.21 (s, ArCH₃, 6H)

Compound (D0-6): ¹H-NMR (DMSO-d⁶, 400 MHz) δ (ppm)=7.74 to 7.90 (m, 15H, ArH), 6.66 to 6.79 (m, ArH, 4H), 5.35 (s, —OCHO—, 1H)

Compound (D0-7): ¹H-NMR (DMSO-d⁶, 400 MHz) δ (ppm)=7.74 to 7.90 (m, 15H, ArH), 6.72 to 7.01 (m, ArH, 4H), 4.26 to 4.29 (m, —OCHCH₂CH—, 1H), 2.25 to 2.28 (m, —OCHCH₂CH₂—, 2H), 1.73 to 1.76 (m, —OCHCH₂CH₂Ar—, 2H)

Compound (D0-8): ¹H-NMR (DMSO-d⁶, 400 MHz) δ (ppm)=7.74 to 7.90 (m, 15H, ArH), 6.97 to 7.13 (m, ArH, 4H), 2.71 to 2.74 (m, —SCHCH₂—, 1H), 2.21 to 2.24 (m, —SCHCH₂—, 2H)

Compound (D0-9): ¹H-NMR (DMSO-d⁶, 400 MHz) δ (ppm)=7.77 to 7.98 (m, ArH, 11H), 6.67 to 6.79 (m, ArH, 4H), 3.98 to 4.27 (m, —OCHCH₂O—, 3H)

Compound (D0-10): ¹H-NMR (DMSO-d⁶, 400 MHz) δ (ppm)=7.77 to 7.98 (m, ArH, 11H), 6.66 to 6.79 (m, ArH, 4H), 5.35 (s, —OCHO—, 1H)

Compound (D0-11): ¹H-NMR (DMSO-d⁶, 400 MHz) δ (ppm)=7.77 to 7.98 (m, ArH, 11H), 6.72 to 7.01 (m, ArH, 4H), 4.26 to 4.29 (m, —OCHCH₂CH₂—, 1H), 2.25 to 2.28 (m, —OCHCH₂CH₂—, 2H), 1.73 to 1.76 (m, —OCHCH₂CH₂—, 2H)

Compound (D0-12): ¹H-NMR (DMSO-d⁶, 400 MHz) δ (ppm)=8.50 (d, 2H, ArH), 8.37 (d, 2H, ArH), 7.93 (t, 2H, ArH), 7.55 to 7.75 (m, 7H, ArH), 6.67 to 6.79 (m, ArH, 4H), 3.98 to 4.27 (m, —OCHCH₂O—, 3H)

Compound (D0-13): ¹H-NMR (DMSO-d⁶, 400 MHz) δ (ppm)=8.50 (d, 2H, ArH), 8.37 (d, 2H, ArH), 7.93 (t, 2H, ArH), 7.55 to 7.75 (m, 7H, ArH), 6.97 to 7.13 (m, ArH, 4H), 2.71 to 2.74 (m, —SCHCH₂—, 1H), 2.21 to 2.24 (m, —SCHCH₂—, 2H)

Compound (D0-14): ¹H-NMR (DMSO-d⁶, 400 MHz) δ (ppm)=7.70 to 8.22 (m, ArH, 14H), 6.67 to 6.79 (m, ArH, 4H), 3.98 to 4.27 (m, —OCHCH₂O—, 3H), 3.30 to 3.45 (m, —SO₂CH—, 1H), 1.09 to 1.90 (m, Cyclohexyl, 10H)

Preparation of Resist Composition

Examples 1 to 21 and Comparative Examples 1 to 15

Each of the components shown in Tables 1 and 2 was mixed and dissolved to prepare a resist composition of each Example.

TABLE 1

| | Component (A) | Component (B) | Component (D) | Component (S) |
|---|---|---|---|---|
| Example 1 | (A)-1 [100] | (B)-1 [18.7] | (D0)-1 [4.3] | (S)-1 [6400] |
| Example 2 | (A)-1 [100] | (B)-1 [18.7] | (D0)-2 [4.5] | (S)-1 [6400] |
| Example 3 | (A)-1 [100] | (B)-1 [18.7] | (D0)-3 [4.4] | (S)-1 [6400] |
| Example 4 | (A)-1 [100] | (B)-1 [18.7] | (D0)-4 [4.8] | (S)-1 [6400] |
| Example 5 | (A)-1 [100] | (B)-1 [18.7] | (D0)-5 [4.6] | (S)-1 [6400] |
| Example 6 | (A)-1 [100] | (B)-1 [18.7] | (D0)-6 [4.2] | (S)-1 [6400] |
| Example 7 | (A)-1 [100] | (B)-1 [18.7] | (D0)-7 [4.3] | (S)-1 [6400] |
| Example 8 | (A)-1 [100] | (B)-1 [18.7] | (D0)-8 [4.3] | (S)-1 [6400] |

TABLE 1-continued

| | Component (A) | Component (B) | Component (D) | Component (S) |
|---|---|---|---|---|
| Example 9 | (A)-1 [100] | (B)-1 [18.7] | (D0)-9 [5.0] | (S)-1 [6400] |
| Example 10 | (A)-1 [100] | (B)-1 [18.7] | (D0)-10 [4.9] | (S)-1 [6400] |
| Example 11 | (A)-1 [100] | (B)-1 [18.7] | (D0)-11 [5.0] | (S)-1 [6400] |
| Example 12 | (A)-1 [100] | (B)-1 [18.7] | (D0)-12 [4.3] | (S)-1 [6400] |
| Example 13 | (A)-1 [100] | (B)-1 [18.7] | (D0)-13 [4.3] | (S)-1 [6400] |
| Example 14 | (A)-1 [100] | (B)-1 [18.7] | (D0)-14 [5.7] | (S)-1 [6400] |
| Example 15 | (A)-1 [100] | (B)-2 [17.1] | (D0)-3 [4.4] | (S)-1 [6400] |
| Example 16 | (A)-1 [100] | (B)-2 [17.1] | (D0)-7 [4.3] | (S)-1 [6400] |
| Example 17 | (A)-1 [100] | (B)-2 [17.1] | (D0)-9 [5.0] | (S)-1 [6400] |
| Example 18 | (A)-2 [100] | (B)-2 [17.1] | (D0)-1 [4.3] | (S)-1 [6400] |
| Example 19 | (A)-2 [100] | (B)-2 [17.1] | (D0)-7 [4.3] | (S)-1 [6400] |
| Example 20 | (A)-2 [100] | (B)-2 [17.1] | (D0)-14 [5.7] | (S)-1 [6400] |
| Example 21 | (A)-2 [100] | (B)-1 [18.7] | (D0)-9 [5.0] | (S)-1 [6400] |

TABLE 2

| | Component (A) | Component (B) | Component (D) | Component (S) |
|---|---|---|---|---|
| Comparative Example 1 | (A)-1 [100] | (B)-1 [18.7] | (D1)-1 [4.3] | (S)-1 [6400] |
| Comparative Example 2 | (A)-1 [100] | (B)-1 [18.7] | (D1)-2 [4.1] | (S)-1 [6400] |
| Comparative Example 3 | (A)-1 [100] | (B)-1 [18.7] | (D1)-6 [3.7] | (S)-1 [6400] |
| Comparative Example 4 | (A)-1 [100] | (B)-1 [18.7] | (D1)-7 [3.8] | (S)-1 [6400] |
| Comparative Example 5 | (A)-1 [100] | (B)-1 [18.7] | (D1)-8 [4.1] | (S)-1 [6400] |
| Comparative Example 6 | (A)-1 [100] | (B)-1 [18.7] | (D1)-3 [5.0] | (S)-1 [6400] |
| Comparative Example 7 | (A)-1 [100] | (B)-1 [18.7] | (D1)-4 [4.2] | (S)-1 [6400] |
| Comparative Example 8 | (A)-1 [100] | (B)-1 [18.7] | (D1)-5 [5.7] | (S)-1 [6400] |
| Comparative Example 9 | (A)-1 [100] | (B)-2 [17.1] | (D1)-1 [4.3] | (S)-1 [6400] |
| Comparative Example 10 | (A)-1 [100] | (B)-2 [17.1] | (D1)-3 [5.0] | (S)-1 [6400] |
| Comparative Example 11 | (A)-1 [100] | (B)-2 [17.1] | (D1)-6 [3.7] | (S)-1 [6400] |
| Comparative Example 12 | (A)-2 [100] | (B)-2 [17.1] | (D1)-1 [4.3] | (S)-1 [6400] |
| Comparative Example 13 | (A)-2 [100] | (B)-2 [17.1] | (D1)-8 [4.1] | (S)-1 [6400] |
| Comparative Example 14 | (A)-2 [100] | (B)-2 [17.1] | (D1)-5 [5.7] | (S)-1 [6400] |
| Comparative Example 15 | (A)-2 [100] | (B)-1 [18.7] | (D1)-3 [5.0] | (S)-1 [6400] |

In Tables 1 and 2, each abbreviation has the following meaning. The numerical values in the brackets are blending amounts (parts by mass).

(A)-1: The polymer compound represented by Chemical Formula (A-1). This polymer compound (A-1) was obtained by radical polymerization using monomers from which constitutional units constituting the polymer compound are derived, at a predetermined molar ratio. As a result of a GPC measurement to determine the weight-average molecular weight (Mw) in terms of standard polystyrene, this polymer compound (A-1) had a weight-average molecular weight of 5,400 and a molecular weight dispersity (Mw/Mn) of 1.56. The copolymer compositional ratio (the ratio (molar ratio) among constitutional units in the structural formula) determined by $^{13}$C-NMR is l/m/n=30/60/10.

(A)-2: The polymer compound represented by Chemical Formula (A-2). This polymer compound (A-2) was obtained by radical polymerization using monomers from which constitutional units constituting the polymer compound are derived, at a predetermined molar ratio. As a result of a GPC measurement to determine the weight-average molecular weight (Mw) in terms of standard polystyrene, this polymer compound (A-2) had a weight-average molecular weight of 7,100 and a molecular weight dispersity (Mw/Mn) of 1.70. The copolymer compositional ratio (the ratio (molar ratio) among constitutional units in the structural formula) determined by $^{13}$C-NMR is l/m/n=40/50/10.

[Chemical Formula 77]

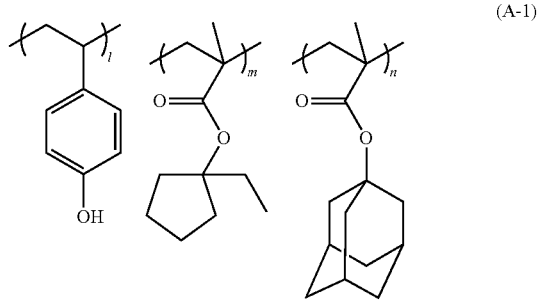

(A-1)

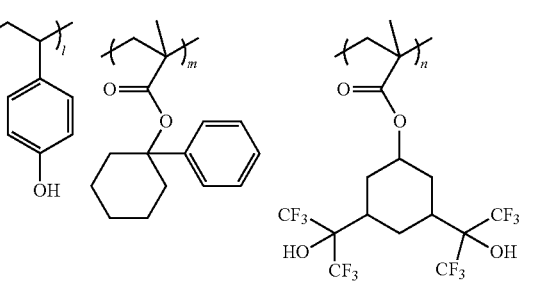

(A-2)

(B)-1: an acid generator composed of a compound represented by Chemical Formula (B-1).

(B)-2: an acid generator composed of a compound represented by Chemical Formula (B-2).

[Chemical Formula 78]

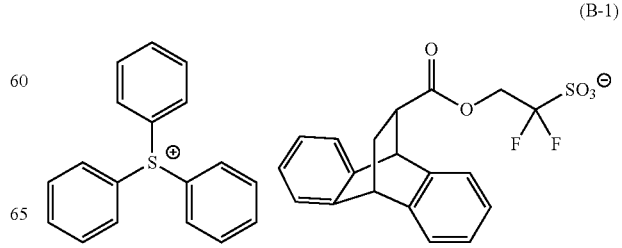

(B-1)

(B-2)

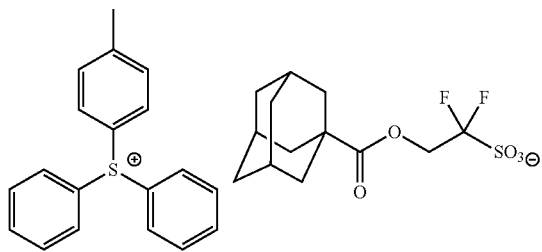

(D0)-1 to (D0)-14: Acid diffusion-controlling agents composed of compounds each represented by Chemical Formulae (D0-1) to (D0-14).

(D1)-1 to (D1)-8: Acid diffusion-controlling agents composed of compounds each represented by Chemical Formulae (D1-1) to (D1-8).

[Chemical Formula 79]

(D1-1)

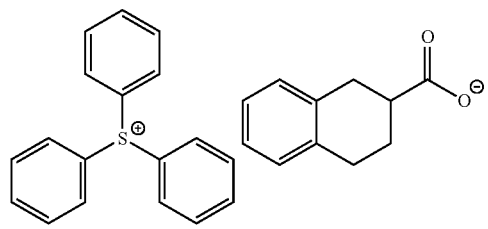

(D1-2)

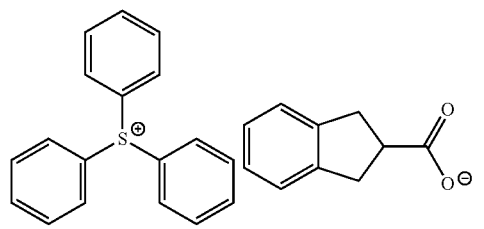

(D1-3)

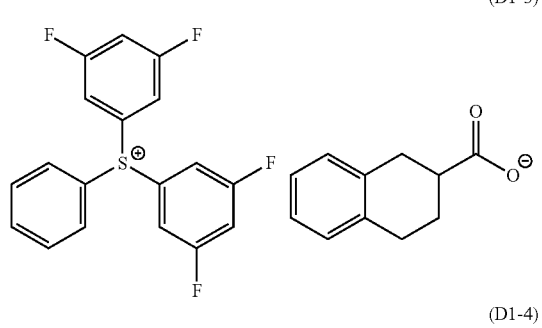

(D1-4)

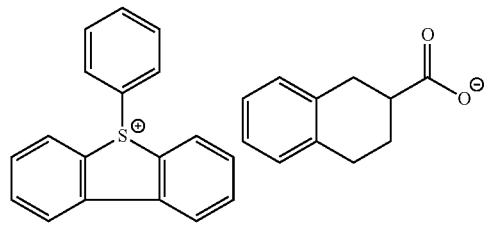

(D1-5)

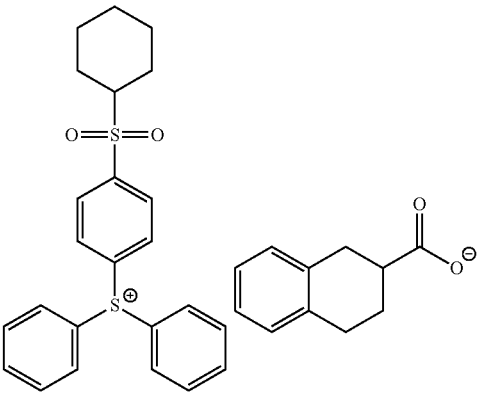

(D1-6)

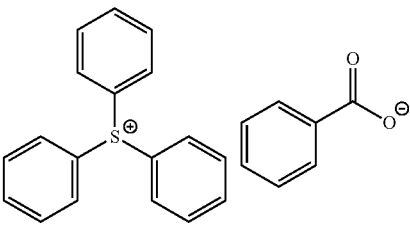

[Chemical Formula 80]

(D1-7)

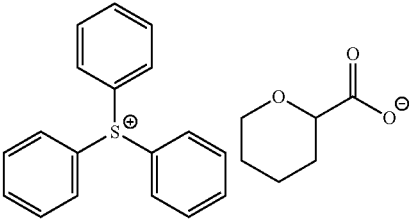

(D1-8)

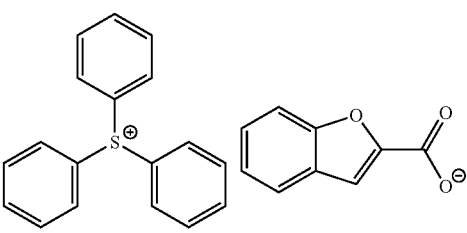

(S)-1: a mixed solvent of propylene glycol monomethyl ether acetate/propylene glycol monomethyl ether=60/40 (mass ratio)

<Formation of Resist Pattern>

The resist composition of each Example was applied onto an 8-inch silicon substrate which had been subjected to a hexamethyl disilazane (HMDS) treatment using a spinner, the coated wafer was subjected to a post-apply baking (PAB) treatment on a hot plate at a temperature of 110° C. for 60 seconds so that the coated wafer was dried to form a resist film having a film thickness of 50 nm.

Next, the resist film was subjected to drawing (exposure) to obtain a contact hole pattern (hereinafter, referred to as a "CH pattern") in which holes having a diameter of 32 nm were arranged at equal intervals (pitch: 64 nm) by using an electron beam lithography apparatus JEOL-JBX-9300FS (manufactured by JEOL Ltd.) at an accelerating voltage of 100 kV. Thereafter, a post-exposure baking (PEB) treatment was carried out on the resist film at 110° C. for 60 seconds.

Subsequently, alkali development was carried out at 23° C. for 60 seconds using an aqueous solution of 2.38% by mass tetramethylammonium hydroxide (TMAH) "NMD-3" (trade name, manufactured by TOKYO OHKA KOGYO CO., LTD.).

Thereafter, rinsing was carried out with pure water for 15 seconds.

As a result, a CH pattern in which holes having a diameter of 32 nm were arranged at equal intervals (pitch: 64 nm) was formed.

[Evaluation of Critical Dimension Uniformity (CDU) of Pattern]

The CH pattern formed according to "Formation of resist pattern" described above was observed from the upper side of the CH pattern, and the hole diameter (nm) of each of the holes was measured with a length-measuring scanning electron microscope (SEM, accelerating voltage: 500 V, trade name: CG5000, manufactured by Hitachi High-Tech Corporation). Then, three times (3σ) the standard deviation (σ) calculated from the measurement result was determined. The results are shown in Tables 3 and 4 as "CDU (nm)".

The lower the value of 36 obtained as described above is, the higher the critical dimension (CD) uniformity of the plurality of holes formed in the resist film is.

[Evaluation of Limiting Resolution]

The limiting resolution at the optimum exposure amount (Eop) with which the above-described CH pattern was formed, specifically, the hole diameter (nm) of the pattern that was resolved when gradually reducing the exposure amount from the optimum exposure amount, was determined using a scanning electron microscope S-9380 (manufactured by Hitachi High-Tech Corporation). The results are shown in Tables 3 and 4 as "Limiting resolution (nm)".

TABLE 3

| | PAB (° C.) | PEB (° C.) | CDU (nm) | Limiting resolution (nm) |
|---|---|---|---|---|
| Example 1 | 110 | 110 | 4.2 | 24 |
| Example 2 | 110 | 110 | 4.4 | 24 |
| Example 3 | 110 | 110 | 4.3 | 24 |
| Example 4 | 110 | 110 | 4.3 | 24 |
| Example 5 | 110 | 110 | 4.7 | 24 |
| Example 6 | 110 | 110 | 4.4 | 24 |
| Example 7 | 110 | 110 | 5.0 | 28 |
| Example 8 | 110 | 110 | 4.9 | 28 |
| Example 9 | 110 | 110 | 4.1 | 24 |
| Example 10 | 110 | 110 | 4.3 | 24 |
| Example 11 | 110 | 110 | 4.8 | 24 |
| Example 12 | 110 | 110 | 4.6 | 24 |
| Example 13 | 110 | 110 | 5.0 | 28 |
| Example 14 | 110 | 110 | 4.4 | 24 |
| Example 15 | 110 | 110 | 4.3 | 24 |
| Example 16 | 110 | 110 | 4.6 | 28 |
| Example 17 | 110 | 110 | 4.0 | 24 |
| Example 18 | 110 | 110 | 4.3 | 24 |
| Example 19 | 110 | 110 | 4.7 | 28 |
| Example 20 | 110 | 110 | 4.4 | 24 |
| Example 21 | 110 | 110 | 4.3 | 24 |

TABLE 4

| | PAB (° C.) | PEB (° C.) | CDU (nm) | Limiting resolution (nm) |
|---|---|---|---|---|
| Comparative Example 1 | 110 | 110 | 5.7 | 32 |
| Comparative Example 2 | 110 | 110 | 5.5 | 32 |
| Comparative Example 3 | 110 | 110 | 6.0 | 24 |
| Comparative Example 4 | 110 | 110 | 5.8 | 24 |
| Comparative Example 5 | 110 | 110 | 6.4 | 32 |
| Comparative Example 6 | 110 | 110 | 5.5 | 32 |
| Comparative Example 7 | 110 | 110 | 5.8 | 32 |
| Comparative Example 8 | 110 | 110 | 5.6 | 32 |
| Comparative Example 9 | 110 | 110 | 5.5 | 32 |
| Comparative Example 10 | 110 | 110 | 5.3 | 32 |
| Comparative Example 11 | 110 | 110 | 5.8 | 24 |
| Comparative Example 12 | 110 | 110 | 5.6 | 32 |
| Comparative Example 13 | 110 | 110 | 6.3 | 32 |
| Comparative Example 14 | 110 | 110 | 5.8 | 32 |
| Comparative Example 15 | 110 | 110 | 5.6 | 32 |

From the results shown in Tables 3 and 4, it can be seen that in the case of resist compositions, the CDU value is small and the limiting resolution value is equal to or small as compared with the case of the resist compositions of Comparative Examples. As a result, it can be confirmed that in a case where the present invention is applied, a resist pattern having good fine resolution can be formed in the formation of the resist pattern.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

What is claimed is:

1. A resist composition which generates an acid upon exposure and exhibits changed solubility in a developing solution under action of acid, the resist composition comprising:
a base material component (A) exhibiting changed solubility in a developing solution under action of acid; and
a compound (D0) represented by General Formula (d0):

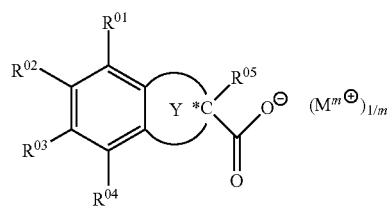

(d0)

wherein $R^{01}$, $R^{02}$, $R^{03}$ and $R^{04}$ each independently represent a hydrogen atom, a hydroxy group, a halogen atom, or an alkyl group having 1 to 5 carbon atoms, alternatively, $R^{01}$ and $R^{02}$, $R^{02}$ and $R^{03}$, or $R^{03}$ and $R^{04}$ are bonded to each other to form an aromatic ring, the aromatic ring may have a substituent, $R^{05}$ represents a hydrogen atom or an alkyl group having 1 to 5 carbon atoms, Y represents a group that forms an alicyclic group together with a carbon atom *C, the alicyclic group that is formed by Y may have a substituent, where at least one of carbon atoms that form the alicyclic group is substituted with an ether bond, a thioether bond, a carbonyl group, a sulfinyl group, or a sulfonyl group, and m represents an integer of 1 or more, where $M^{m+}$ represents an m-valent organic cation.

2. The resist composition according to claim 1, wherein a content of the compound (D0) is in a range of 1 to 35 parts by mass with respect to 100 parts by mass of the base material component (A).

3. The resist composition according to claim 1, further comprising an acid generator component (B) generating an acid upon exposure, provided that the compound (D0) is excluded from the acid generator component (B).

4. The resist composition according to claim 1, wherein the base material component (A) contains a resin component (A1), and the resin component (A1) has a constitutional unit (a1) that contains an acid-decomposable group having a polarity which is increased by action of an acid.

5. A method of forming a resist pattern, comprising:
forming a resist film on a support using the resist composition according to claim 1;
exposing the resist film; and
developing the exposed resist film to form a resist pattern.

6. The method of forming a resist pattern according to claim 5, wherein the resist film is exposed with extreme ultraviolet (EUV) rays or electron beam (EB).

7. A compound represented by General Formula (d0):

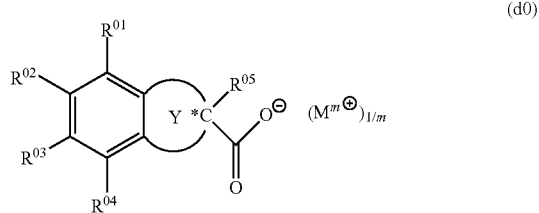

(d0)

wherein $R^{01}$, $R^{02}$, $R_{03}$, and $R^{04}$ each independently represents a hydrogen atom, a hydroxy group, a halogen atom, or an alkyl group having 1 to 5 carbon atoms, alternatively, $R^{01}$ and $R^{02}$, $R^{02}$ and $R^{03}$, or $R^{03}$ and $R^{04}$ are bonded to each other to form an aromatic ring, the aromatic ring may have a substituent, R represents a hydrogen atom or an alkyl group having 1 to 5 carbon atoms, Y represents a group that forms an alicyclic group together with a carbon atom *C, the alicyclic group that is formed by Y may have a substituent, where at least one of carbon atoms that form the alicyclic group is substituted with an ether bond, a thioether bond, a carbonyl group, a sulfinyl group, or a sulfonyl group, and m represents an integer of 1 or more, where $M^{m+}$ represents an m-valent organic cation selected from the group consisting of a sulfonium cation and an iodonium cation.

8. An acid diffusion-controlling agent comprising a compound represented by General Formula (d0):

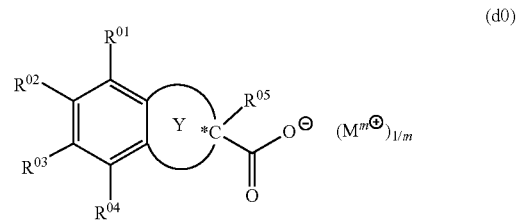

(d0)

wherein $R^{01}$, $R^{02}$, $R^{03}$, and $R^{04}$ each independently represent a hydrogen atom, a hydroxy group, a halogen atom, or an alkyl group having 1 to 5 carbon atoms, alternatively, $R^{01}$ and $R^{02}$, $R^{02}$ and $R^{03}$, or $R^{03}$ and $R^{04}$ are bonded to each other to form an aromatic ring, the aromatic ring may have a substituent, $R^{05}$ represents a hydrogen atom or an alkyl group having 1 to 5 carbon atoms, Y represents a group that forms an alicyclic group together with a carbon atom *C, the alicyclic group that is formed by Y may have a substituent, where at least one of carbon atoms that form the alicyclic group is substituted with an ether bond, a thioether bond, a carbonyl group, a sulfinyl group, or a sulfonyl group, and m represents an integer of 1 or more, where $M^{m+}$ represents an m-valent organic cation.

9. The acid diffusion-controlling agent according to claim 8, wherein $M^{m+}$ represents an m-valent organic cation selected from a group consisting of a sulfonium cation and an iodonium cation.

* * * * *